United States Patent von Deyn et al.

[11] Patent Number: 6,153,759
[45] Date of Patent: Nov. 28, 2000

[54] HETEROCYCLIC BENZOYL INTERMEDIATES FOR HERBICIDAL COMPOUNDS

[75] Inventors: Wolfgang von Deyn, Neustadt; Regina Luise Hill, Speyer; Uwe Kardorff, Mannheim; Stefan Engel, Idstein; Martina Otten, Ludwigshafen; Marcus Vossen, Mannheim; Peter Plath, Frankenthal; Harald Rang, Altrip; Albrecht Harreus, Ludwigshafen; Franz Röhl, Schifferstadt; Helmut Walter, Obrigheim; Karl-Otto Westphalen, Speyer; Ulf Misslitz, Neustadt, all of Germany

[73] Assignee: BASF Aktiengesellschaft, Ludwigshafen, Germany

[21] Appl. No.: 09/226,142

[22] Filed: Jan. 7, 1999

Related U.S. Application Data

[62] Division of application No. 08/894,247, filed as application No. PCT/EP96/00593, Feb. 13, 1996, Pat. No. 6,004,903.

[30] Foreign Application Priority Data

Feb. 24, 1995 [DE] Germany ............... 19506574

[51] Int. Cl.[7] ............ C07D 307/42; C07D 333/32; C07D 261/12; C07D 263/20; C07D 271/08

[52] U.S. Cl. .......... 548/131; 548/132; 548/133; 548/214; 548/236; 548/237; 548/247; 549/61; 549/62; 549/79; 549/80; 549/474; 549/498; 549/499; 549/500

[58] Field of Search .............. 548/131, 132, 548/133, 214, 236, 237, 247; 549/61, 62, 79, 80, 474, 498, 499, 500

[56] References Cited

U.S. PATENT DOCUMENTS

| | | | |
|---|---|---|---|
| 3,840,548 | 10/1974 | Malen et al. | 260/302 |
| 4,315,766 | 2/1982 | Hamprecht et al. | 71/88 |
| 4,615,726 | 10/1986 | Schmierer et al. | 71/92 |
| 5,143,914 | 9/1992 | Dininno et al. | 514/210 |
| 5,380,701 | 1/1995 | Winternitz et al. | 504/243 |
| 5,633,271 | 5/1997 | Amoo et al. | 514/365 |
| 5,824,802 | 10/1998 | Benko et al. | 544/140 |
| 5,846,906 | 12/1998 | Von Deyn et al. | 504/221 |
| 5,846,907 | 12/1998 | Von Deyn et al. | 504/221 |

FOREIGN PATENT DOCUMENTS 2129090 12/1971 Germany.
2914915 10/1980 Germany.
3345901 6/1985 Germany.
94/10155 5/1994 WIPO.

OTHER PUBLICATIONS

Huebner et al., Chemical Abstract 59:3867b, 1963.
Reinhoudt et al., Chemical Abstract 82:16688, 1975.
Gompper et al., Chemical Abstract 93:7600, 1980.
Reinhoudt et al., Chemical Abstract 94:64755, 1981.
Hagiwara et al., Chemical Absract 106:119893, 1987.
Shimo et al., Chemical Abstract 116:235381, 1992.
Kato et al., Chemical Abstract 119:117265, 1993.
Kuno et al., Chemical Abstract 123:256771, 1995.
Cantegril et al., Chemical Abstract 124:335658, 1996.
Gericke et al., Chemical Abstract 124:343303, 1996.
Mazza et al., Chemical Abstract 126:140911, 1997.
Ijichi et al., Chemical Abstract 125:114637, 1996.
Schnur et al., *J. Med. Chem.*, vol. 29, 1986, pp. 770–778.
Eugster et al., *Helvetica Chimica Acta*, 46, 1963, pp. 814–851 (p. 846 esp., compound XIV).
*J. of Amer. Chem. Soc.*, 100:24, Nov. 22, 1978, pp. 7602–7608.

*Primary Examiner*—Mukund J. Shah
*Assistant Examiner*—Deepak R. Rao
*Attorney, Agent, or Firm*—Keil & Weinkauf

[57] ABSTRACT

Heterocyclic substituted benzoyl derivatives of the formula

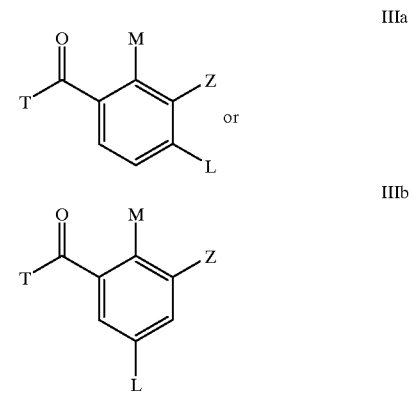

where

Z is a 5-membered or 6-membered heterocyclic, saturated or unsaturated radical containing one to three hetero atoms selected from the group consisting of oxygen, sulfur and nitrogen, useful as intermediates for herbicidal compounds.

7 Claims, No Drawings

HETEROCYCLIC BENZOYL INTERMEDIATES FOR HERBICIDAL COMPOUNDS

This application is a division of application Ser. No. 08/894,247, filed Aug. 14, 1997, now U.S. Pat. No. 6,004,903 which is a 371 of PCT/EP96/00593 filed Feb. 13, 1996.

The present invention relates to novel benzoyl derivatives having a herbicidal action, processes for the preparation of the benzoyl derivatives, agents which contain them and the use of these derivatives or agents containing them for weed control.

Herbicidal 2-aroylcyclohexanediones are disclosed in the literature, for example in EP 90262, EP 135191, EP 186118, EP 186119, EP 186120, EP 319075, WO 9005712, JO 3052862 and JO 3120202.

However, the herbicidal properties of the known compounds and the tolerance by crops are satisfactory only to a limited extent.

It is an object of the present invention to provide novel 2-aroylcyclohexanediones having improved properties.

We have found that this object is achieved by novel benzoyl derivatives of the formula I

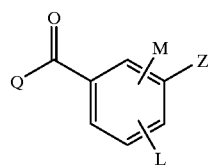

where

L and M are each hydrogen, $C_1$–$C_6$-alkyl, $C_2$–$C_6$-alkenyl, $C_2$–$C_6$-alkynyl or $C_1$–$C_4$-alkoxy, where these groups may be unsubstituted or substituted by one to five halogen atoms or $C_1$–$C_4$-alkoxy, or are each halogen, cyano, nitro, a group —$(Y)_n$—$S(O)_m R^7$ or a group —$(Y)_n$—CO—$R^8$, Z is a 5-membered or 6-membered heterocyclic, saturated or unsaturated radical containing one to three hetero atoms selected from the group consisting of oxygen, sulfur and nitrogen, which is unsubstituted or substituted by halogen, cyano, nitro, a group —CO—$R^8$, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino or unsubstituted or halogen-, cyano-, nitro-, $C_1$–$C_4$-alkyl- or $C_1$–$C_4$-haloalkyl-substituted phenyl or by an oxo group which may also be present in tautomeric form as a hydroxyl group, or which forms a bicyclic system with a fused-on phenyl ring substituted by halogen, cyano, nitro, $C_1$–$C_4$-alkyl or $C_1$–$C_4$-haloalkyl, a fused-on carbocyclic structure or a fused-on second heterocyclic structure which is unsubstituted or substituted by halogen, cyano, nitro, $C_1$–$C_4$-alkyl, di-$C_1$–$C_4$-alkylamino, $C_1$–$C_4$-alkoxy, $C_1$–$C_4$-haloalkoxy or $C_1$–$C_4$-haloalkyl, Y is O or $NR^9$, n is zero or one, m is zero, one or two, $R^7$ is $C_1$–$C_4$-alkyl, $C_1$–$C_4$-haloalkyl oder $NR^9 R^{10}$, $R^8$ is $C_1$–$C_4$-alkyl, $C_1$–$C_4$-haloalkyl, $C_1$–$C_4$-alkoxy, or $NR^9 R^{10}$, $R^9$ is hydrogen or $C_1$–$C_4$-alkyl, $R^{10}$ is $C_1$–$C_4$-alkyl, Q is a cyclohexane-1,3-dione ring bonded in the 2-position and of the formula II,

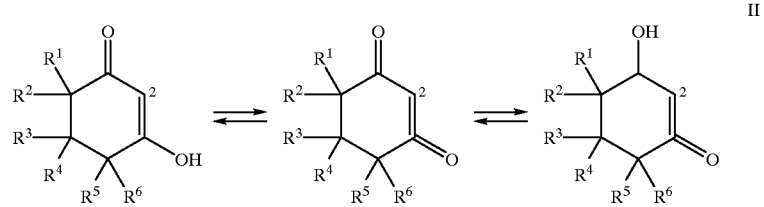

where $R^1$, $R^2$, $R^4$ and $R^6$ are each hydrogen or $C_1$–$C_4$-alkyl, $R^5$ is hydrogen, $C_1$–$C_4$-alkyl or a group —$COOR^{10}$ and $R^3$ is hydrogen, $C_1$–$C_4$-alkyl or $C_3$–$C_6$-cycloalkyl, where these groups may carry from one to three of the following substituents: halogen, $C_1$–$C_4$-alkylthio and $C_1$–$C_4$-alkoxy, or $R^3$ is tetrahydropyran-3-yl, tetrahydropyran-4-yl or tetrahydrothiopyran-3-yl or $R^3$ and $R^5$ together form a bond or a three-membered to six-membered carbocyclic ring, and conventional agricultural salts of the compounds I.

Benzoyl derivatives of the formula Ia

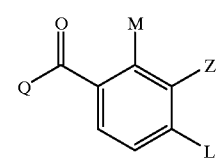

where L is $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and Q and Z have the abovementioned meanings, are preferred.

Other preferred benzoyl derivatives are those of the Formula Ib

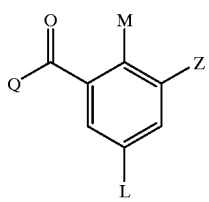

where L and M are each $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and Q and Z have the meanings stated in claim 1.

Compounds of the formula Ic are obtained by reacting compounds of the formula II with a benzoic acid derivative of the formula III and subjecting the product to a rearrangement reaction to give benzoyl derivatives of the formula Ic:

Scheme 1

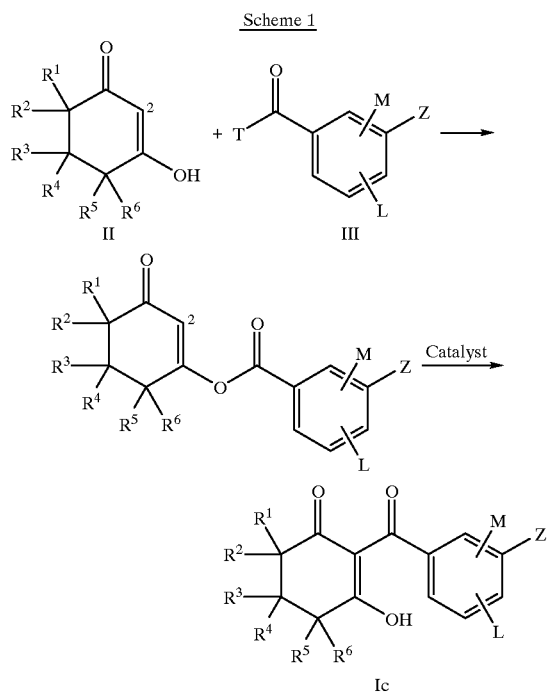

In the abovementioned formulae, T is halogen and L, M and Z have the abovementioned meanings.

The first step of the reaction sequence, the acylation, is carried out in a generally known manner, for example by adding an acyl chloride of the formula III (T=Cl) to a solution or suspension of a cyclohexane-1,3-dione II in the presence of an auxiliary base. The reactants and the auxiliary base are advantageously used in equimolar amounts. A small excess, for example from 1.2 to 1.5 mole equivalents, based on II, of the auxiliary base may be advantageous.

Suitable auxiliary bases are tertiary alkylamines, pyridine and alkali metal carbonates. For example, methylene chloride, diethyl ether, toluene or ethyl acetate can be used as a solvent.

During the addition of the acyl chloride, the reaction mixture is preferably cooled to 0–10° C., after which stirring is carried out at from 20 to 100° C., in particular from 25 to 50° C., until the reaction is complete. Working up is carried out in a conventional manner, for example the reaction mixture is poured into water and the desired product is extracted, for example with methylene chloride. After drying of the organic phase and removal of the solvent, the crude enol ester can be used for the rearrangement reaction without further purification. Preparation examples for benzoyl enol esters of cyclohexan-1,3-diones appear in, for example, EP-A 186 118 or U.S. Pat. No. 4,780,127.

The rearrangement of the enol esters to give the compounds of the formula Ic is advantageously carried out at from 20 to 40° C. in a solvent and in the presence of an auxiliary base and with the aid of a cyano compound as a catalyst.

For example, acetonitrile, methylene chloride, 1,2-dichloroethane, ethyl acetate or toluene can be used as solvent. The preferred solvent is acetonitrile. Suitable auxiliary bases are tertiary alkylamines, pyridine and alkali metal carbonates, which are preferably used in an equimolar amount or in a four-fold excess, based on the benzoyl enol ester. A preferred auxiliary base is triethylamine in twice the equimolar amount.

Examples of suitable catalysts are potassium cyanide and acetonecyanohydrin, preferably in an amount of from 1 to 50 mol percent, based on the enol ester. Acetonecyanohydrin is preferably added, for example in an amount of from 5 to 15, in particular 10, mol percent. Examples of the cyanide-catalyzed rearrangement of enol esters of cyclohexane-1,3-diones appear in, for example, EP-A 186 118 or U.S. Pat. No. 4,780,127.

Working up is carried out in a manner known per se. For example, the reaction mixture is acidified with dilute mineral acids, such as 5% strength hydrochloric acid or sulfuric acid, and extracted with an organic solvent, such as methylene chloride or ethyl acetate. For purification, the extract is extracted with cold 5–10% strength alkali metal carbonate solution, the end product passing over into the aqueous phase. As a result of acidification of the aqueous solution, the product of the formula Ic is precipitated or is extracted again with methylene chloride, dried and then freed from the solvent.

The 1,3-diketones of the formula II which are used as starting material are known and can be prepared by processes known per se (cf. EP-A 71 707, EP-A 142 741, EP-A 243 313, U.S. Pat. No. 4,249,937 and WO 92/13821). Cyclohexane-1,3-dione and dimedon are commercial compounds.

Benzoic acid derivatives of the formula III can be prepared as follows:

Benzoyl halides, for example benzoyl chlorides of the formula III (T=Cl), are prepared in a manner known per se by reacting the benzoic acids of the formula III (T=OH) with thionyl chloride.

The benzoic acids of the formula III (T=OH) can be prepared in a known manner by acidic or basic hydrolysis of the corresponding esters of the formula III (T=$C_1$–$C_4$-alkoxy).

The intermediates of the formula III can be prepared, for example according to schemes 2 and 3, by the methods described below.

Scheme 2

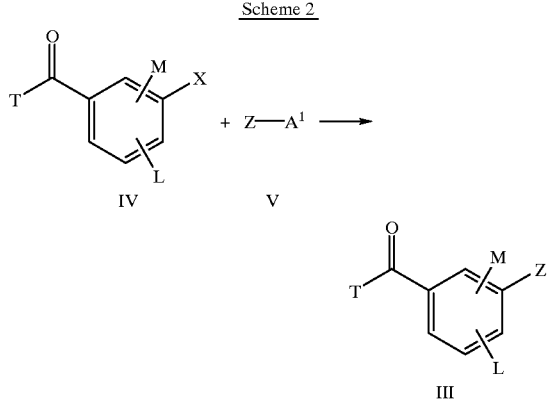

T is $C_1$–$C_4$-alkoxy,
X is Cl, Br, I, —OS(O)$_2$CF$_3$ or —OS(O)$_2$F,
A$^1$ is Sn($C_1$–$C_4$-alkyl)$_3$, B(OH)$_2$ or ZnHal, where Hal is Cl or Br, and
L, M and Z are as defined above.

The arylhalogen compounds or arylsulfonates IV can then be reacted in a manner known per se with hetaryl stannates (Stille coupling reactions), hetaryl-boron compounds (Suzuki coupling reactions) or hetaryl-zinc compounds (Negishi reaction) V (cf. for example Synthesis (1987), 51–53 and Synthesis (1992), 413) in the presence of a palladium or nickel transition metal catalyst and in the presence or absence of a base to give the novel compounds of the general formula III.

The benzoic acid derivatives of the formula III can also be obtained by reacting corresponding bromine- or iodine-substituted compounds of the formula VI Scheme 3

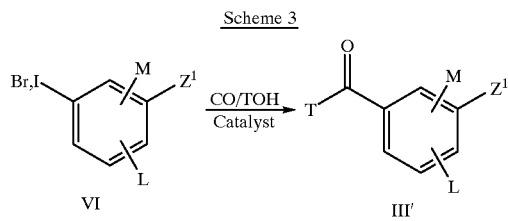

Z$^1$ Z or CN
T OH or $C_1$–$C_4$-alkoxy where L and M have the abovementioned meanings, with carbon monoxide and water under superatmospheric pressure in the presence of a palladium, nickel, cobalt or rhodium transition metal catalyst and of a base.

Benzoyl derivatives of the formula IIIa

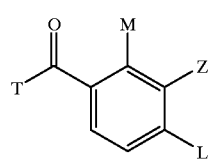

IIIa where
T is chlorine, OH or $C_1$–$C_4$-alkoxy,
L is $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano,
M is $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and is as stated above, are preferred for the purposes of the present invention.

Other preferred benzoyl derivatives are those of the formula IIIb

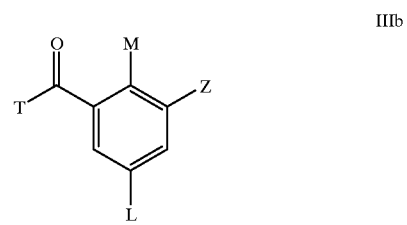

IIIb where
T is chlorine, OH or $C_1$–$C_4$-alkoxy,
L and M are each $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and is as stated above.

The catalysts nickel, cobalt, rhodium and in particular palladium may be present in metallic form or in the form of conventional salts, such as halogen compounds, eg. PdCl$_2$, RhCl$_3$.H$_2$O, acetates, eg. Pd(OAc)$_2$, cyanides, etc., in the known valency states. Furthermore, metal complexes with tertiary phosphines, metal alkyl carbonyls, metal carbonyls, eg. Co$_2$(CO)$_8$ or Ni(CO)$_4$, metal carbonyl complexes with tertiary phosphines, eg. (PPh$_3$)$_2$Ni(CO)$_2$, or transition metal salts complexed with tertiary phosphines may also be present. The last-mentioned embodiment is preferred in particular in the case of palladium as a catalyst. The type of phosphine ligands can be varied within a wide range. For example, they are of the formulae:

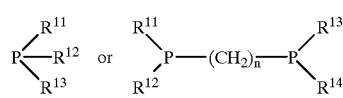

where n is 1, 2, 3, or 4 and $R^{11}$ to $R^{14}$ are each low molecular weight alkyl, for example $C_1$–$C_6$-alkyl, aryl or $C_1$–$C_4$-alkylaryl, eg. benzyl, phenethyl or aryloxy. Aryl is, for example naphthyl, anthryl and preferably unsubstituted or substituted phenyl, and, with regard to the substituents, only their inertness to the carboxylation reaction is important; otherwise, they may be varied within a wide range and comprise all inert C-organic radicals, such as $C_1$–$C_6$-alkyl, eg. methyl, carboxyl, such as COOH, COOM (M is, for example, an alkali metal or alkaline earth metal or ammonium salt) or C-organic radicals bonded via oxygen, such as $C_1$–$C_6$-alkoxy.

The preparation of the phosphine complexes can be carried out in a manner known per se, for example as described in the documents cited at the outset. For example, conventional commercially obtainable metal salts, such as PdCl$_2$ or Pd(OCOCH$_3$)$_2$, are used as starting materials, and the phosphine, eg. P(C$_6$H$_5$)$_3$, P(n-C$_4$H$_9$)$_3$, PCH$_3$(C$_6$H$_5$)$_2$ or 1,2-bis(diphenylphosphino)ethane, is added.

The amount, based on the transition metal, of phosphine is usually from 0 to 20, in particular from 0.1 to 10, particularly preferably from 1 to 5, mol equivalents.

The amount of transition metal is not critical. For cost reasons, it is of course preferable to use a small amount, for example from 0.1 to 10, in particular from 1 to 5, mol %, based on the starting material II or III.

For the preparation of the benzoic acids III (T=OH), the reaction is carried out with carbon monoxide and at least equimolar amounts, based on the starting materials VI, of water. The reactant water may simultaneously serve as the solvent, ie. the maximum amount is not critical.

However, depending on the type of starting materials and on the catalysts used, it may also be advantageous to use, instead of the reactant, another inert solvent or the base used for the carboxylation as a solvent.

Suitable inert solvents for carboxylation reactions are conventional solvents, such as hydrocarbons, eg. toluene, xylene, hexane, pentane or cyclohexane, ethers, eg. methyl tert-butyl ether, tetrahydrofuran, dioxane or dimethoxyethane, substituted amides, such as dimethylformamide, persubstituted ureas, such as tetra-$C_1$–$C_4$-alkylureas, or nitriles, such as benzonitrile or acetonitrile.

In a preferred embodiment of the process, one of the reactants, in particular the base, is used in excess, so that no additional solvent is required.

Bases suitable for the process are all inert bases which are capable of binding the hydrogen iodide or hydrogen bromide liberated in the reaction. Examples of these are tertiary amines, such as tert-alkylamines, for example trialkylamines, such as triethylamine, cyclic amines, such as N-methylpiperidine, N,N'-dimethylpiperazine or pyridine, alkali metal dicarbonates or tetraalkyl-substituted urea derivatives, such as tetra-$C_1$–$C_4$-alkylurea, eg. tetramethylurea.

The amount of base is not critical; usually, from 1 to 10, in particular from 1 to 5, mol are used. When the base is simultaneously used as the solvent, the amount is as a rule such that the reactants are dissolved; for feasibility reasons unnecessarily large excesses are avoided in order to reduce costs, to be able to use small reaction vessels and to ensure maximum contact for the reactants.

During the reaction, the carbon monoxide pressure is adjusted so that there is always an excess, based on VI, of CO. The carbon monoxide pressure at room temperature is preferably from 1 to 250 bar, in particular from 5 to 150, bar.

The carbonylation is carried out as a rule at from 20 to 250° C., preferably from 30 to 150° C., continuously or batchwise. In batchwise operation, carbon monoxide is advantageously forced continuously onto the reaction mixture in order to maintain a constant pressure.

The arylhalogen compounds VI used as starting compounds are known or can be readily prepared by suitable combination of known syntheses.

For example, the halogen compounds VI can be obtained by a Sandmeyer reaction from corresponding anilines, which in turn are synthesized by reduction of suitable nitro compounds (cf. for example for VI where $Z^1$=CN: Liebigs Ann. Chem. (1980), 768–778). The aryl bromides VI may furthermore be obtained by direct bromination of suitable starting compounds [cf. for example Monatsh. Chem. 99 (1968), 815–822].

Scheme 4

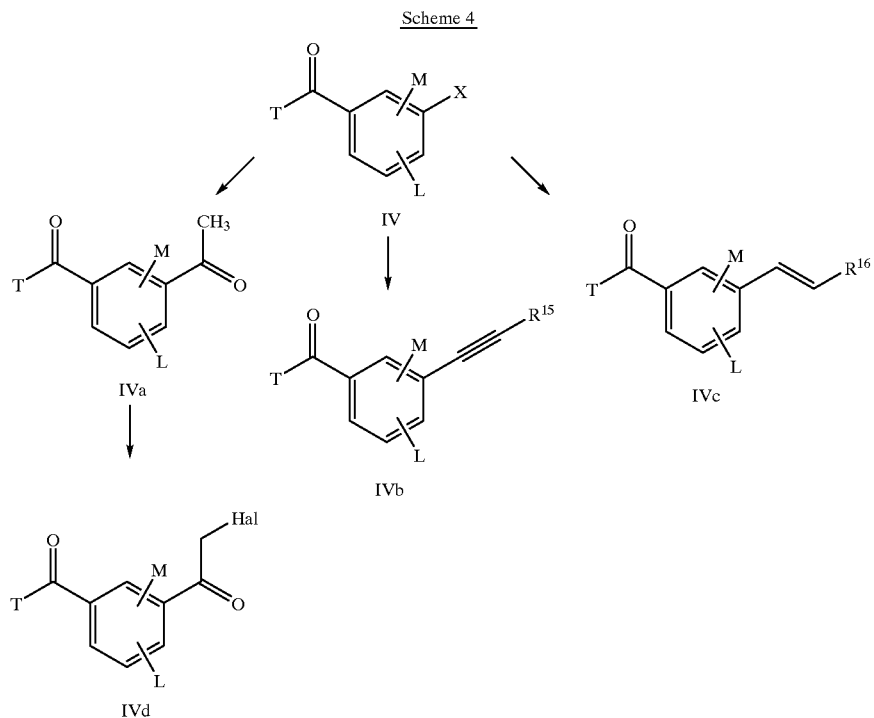

T is $C_1$–$C_4$-alkoxy,

X is Cl, Br, I, —OS(O)$_2$CF$_3$ or —OS(O)$_2$F,

L, M and Z are as defined above, $R^{15}$ is hydrogen, $C_1$–$C_4$-alkyl, $C_1$–$C_4$-haloalkyl, $C_3$–$C_8$-cycloalkyl, unsubstituted or substituted phenyl or trimethylsilyl and $R^{16}$ is hydrogen, $C_1$–$C_4$-haloalkyl, $C_3$–$C_8$-cycloalkyl or unsubstituted or substituted phenyl.

Starting from the arylhalogen compounds or aryl sulfonates IV, aryl methyl ketones IVa can be prepared in the presence of a palladium or nickel transition metal catalyst and in the presence or absence of a base by methods known from the literature, by reaction with vinyl alkyl ethers and subsequent hydrolysis [cf. for example Tetrahedron Lett. 32 (1991), 1753–1756].

The ethynylated aromatics IVb can be prepared in a manner known per se by reacting arylhalogen compounds or aryl sulfonates IV with substituted acetylenes in the presence of a palladium or nickel transition metal catalyst (eg. Heterocycles 24 (1986), 31–32). Derivatives IVb where $R^{15}$ is H are advantageously obtained from silyl compounds IVb where $R^{15}$ is $—Si(CH_3)_3$ [J. Org. Chem. 46 (1981), 2280–2286].

The arylalkenes IVc are obtained by a Heck reaction of arylhalogen compounds or aryl sulfonates IV with olefins in the presence of a palladium catalyst (cf. for example, Heck, Palladium Reagents in Organic Synthesis, Academic Press, London 1985, and Synthesis 1993, 735–762).

The benzoyl derivatives IV used as starting compounds are known [cf. for example Coll. Czech. Chem. Commn. 40 (1975), 3009–3019] or can readily be prepared by suitable combination of known syntheses.

For example, the sulfonates IV (X=$—OS(O)_2CF_3$ or $—OS(O)_2F$) can be obtained from the corresponding phenols, which in turn are known (cf. for example EP 195247) or can be prepared by known methods (cf. for example Synthesis 1993, 735–762).

The halogen compounds IV (X=Cl, Br or I) can be obtained from corresponding anilines, for example by Sandmeyer reaction.

A is S, NH or NOH

T is $C_1$–$C_4$-alkoxy and L and M are as defined above.

Isophthalic acid derivatives IVf can be prepared from the aldehydes IVe by known processes [cf. J. March, Advanced Organic Chemistry 3rd edition, page 629 et seq., Wiley-Interscience Publication (1985)].

The oximes IVg are advantageously obtained by reacting aldehydes IVe with hydroxylamine in a manner known per se [cf. J. March, Advanced Organic Chemistry 3rd edition, pages 805–806, Wiley-Interscience Publication (1985)].

The conversion of the oximes IVg into nitriles IVh can likewise be carried out by processes known per se [cf. J. March, Advanced Organic Chemistry 3rd edition, pages 931–932, Wiley-Interscience Publication (1985)].

The aldehydes IVe required as starting compounds are known or can be prepared by known methods. For example, they can be synthesized according to scheme 6 from the methyl compounds VII.

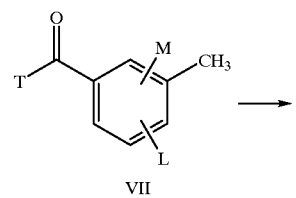

Scheme 6

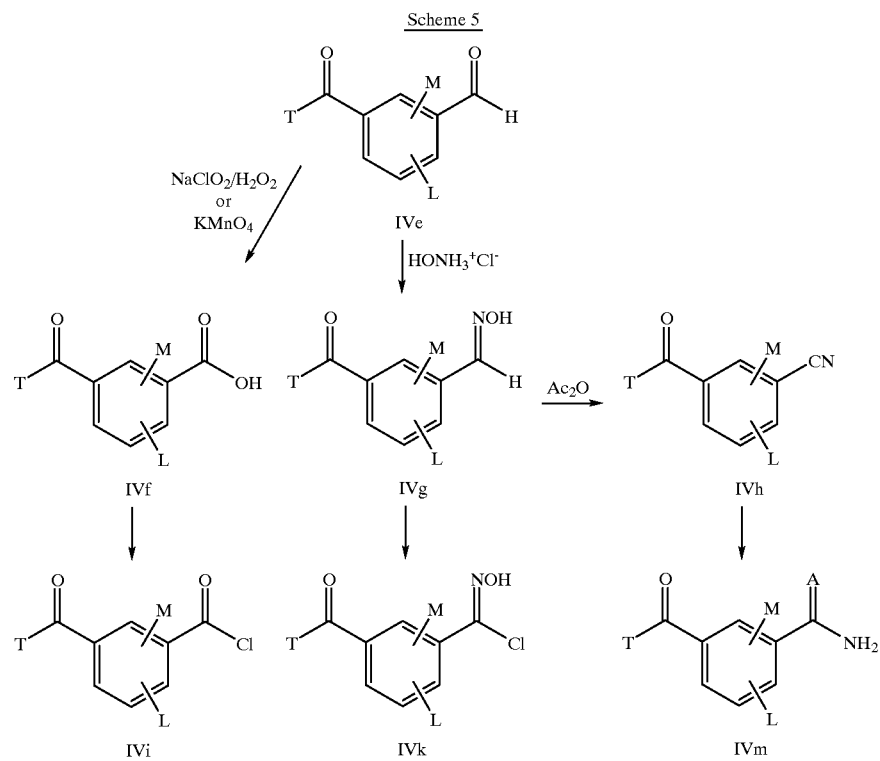

Scheme 5

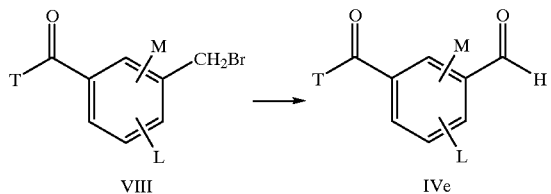

T, M and L have the meanings stated under scheme 5. The methyl compounds VII can be converted by generally known methods, for example with N-bromosuccinimide or 1,3-dibromo-5,5-dimethylhydantoin, into the benzyl bromides VIII. The conversion of benzyl bromides into benzaldehydes IVe is likewise known from the literature [cf. Synth. Commun. 22 (1992), 1967–1971].

The intermediates IVa to IVh are suitable for the synthesis of heterocyclic intermediates III.

For example, 5-oxazolyl derivatives [cf. for example J. Heterocyclic Chem. 28 (1991), 17–28] or 4-thiazolyl derivatives [cf. for example Metzger, Thiazoles in: The Chemistry of heterocyclic compounds, vol. 34, page 175 et seq. (1976)] can be obtained from the acetophenones IVa via the halogenated intermediate IVd.

The acetylenes IVb and the alkenes IVc are suitable for the synthesis of 4-isoxazolyl, 5-isoxazolyl, 4,5-dihydroisoxazol-4-yl and 4,5-dihydroisoxazol-5-yl derivatives [cf. for example Houben-Weyl, Methoden der organischen Chemie, 4th edition, vol. X/3, page 843 et seq. (1965)].

2-Oxazolyl, 1,2,4-oxadiazol-5-yl and 1,3,4-oxadiazol-2-yl derivatives [cf. for example J. Heterocyclic Chem. 28 (1991), 17–28] or 2-pyrrolyl derivatives [cf. for example Heterocycles 26 (1987), 3141–3151] can be prepared by processes known from the literature, from the benzoic acids IVf or the acyl chlorides IVi obtainable therefrom by standard methods.

1,2,4-Triazol-3-yl derivatives can be prepared from benzonitriles IVh by known methods [cf. for example J. Chem. Soc. (1954), 3461–3464].

The benzonitriles IVh can be converted into 1,2,4-oxadiazol-3-yl derivatives [cf. for example J. Heterocyclic Chem. 28 (1991), 17–28] or 2-thiazolyl, 4,5-dihydrothiazol-2-yl or 5,6-dihydro-4H-1,3-thiazin-2-yl derivatives [cf. for example Houben-Weyl, Methoden der organischen Chemie, 4th edition, vol. E5, page 1268 et seq. (1985)] by the intermediate stage of the thioamides, amide-oximes or amidines IVm. By processes known from the literature, thioamides IVm (A=S) can furthermore be converted into 1,2,4-thiadiazol-5-yl derivatives [cf. for example J. Org. Chem. 45 (1980), 3750–3753] or 1,3,4-thiadiazol-2-yl derivatives [cf. for example J. Chem. Soc., Perkin Trans. I (1982), 1987–1991].

The conversion of oximes IVg into 3-isoxazolyl derivatives can be carried out in a manner known per se via the hydroxamyl chloride intermediates IVk [cf. for example Houben-Weyl, Methoden der organischen Chemie, 4th edition, vol. X/3, page 843 et seq. (1965)].

In view of the intended use of the benzoyl derivatives of the general formula I, the radicals below are suitable substituents:

L and M are each hydrogen, $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl or 1-ethyl-2-methyl-propyl, in particular methyl, ethyl, 1-methylethyl, 1-methylpropyl, 2-methylpropyl, 1,1-dimethylethyl or 1,1-dimethylpropyl;

$C_2$–$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3 pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or ethyl-2-methyl-2-propenyl, in particular 1-methyl-2-propenyl, 1-methyl-2-butenyl, 1,1-dimethyl-2-propenyl or 1,1-dimethyl-2-butenyl;

$C_2$–$C_6$-alkynyl such as propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2 propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl;

$C_1$–$C_4$-alkoxy such as methoxy, ethoxy, n-propoxy, 1-methylethoxy, n-butoxy, 1-methylpropoxy, 2-methylpropoxy or 1,1-dimethylethoxy, in particular $C_1$–$C_3$-alkoxy such as methoxy, ethoxy or isopropoxy, where these groups may be unsubstituted or substituted by one to five halogen atoms, such as fluorine, chlorine, bromine or iodine, preferably fluorine or chlorine, or $C_1$–$C_4$-alkoxy as stated above.

The group —$(Y)_n$—$S(O)_m R^7$ defined above is, for example, $C_1$–$C_4$-alkylthio such as methylthio, ethylthio, n-propylthio, 1-methylethylthio, n-butylthio, 1-methylpropylthio 2-methylpropylthio or 1,1-dimethylethylthio, in particular methylthio;

$C_1$–$C_4$-alkylsulfinyl, such as methylsulfinyl, ethylsulfinyl, n-propylsulfinyl, 1-methylethylsulfinyl, n-butylsulfinyl, 1-methylpropylsulfinyl, 2-methylpropylsulfinyl or 1,1-dimethylethylsulfinyl, in particular methylsulfinyl;

$C_1$–$C_4$-alkylsulfonyl such as methylsulfonyl, ethylsulfonyl, n-propylsulfonyl, 1-methylethylsulfonyl n-butylsulfonyl, 1-methylpropylsulfonyl, 2-methylpropylsulfonyl or 1,1-dimethylethylsulfonyl, in particular methylsulfonyl;

$C_1$–$C_4$-alkoxysulfonyl such as methoxysulfonyl, ethoxysulfonyl, n-propoxysulfonyl, 1-methylethoxysulfonyl, n-butoxysulfonyl, 1-methylpropoxysulfonyl, 2-methylpropoxysulfonyl or 1,1-dimethylethoxysulfonyl, in particular methoxysulfonyl;

N—$C_1$–$C_4$-alkylsulfamoyl such as N-methylsulfamoyl, N-ethylsulfamoyl, N-n-propylsulfamoyl, N-1-methylethylsulfamoyl, N-n-butylsulfamoyl, N-1- methylpropylsulfamoyl, N-2-methylpropylsulfamoyl or N-1,1-dimethylethylsulfamoyl, in particular N-methylsulfamoyl;

N—$C_1$–$C_4$-alkylsulfinamoyl such as N-methylsulfinamoyl, N-ethylsulfinamoyl, N-n-propylsulfinamoyl, N-1-methylethylsulfinamoyl, N-n-butylsulfinamoyl, N-1-methylpropylsulfinamoyl, N-2-methylpropylsulfinamoyl or N-1,1-dimethylethylsulfinamoyl, in particular N-methylsulfinamoyl;

Di-$C_1$–$C_4$-alkylsulfamoyl such as dimethylsulfamoyl, diethylsulfamoyl, dipropylsulfamoyl, dibutylsulfamoyl, N-methyl-N-ethylsulfamoyl, N-methyl-N-propylsulfamoyl, N-methyl-N-1-methylethylsulfamoyl, N-methyl-N-1,1-dimethylethylsulfamoyl, di-1-methylethylsulfamoyl, N-ethyl-N-1-methylethylsulfamoyl or N-ethyl-N-1,1-dimethyl ethylsulfamoyl; in particular dimethylsulfamoyl;

di-$C_1$–$C_4$-alkylsulfinamoyl, such as dimethylsulfinamoyl, diethylsulfinamoyl, dipropylsulfinamoyl, dibutylsulfinamoyl, N-methyl-N-ethylsulfinamoyl, N-methyl-N-propylsulfinamoyl, N-methyl-N-1-methylethylsulfinamoyl, N-methyl-N-1,1-dimethylethylsulfinamoyl, di-1-methylethylsulfinamoyl, N-ethyl-N-1-methylethylsulfinamoyl or N-ethyl-N-1,1-dimethyl ethylsulfinamoyl; in particular dimethylsulfinamoyl;

$C_1$–$C_4$-alkylsulfinyloxy, such as methylsulfinyloxy, ethylsulfinyloxy, n-propylsulfinyloxy, 1-methylethylsulfinyloxy, n-butylsulfinyloxy, 1-methylpropylsulfinyloxy, 2-methylpropylsulfinyloxy or 1,1-dimethylethylsulfinyloxy, in particular methylsulfinyloxy;

$C_1$–$C_4$-alkylsulfonyloxy, such as methylsulfonyloxy, ethylsulfonyloxy, n-propylsulfonyloxy, 1-methylethylsulfonyloxy, n-butylsulfonyloxy, 1-methylpropylsulfonyloxy, 2-methylpropylsulfonyloxy or 1,1-dimethylethylsulfonyloxy, in particular methylsulfonyloxy;

$C_1$–$C_4$-alkylsulfinylamino, such as methylsulfinylamino, ethylsulfinylamino, n-propylsulfinylamino, 1-methylethylsulfinylamino, n-butylsulfinylamino, 1-methylpropylsulfinylamino, 2-methylpropylsulfinylamino or 1,1-dimethylethylsulfinylamino, in particular methylsulfinylamino;

$C_1$–$C_4$-alkylsulfonylamino, such as methylsulfonylamino, ethylsulfonylamino, n-propylsulfonylamino, 1-methylethylsulfonylamino, n-butylsulfonylamino, 1-methylpropylsulfonylamino, 2-methylpropylsulfonylamino or 1,1-dimethylethylsulfonylamino, in particular methylsulfonylamino;

N—$C_1$–$C_4$-alkylsulfinyl-N-methylamino, such as N-methylsulfinyl-N-methylamino, N-ethylsulfinyl-N-methylamino, N-n-propylsulfinyl-N-methylamino, N-1-methylethylsulfinyl-N-methylamino, N-n-butylsulfinyl-N-methylamino, N-1-methylpropylsulfinyl-N-methylamino, N-2-methylpropylsulfinyl-N-methylamino or N-1,1-dimethylethylsulfinyl-N-methylamino, in particular N-methylsulfinyl-N-methylamino;

N—$C_1$–$C_4$-alkylsulfinyl-N-ethylamino, such as N-methylsulfinyl-N-ethylamino, N-ethylsulfinyl-N-ethylamino, N-n-propylsulfinyl-N-ethylamino, N-1-methylethylsulfinyl-N-ethylamino, N-n-butylsulfinyl-N-ethylamino, N-1-methylpropylsulfinyl-N-ethylamino, N-2-methylpropylsulfinyl-N-ethylamino or N-1,1-dimethylethylsulfinyl-N-ethylamino, in particular N-methylsulfinyl-N-ethylamino;

N—$C_1$–$C_4$-alkylsulfonyl-N-methylamino, such as N-methylsulfonyl-N-methylamino, N-ethylsulfonyl-N-methylamino, N-n-propylsulfonyl-N-methylamino, N-1-methylethylsulfonyl-N-methylamino, N-n-butylsulfonyl-N-methylamino, N-1-methylpropylsulfonyl-N-methylamino, N-2-methylpropylsulfonyl-N-methylamino or N-1,1-dimethylethylsulfonyl-N-methylamino, in particular N-methylsulfonyl-N-methylamino;

N—$C_1$–$C_4$-alkylsulfonyl-N-ethylamino, such as N-methylsulfonyl-N-ethylamino, N-ethylsulfonyl-N-ethylamino, N-n-propylsulfonyl-N-ethylamino, N-1-methylethylsulfonyl-N-ethylamino, N-n-butylsulfonyl-N-ethylamino, N-1-methylpropylsulfonyl-N-ethylamino, N-2-methylpropylsulfonyl-N-ethylamino or N-1,1-dimethylethylsulfonyl-N-ethylamino, in particular N-methylsulfonyl-N-ethylamino;

$C_1$–$C_4$-haloalkylthio, such as chloromethylthio, dichloromethylthio, trichloromethylthio, fluoromethylthio, difluoromethylthio, trifluoromethylthio, chlorofluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio or pentafluoroethylthio, in particular trifluoromethylthio.

The group —$(Y)_n$—CO—$R^8$ defined above is, for example, $C_1$–$C_4$-alkylcarbonyl, such as methylcarbonyl, ethylcarbonyl, n-propylcarbonyl, 1-methylethylcarbonyl, n-butylcarbonyl, 1-methylpropylcarbonyl, 2-methylpropylcarbonyl or 1,1-dimethylethylcarbonyl, in particular methylcarbonyl;

$C_1$–$C_4$-alkoxycarbonyl, such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl, in particular methoxycarbonyl;

N—$C_1$–$C_4$-alkylcarbamoyl, such as N-methylcarbamoyl, N-ethylcarbamoyl, N-n-propylcarbamoyl, N-1-methylethylcarbamoyl, N-n-butylcarbamoyl, N-1-methylpropylcarbamoyl, N-2-methylpropylcarbamoyl or N-1,1-dimethylethylcarbamoyl, in particular N-methylcarbamoyl;

Di-$C_1$–$C_4$-alkylcarbamoyl, such as dimethylcarbamoyl, diethylcarbamoyl, dipropylcarbamoyl, dibutylcarbamoyl, N-methyl-N-ethylcarbamoyl, N-methyl-N-propylcarbamoyl, N-methyl-N-1-methylethylcarbamoyl, N-methyl-N-1,1-dimethylethylcarbamoyl, di-1-methylethylcarbamoyl, N-ethyl-N-1-methylethylcarbamoyl or N-ethyl-N-1,1-dimethyl ethylcarbamoyl; in particular dimethylcarbamoyl;

$C_1$–$C_4$-alkylcarbonyloxy, such as methylcarbonyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy or 1,1-dimethylethylcarbonyloxy, in particular methylcarbonyloxy;

$C_1$–$C_4$-alkylcarbonylamino, such as methylcarbonylamino, ethylcarbonylamino, n-propylcarbonylamino, 1-methylethylcarbonylamino, n-butylcarbonylamino, 1-methylpropylcarbonylamino, 2-methylpropylcarbonylamino or 1,1-dimethylethylcarbonylamino, in particular methylcarbonylamino;

N—$C_1$–$C_4$-alkylcarbonyl-N-methylamino, such as N-methylcarbonyl-N-methylamino, N-ethylcarbonyl-N-methylamino, N-n-propylcarbonyl-N-methylamino, N-1-methylethylcarbonyl-N-methylamino, N-n-butylcarbonyl-N-methylamino, N-1-methylpropylcarbonyl-N- methylamino, N-2-methylpropylcarbonyl-N-methylamino or N-1,1-dimethylethylcarbonyl-N-methylamino, in particular N-methylcarbonyl-N-methylamino.

Z is, for example:

a 5-membered or 6-membered heterocyclic, saturated or unsaturated radical containing from one to three hetero atoms selected from the group consisting of oxygen, sulfur and nitrogen, for example a heteroaromatic having a 5-membered ring, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl, 1,2,4-triazol-3-yl, 1,3,4-triazol-2-yl, 1,2,3-triazol-4-yl, 1,2,3-triazol-5-yl, 1,2,4-triazol-5-yl or tetrazol-5-yl, in particular 2-thiazolyl or 3-isoxazolyl;

a heteroaromatic having a six-membered ring, such as 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-5-yl, 1,2,4-triazin-3-yl, 1,2,4-triazin-6-yl or 1,2,4,5-tetrazin-3-yl;

5-membered or 6-membered, saturated or partially unsaturated heterocycles containing from one to three nitrogen atoms and/or one or two oxygen or sulfur atoms, such as 2-tetrahydrofuranyl, 3-tetrahydrofuranyl, 2-tetrahydrothienyl, 3-tetrahydrothienyl, tetrahydrothiopyran-2-yl, tetrahydrothiopyran-3-yl, tetrahydrothiopyran-4-yl, 1,3-dithiolan-2-yl, 1,3-dithiolan-4-yl, 1-3-dithian-2-yl, 1,3-dithian-4-yl, 5,6-dihydro-4H-1,3-thiazin-2-yl, 1,3-oxathiolan-2-yl, 1,3-oxathian-2-yl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 1,3-dioxolan-2-yl, 1,3-dioxolan-4-yl, 1,3-dioxan-5-yl, 1,4-dioxan-2-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl or 1,2,4-tetrahydrotriazin-3-yl, in particular 2-tetrahydrofuranyl, 1,3-dioxolan-2-yl or 1,3-dioxan-2-yl, which is substituted or substituted by halogen as stated above, in particular fluorine or chlorine, cyano, nitro, a group —COR$^8$, for example alkylcarbonyl as stated above, alkoxycarbonyl as stated above, N-alkylcarbamoyl as stated above, dialkylcarbamoyl as stated above;

$C_1$–$C_4$-alkyl as stated above, $C_1$–$C_4$-haloalkyl, for example chloromethyl, difluoromethyl, dichloromethyl, trifluoromethyl, trichloromethyl, chlorodifluoromethyl, 1-fluoroethyl, 2-fluoroethyl, 2,2-difluoroethyl, 1,1,2,2-tetrafluoroethyl, 2,2,2-trifluoroethyl, 2-chloro-1,1,2-trifluoroethyl, pentafluoroethyl, decafluorobutyl or 1,1-bistrifluoromethyl-2,2,2-trifluoroethyl, preferably difluoromethyl, trifluoromethyl, trichloromethyl or chlorodifluoromethyl;

$C_3$–$C_8$-cycloalkyl, for example cyclopropyl, cyclobutyl, cyclopentyl, cyclohexyl, cycloheptyl or cyclooctyl, in particular cyclopropyl or cyclohexyl;

$C_1$–$C_4$-alkoxy as stated above, $C_1$–$C_4$-haloalkoxy, for example chloromethoxy, dichloromethoxy, trichloromethoxy, fluoromethoxy, difluoromethoxy, trifluoromethoxy, chlorodifluoromethoxy, dichlorofluoromethoxy, 1-fluoromethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular $C_1$–$C_3$-haloalkoxy, such as 2,2,2-trifluoroethoxy or 2-chloro-2,2-difluoroethoxy;

$C_1$–$C_4$-alkylthio as stated above, $C_1$–$C_4$-haloalkylthio as stated above, di-$C_1$–$C_4$-alkylamino, for example dimethylamino, diethylamino, dipropylamino, dibutylamino, N-methyl-N-ethylamino, N-methyl-N-propylamino, N-methyl-N-1-methylethylamino, N-methyl-N-1,1-dimethylethylamino, di-1-methylethylamino, N-ethyl-N-1-methylethylamino or N-ethyl-N-1,1-dimethylethylamino;

unsubstituted or substitued phenyl or an oxo group which may also be present in tautomeric form as a hydroxyl group, for example thiazolin-4,5-dion-2-yl, 3-oxo-3H-1,2,4-dithiazolyl or 2-oxo-2H-1,3,4-dithiazolyl.

Benzofused heteroaromatics having a 5-membered or 6-membered ring are, for example, benzofuranyl, benzothienyl, indolyl, benzoxazolyl, benzisoxazolyl, benzthiazolyl, benzisothiazolyl, benzpyrazolyl, indazolyl, 1,2,3-benzothiadiazolyl, 2,1,3-benzothiadiazolyl, benzotriazolyl, benzofuroxanyl, quinolyl, isoquinolyl, cinnolyl, quinazolyl, quinoxalyl or phthalazyl. Examples of particularly preferred compounds of the general formula I are listed in Tables 1 to 5 below.

TABLE 1

Compounds of the structure Id

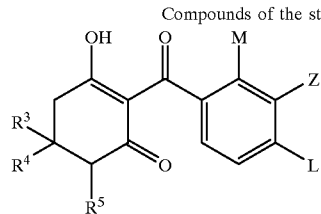

| No. | R³ | R⁴ | R⁵ | L | M | Z |
|---|---|---|---|---|---|---|
| 1.12 | H | H | H | SO₂CH₃ | Cl | 2-Thienyl |
| 1.13 | H | H | H | SO₂CH₃ | Cl | 3-Thienyl |
| 1.14 | H | H | H | SO₂CH₃ | Cl | 2-Furyl |
| 1.15 | H | H | H | SO₂CH₃ | Cl | 3-Furyl |
| 1.16 | H | H | H | SO₂CH₃ | Cl | 3-Methyl-isoxazol-5-yl |
| 1.17 | H | H | H | SO₂CH₃ | Cl | 5-Thiazolyl |
| 1.18 | H | H | H | SO₂CH₃ | Cl | 4-Thiazolyl |
| 1.19 | H | H | H | SO₂CH₃ | Cl | 2-Thiazolyl |
| 1.20 | H | H | H | SO₂CH₃ | Cl | 3-Methyl-isothiazol-5-yl |
| 1.21 | H | H | H | SO₂CH₃ | Cl | 3-Isoxazolyl |
| 1.22 | H | H | H | SO₂CH₃ | Cl | 5-Phenyl-thiazol-2-yl |
| 1.23 | H | H | H | SO₂CH₃ | Cl | 2-Pyridyl |
| 1.24 | H | H | H | SO₂CH₃ | Cl | 3-Pyridyl |
| 1.25 | H | H | H | SO₂CH₃ | Cl | 4-Pyridyl |
| 1.26 | H | H | H | SO₂CH₃ | Cl | 1-Methyl-2-pyrrolyl |
| 1.27 | H | H | H | SO₂CH₃ | Cl | 1-Methyl-1,2,4-triazol-5-yl |
| 1.28 | H | H | H | SO₂CH₃ | Cl | 2-Benzthiazolyl |
| 1.29 | H | H | H | SO₂CH₃ | Cl | 2-Quinolyl |
| 1.30 | H | H | H | SO₂CH₃ | Cl | 1-Methylbenzimidazol-2-yl |
| 1.31 | H | H | H | SO₂CH₃ | Cl | 2-Oxazolyl |
| 1.32 | H | H | H | SO₂CH₃ | Cl | 1-Phenyl-pyrazol-5-yl |
| 1.33 | H | H | H | SO₂CH₃ | Cl | 1-Methyl-pyrazol-3-yl |
| 1.34 | H | H | H | SO₂CH₃ | Cl | 1-Methyl-pyrazol-5-yl |
| 1.35 | H | H | H | SO₂CH₃ | Cl | 1,3-Dimethylpyrazol-3-yl |
| 1.36 | H | H | H | SO₂CH₃ | Cl | 1-Phenyl-pyrazol-3-yl |
| 1.37 | H | H | H | SO₂CH₃ | Cl | 1,4-Dimethylpyrazol-5-yl |
| 1.38 | H | H | H | SO₂CH₃ | Cl | 1,3-Dimethylpyrazol-4-yl |
| 1.39 | H | H | H | SO₂CH₃ | Cl | 1,5-Dimethylpyrazol-4-yl |
| 1.40 | H | H | H | SO₂CH₃ | Cl | 1-Methyl-pyrazol-4-yl |
| 1.41 | H | H | H | SO₂CH₃ | Cl | 1,3-Dimethylpyrazol-5-yl |
| 1.42 | H | H | H | SO₂CH₃ | Cl | 4-Methyl-oxazol-2-yl |
| 1.43 | H | H | H | SO₂CH₃ | Cl | 5-Methylthio-thiazol-2-yl |
| 1.44 | H | H | H | SO₂CH₃ | Cl | 4-Methoxy-1-methylpyrazol-5-yl |
| 1.45 | H | H | H | SO₂CH₃ | Cl | 3-Cyclopropylisoxazol-5-yl |
| 1.46 | H | H | H | SO₂CH₃ | Cl | 3-Isopropylisoxazol-5-yl |
| 1.47 | H | H | H | SO₂CH₃ | Cl | (3-Methyl-phenyl)-thiazol-2-yl |
| 1.48 | H | H | H | SO₂CH₃ | Cl | 5-Methyl-thiazol-2-yl |
| 1.49 | H | H | H | SO₂CH₃ | Cl | 4-Bromo-2-thienyl |
| 1.50 | H | H | H | SO₂CH₃ | Cl | 5-Methyl-2-thienyl |
| 1.51 | H | H | H | SO₂CH₃ | Cl | 4-Methyl-2-thienyl. |
| 1.52 | H | H | H | SO₂CH₃ | Cl | 4-Methyl-thiazol-2-yl |
| 1.53 | H | H | H | SO₂CH₃ | Cl | 4-Chloro-thiazol-2-yl |
| 1.54 | H | H | H | SO₂CH₃ | Cl | 4,5-Dimethylthiazol-2-yl |
| 1.55 | H | H | H | SO₂CH₃ | Cl | 4-Phenyl-thiazol-2-yl |
| 1.56 | H | H | H | SO₂CH₃ | Cl | 2-Methoxy-thiazol-5-yl |
| 1.57 | H | H | H | SO₂CH₃ | Cl | 4-Methyl-2-pyridyl |
| 1.58 | H | H | H | SO₂CH₃ | Cl | 6-(2-Methoxyethyl)-2-pyridyl |
| 1.59 | H | H | H | SO₂CH₃ | Cl | 6-Methylthio-2-pyridyl |
| 1.60 | H | H | H | SO₂CH₃ | Cl | 6-Methoxy-3-pyridyl |
| 1.61 | H | H | H | SO₂CH₃ | Cl | 6-Methoxy-2-pyridyl |
| 1.62 | H | H | H | SO₂CH₃ | Cl | 6-Methyl-2-pyridyl |
| 1.63 | H | H | H | SO₂CH₃ | Cl | 6-(2,2,2-Trifluoroethoxy)-2-pyridyl |
| 1.64 | H | H | H | SO₂CH₃ | Cl | 6-(2,2,2-Trifluoroethoxy)-3-pyridyl |
| 1.65 | H | H | H | SO₂CH₃ | Cl | 5-Pyrimidinyl |
| 1.66 | H | H | H | SO₂CH₃ | Cl | 6-Dimethylamino-3-pyridyl |
| 1.67 | H | H | H | SO₂CH₃ | Cl | 1,2,4-Thiadiazol-5-yl |
| 1.68 | H | H | H | SO₂CH₃ | Cl | 3-Ethoxycarbonyl-1-methyl-pyrazol-5-yl |
| 1.69 | H | H | H | SO₂CH₃ | Cl | 2-Methylthio-pyrimidin-5-yl |
| 1.70 | H | H | H | SO₂CH₃ | Cl | 2-Pyrimidinyl |
| 1.71 | H | H | H | SO₂CH₃ | Cl | 2-Methylthio-pyrimidin-4-yl |
| 1.72 | H | H | H | SO₂CH₃ | Cl | 5-Methylthio-1,3,4-thiadiazol-2-yl |
| 1.73 | H | H | H | SO₂CH₃ | Cl | 5-Methoxy-1,3,4-thiadiazol-2-yl |
| 1.74 | H | H | H | SO₂CH₃ | Cl | 4,5-Dihydro-thiazol-2-yl |
| 1.75 | H | H | H | SO₂CH₃ | Cl | 5-Methyl-oxazol-2-yl |
| 1.76 | H | H | H | SO₂CH₃ | Cl | 5-Phenyl-oxazol-2-yl |

TABLE 1-continued

Compounds of the structure Id

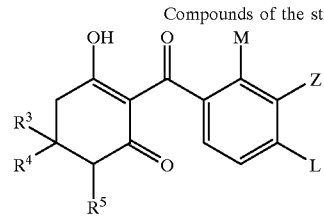

| No. | R³ | R⁴ | R⁵ | L | M | Z |
|---|---|---|---|---|---|---|
| 1.77 | H | H | H | SO₂CH₃ | Cl | 2-Methyl-oxazol-5-yl |
| 1.78 | H | H | H | SO₂CH₃ | Cl | 2-Phenyl-oxazol-5-yl |
| 1.79 | H | H | H | SO₂CH₃ | Cl | 2-Methyl-1,3,4-oxadiazol-5-yl |
| 1.80 | H | H | H | SO₂CH₃ | Cl | 2-Phenyl-1,3,4-oxadiazol-5-yl |
| 1.81 | H | H | H | SO₂CH₃ | Cl | 5-Trifluoromethyl-1,2,4-oxadiazol-3-yl |
| 1.82 | H | H | H | SO₂CH₃ | Cl | 5-Methyl-1,2,4-oxadiazol-3-yl |
| 1.83 | H | H | H | SO₂CH₃ | Cl | 5-Phenyl-1,2,4-oxadiazol-3-yl |
| 1.84 | H | H | H | SO₂CH₃ | Cl | 5-Phenyl-isoxazol-3-yl |
| 1.85 | H | H | H | SO₂CH₃ | Cl | 1-(4-Chlorophenyl)-1,2,4-triazol-2-yl |
| 1.86 | H | H | H | SO₂CH₃ | Cl | 5-Cyano-4,5-dihydro-isoxazol-3-yl |
| 1.87 | H | H | H | SO₂CH₃ | Cl | 5,6-Dihydro-4H-1,3-thiazin-2-yl |
| 1.88 | H | H | H | SO₂CH₃ | Cl | 1,3-Dithiolan-2-yl |
| 1.89 | H | H | H | SO₂CH₃ | Cl | 1,3-Dioxolan-2-yl |
| 1.90 | H | H | H | SO₂CH₃ | Cl | 1,3-Dithian-2-yl |
| 1.91 | H | H | H | SO₂CH₃ | Cl | 1,3-Dioxan-2-yl |
| 1.92 | H | H | H | SO₂CH₃ | Cl | 1,3-Oxathiolan-2-yl |
| 1.93 | H | H | H | SO₂CH₃ | Cl | 1,2,4-Triazol-1-yl |
| 1.94 | H | H | H | SO₂CH₃ | Cl | 3-Methyl-1,2,4-thiadiazol-5-yl |
| 1.95 | H | H | H | SO₂CH₃ | Cl | 1,2,4-Thiadiazol-5-yl |
| 1.96 | H | H | H | SO₂CH₃ | Cl | Thiazoline-4,5-dion-2-yl |
| 1.97 | H | H | H | SO₂CH₃ | Cl | 3-oxo-3-H-1,2,4-dithiazol-5-yl |
| 1.98 | H | H | H | SO₂CH₃ | Cl | 2-oxo-2-H-1,3,4-dithiazol-5-yl |
| 1.99 | H | H | H | NO₂ | H | 1-Pyrrolyl |
| 1.100 | H | H | H | SO₂CH₃ | Cl | 1-Pyrrolyl |
| 1.101 | H | H | H | SO₂CH₃ | H | 1-Pyrrolyl |
| 1.102 | H | H | H | NO₂ | H | 3,5-Dimethyl-pyrazol-1-yl |
| 1.103 | W | H | H | NO₂ | Cl | 2-Thienyl |
| 1.104 | H | H | H | NO₂ | Cl | 3-Thienyl |
| 1.105 | H | H | H | NO₂ | Cl | 2-Furyl |
| 1.106 | H | H | H | NO₂ | Cl | 3-Furyl |
| 1.107 | H | H | H | NO₂ | Cl | 3-Methyl-isoxazol-5-yl |
| 1.108 | H | H | H | NO₂ | Cl | 5-Thiazolyl |
| 1.109 | H | H | H | NO₂ | Cl | 4-Thiazolyl |
| 1.110 | H | H | H | NO₂ | Cl | 2-Thiazolyl |
| 1.111 | H | H | H | NO₂ | Cl | 3-Methyl-isothiazol-5-yl |
| 1.112 | H | H | H | NO₂ | Cl | 3-Isoxazolyl |
| 1.113 | H | H | H | NO₂ | Cl | 5-Phenyl-thiazol-2-yl |
| 1.114 | H | H | H | NO₂ | Cl | 2-Pyridyl |
| 1.115 | H | H | H | NO₂ | Cl | 3-Pyridyl |
| 1.116 | H | H | H | NO₂ | Cl | 4-Pyridyl |
| 1.117 | H | H | H | NO₂ | Cl | 1-Methyl-2-pyrrolyl |
| 1.118 | H | H | H | NO₂ | Cl | 1-Methyl-1,2,4-triazol-5-yl |
| 1.119 | H | H | H | NO₂ | Cl | 2-Benzthiazolyl |
| 1.120 | H | H | H | NO₂ | Cl | 2-Quinolyl |
| 1.121 | H | H | H | NO₂ | Cl | 1-Methyl-benzimidazol-2-yl |
| 1.122 | H | H | H | NO₂ | Cl | 2-oxazolyl |
| 1.123 | H | H | H | NO₂ | Cl | 1-Phenyl-pyrazol-5-yl |
| 1.124 | H | H | H | NO₂ | Cl | 1-Methyl-pyrazol-3-yl |
| 1.125 | H | H | H | NO₂ | Cl | 1-Methyl-pyrazol-5-yl |
| 1.126 | H | H | H | NO₂ | Cl | 1,3-Dimethyl-pyrazol-3-yl |
| 1.127 | H | H | H | NO₂ | Cl | 1-Phenyl-pyrazol-3-yl |
| 1.128 | H | H | H | NO₂ | Cl | 1,4-Dimethyl-pyrazol-5-yl |
| 1.129 | H | H | H | NO₂ | Cl | 1,3-Dimethyl-pyrazol-4-yl |
| 1.130 | H | H | H | NO₂ | Cl | 1,5-Dimethyl-pyrazol-4-yl |
| 1.131 | H | H | H | NO₂ | Cl | 1-Methyl-pyrazol-4-yl |
| 1.132 | H | H | H | NO₂ | Cl | 1,3-Dimethyl-pyrazol-5-yl |
| 1.133 | H | H | H | NO₂ | Cl | 4-Methyl-oxazol-2-yl |
| 1.134 | H | H | H | NO₂ | Cl | 5-Methylthio-thiazol-2-yl |
| 1.135 | H | H | H | NO₂ | Cl | 4-Methoxy-1-methyl-pyrazol-5-yl |
| 1.136 | H | H | H | NO₂ | Cl | 3-Cyclopropyl-isoxazol-5-yl |
| 1.137 | H | H | H | NO₂ | Cl | 3-Isopropyl-isoxazol-5-yl |
| 1.138 | H | H | H | NO₂ | Cl | (3-Methyl-phenyl)-thiazol-2-yl |
| 1.139 | H | H | H | NO₂ | Cl | 5-Methyl-thiazol-2-yl |
| 1.140 | H | H | H | NO₂ | Cl | 4-Bromo-2-thienyl |
| 1.141 | H | H | H | NO₂ | Cl | 5-Methyl-2-thienyl |

TABLE 1-continued

Compounds of the structure Id

| No. | R³ | R⁴ | R⁵ | L | M | Z |
|---|---|---|---|---|---|---|
| 1.142 | H | H | H | NO₂ | Cl | 4-Methyl-2-thienyl |
| 1.143 | H | H | H | NO₂ | Cl | 4-Methyl-thiazol-2-yl |
| 1.144 | H | H | H | NO₂ | Cl | 4-Chloro-thiazol-2-yl |
| 1.145 | H | H | H | NO₂ | Cl | 4,5-Dimethyl-thiazol-2-yl |
| 1.146 | H | H | H | NO₂ | Cl | 4-Phenyl-thiazol-2-yl |
| 1.147 | H | H | H | NO₂ | Cl | 2-Methoxy-thiazol-5-yl |
| 1.148 | H | H | H | NO₂ | Cl | 4-Methyl-2-pyridyl |
| 1.149 | H | H | H | NO₂ | Cl | 6-(2-Methoxyethyl)-2-pyridyl |
| 1.150 | H | H | H | NO₂ | Cl | 6-Methylthio-2-pyridyl |
| 1.151 | H | H | H | NO₂ | Cl | 6-Methoxy-3-pyridyl |
| 1.152 | H | H | H | NO₂ | Cl | 6-Methoxy-2-pyridyl |
| 1.153 | H | H | H | NO₂ | Cl | 6-Methyl-2-pyridyl |
| 1.154 | H | H | H | NO₂ | Cl | 6-(2,2,2-Trifluoroethoxy)-2-pyridyl |
| 1.155 | H | H | H | NO₂ | Cl | 6-(2,2,2-Trifluoroethoxy)-3-pyridyl |
| 1.156 | H | H | H | NO₂ | Cl | 5-Pyrimidinyl |
| 1.157 | H | H | H | NO₂ | Cl | 6-Dimethylamino-3-pyridyl |
| 1.158 | H | H | H | NO₂ | Cl | 1,2,4-Thiadiazol-5-yl |
| 1.159 | H | H | H | NO₂ | Cl | 3-Ethoxycarbonyl-1-methyl-pyrazol-5-yl |
| 1.160 | H | H | H | NO₂ | Cl | 2-Methylthio-pyrimidin-5-yl |
| 1.161 | H | H | H | NO₂ | Cl | 2-Pyrimidinyl |
| 1.162 | H | H | H | NO₂ | Cl | 2-Methylthio-pyrimidin-4-yl |
| 1.163 | H | H | H | NO₂ | Cl | 5-Methylthio-1,3,4-thiadiazol-2-yl |
| 1.164 | H | H | H | NO₂ | Cl | 5-Methoxy-1,3,4-thiadiazol-2-yl |
| 1.165 | H | H | H | NO₂ | Cl | 4,5-Dihydro-thiazol-2-yl |
| 1.166 | H | H | H | NO₂ | Cl | 5-Methyl-oxazol-2-yl |
| 1.167 | H | H | H | NO₂ | Cl | 5-Phenyl-oxazol-2-yl |
| 1.168 | H | H | H | NO₂ | Cl | 2-Methyl-oxazol-5-yl |
| 1.169 | H | H | H | NO₂ | Cl | 2-Phenyl-oxazol-5-yl |
| 1.170 | H | H | H | NO₂ | Cl | 2-Methyl-1,3,4-oxadiazol-5-yl |
| 1.171 | H | H | H | NO₂ | Cl | 2-Phenyl-1,3,4-oxadiazol-5-yl |
| 1.172 | H | H | H | NO₂ | Cl | 5-Trifluoromethyl-1,2,4-oxadiazol-3-yl |
| 1.173 | H | H | H | NO₂ | Cl | 5-Methyl-1,2,4-oxadiazol-3-yl |
| 1.174 | H | H | H | NO₂ | Cl | 5-Phenyl-1,2,4-oxadiazol-3-yl |
| 1.175 | H | H | H | NO₂ | Cl | 5-Phenyl-isoxazol-3-yl |
| 1.176 | H | H | H | NO₂ | Cl | 1-(4-Chlorophenyl)-1,2,4-triazol-2-yl |
| 1.177 | H | H | H | NO₂ | Cl | 5-Cyano-4,5-dihydro-isoxazol-3-yl |
| 1.178 | H | H | H | NO₂ | Cl | 5,6-Dihydro-4H-1,3-thiazin-2-yl |
| 1.179 | H | H | H | NO₂ | Cl | 1,3-Dithiolan-2-yl |
| 1.180 | H | H | H | NO₂ | Cl | 1,3-Dioxolan-2yl |
| 1.181 | H | H | H | NO₂ | Cl | 1,3-Dithian-2-yl |
| 1.182 | H | H | H | NO₂ | Cl | 1,3-Dioxan-2-yl |
| 1.183 | H | H | H | NO₂ | Cl | 1,3-Oxathiolan-2-yl |
| 1.184 | H | H | H | NO₂ | Cl | 1,2,4-Triazol-1-yl |
| 1.185 | H | H | H | NO₂ | Cl | 3-Methyl-1,2,4-thiadiazol-5-yl |
| 1.186 | H | H | H | NO₂ | Cl | 1,2,4-Thiadiazol-5-yl |
| 1.187 | H | H | H | NO₂ | Cl | Thiazoline-4,5-dion-2-yl |
| 1.188 | H | H | H | NO₂ | Cl | 3-oxo-3-H-1,2,4-dithiazol-5-yl |
| 1.189 | H | H | H | NO₂ | Cl | 2-oxo-2-H-1,3,4-dithiazol-5-yl |
| 1.190 | H | H | H | Cl | Cl | 2-Thienyl |
| 1.191 | H | H | H | Cl | Cl | 3-Thienyl |
| 1.192 | H | H | H | Cl | Cl | 2-Furyl |
| 1.193 | H | H | H | Cl | Cl | 3-Furyl |
| 1.194 | H | H | H | Cl | Cl | 3-Methyl-isoxazol-5-yl |
| 1.195 | H | H | H | Cl | Cl | 5-Thiazolyl |
| 1.196 | H | H | H | Cl | Cl | 4-Thiazolyl |
| 1.197 | H | H | H | Cl | Cl | 2-Thiazolyl |
| 1.198 | H | H | H | Cl | Cl | 3-Methyl-isothiazol-5-yl |
| 1.199 | H | H | H | Cl | Cl | 3-Isoxazolyl |
| 1.200 | H | H | H | Cl | Cl | 5-Phenyl-thiazol-2-yl |
| 1.201 | H | H | H | Cl | Cl | 2-Pyridyl |
| 1.202 | H | H | H | Cl | Cl | 3-Pyridyl |
| 1.203 | H | H | H | Cl | Cl | 4-Pyridyl |
| 1.204 | H | H | H | Cl | Cl | 1-Methyl-2-pyrrolyl |
| 1.205 | H | H | H | Cl | Cl | 1-Methyl-1,2,4-triazol-5-yl |
| 1.206 | H | H | H | Cl | Cl | 2-Benzthiazolyl |

TABLE 1-continued

Compounds of the structure Id

Id

| No.   | R³ | R⁴ | R⁵ | L  | M  | Z |
|-------|----|----|----|----|----|---|
| 1.207 | H  | H  | H  | Cl | Cl | 2-Quinolyl |
| 1.208 | H  | H  | H  | Cl | Cl | 1-Methyl-benzimidazol-2-yl |
| 1.209 | H  | H  | H  | Cl | Cl | 2-oxazolyl |
| 1.210 | H  | H  | H  | Cl | Cl | 1-Phenyl-pyrazol-5-yl |
| 1.211 | H  | H  | H  | Cl | Cl | 1-Methyl-pyrazol-3-yl |
| 1.212 | H  | H  | H  | Cl | Cl | 1-Methyl-pyrazol-5-yl |
| 1.213 | H  | H  | H  | Cl | Cl | 1,3-Dimethyl-pyrazol-3-yl |
| 1.214 | H  | H  | H  | Cl | Cl | 1-Phenyl-pyrazol-3-yl |
| 1.215 | H  | H  | H  | Cl | Cl | 1,4-Dimethyl-pyrazol-5-yl |
| 1.216 | H  | H  | H  | Cl | Cl | 1,3-Dimethyl-pyrazol-4-yl |
| 1.217 | H  | H  | H  | Cl | Cl | 1,5-Dimethyl-pyrazol-4-yl |
| 1.218 | H  | H  | H  | Cl | Cl | 1-Methyl-pyrazol-4-yl |
| 1.219 | H  | H  | H  | Cl | Cl | 1,3-Dimethyl-pyrazol-5-yl |
| 1.220 | H  | H  | H  | Cl | Cl | 4-Methyl-oxazol-2-yl |
| 1.221 | H  | H  | H  | Cl | Cl | 5-Methylthio-thiazol-2-yl |
| 1.222 | H  | H  | H  | Cl | Cl | 4-Methoxy-1-methyl-pyrazol-5-yl |
| 1.223 | H  | H  | H  | Cl | Cl | 3-Cyclopropyl-isoxazol-5-yl |
| 1.224 | H  | H  | H  | Cl | Cl | 3-Isopropyl-isoxazol-5-yl |
| 1.225 | H  | H  | H  | Cl | Cl | (3-Methyl-phenyl)-thiazol-2-yl |
| 1.226 | H  | H  | H  | Cl | Cl | 5-Methyl-thiazol-2-yl |
| 1.227 | H  | H  | H  | Cl | Cl | 4-Bromo-2-thienyl |
| 1.228 | H  | H  | H  | Cl | Cl | 5-Methyl-2-thienyl |
| 1.229 | H  | H  | H  | Cl | Cl | 4-Methyl-2-thienyl |
| 1.230 | H  | H  | H  | Cl | Cl | 4-Methyl-thiazol-2-yl |
| 1.231 | H  | H  | H  | Cl | Cl | 4-Chloro-thiazol-2-yl |
| 1.232 | H  | H  | H  | Cl | Cl | 4,5-Dimethyl-thiazol-2-yl |
| 1.233 | H  | H  | H  | Cl | Cl | 4-Phenyl-thiazol-2-yl |
| 1.234 | H  | W  | H  | Cl | Cl | 2-Methoxy-thiazol-5-yl |
| 1.235 | H  | H  | H  | Cl | Cl | 4-Methyl-2-pyridyl |
| 1.236 | H  | H  | H  | Cl | Cl | 6-(2-Methoxyethyl)-2-pyridyl |
| 1.237 | H  | H  | H  | Cl | Cl | 6-Methylthio-2-pyridyl |
| 1.238 | H  | H  | H  | Cl | Cl | 6-Methoxy-3-pyridyl |
| 1.239 | H  | H  | H  | Cl | Cl | 6-Methoxy-2-pyridyl |
| 1.240 | H  | H  | H  | Cl | Cl | 6-Methyl-2-pyridyl. |
| 1.241 | H  | H  | H  | Cl | Cl | 6-(2,2,2-Trifluoroethoxy)-2-pyridyl |
| 1.242 | H  | H  | H  | Cl | Cl | 6-(2,2,2-Trifluoroethoxy)-3-pyridyl |
| 1.243 | H  | H  | H  | Cl | Cl | 5-Pyrimidinyl |
| 1.244 | H  | H  | H  | Cl | Cl | 6-Dimethylamino-3-pyridyl |
| 1.245 | H  | H  | H  | Cl | Cl | 1,2,4-Thiadiazol-5-yl |
| 1.246 | H  | H  | H  | Cl | Cl | 3-Ethoxycarbonyl-1-methyl-pyrazol-5-yl |
| 1.247 | H  | H  | H  | Cl | Cl | 2-Methylthio-pyrimidin-5-yl |
| 1.248 | H  | H  | H  | Cl | Cl | 2-Pyrimidinyl |
| 1.249 | H  | H  | H  | Cl | Cl | 2-Methylthio-pyrimidin-4-yl |
| 1.250 | H  | H  | H  | Cl | Cl | 5-Methylthio-1,3,4-thiadiazol-2-yl |
| 1.251 | H  | H  | H  | Cl | Cl | 5-Methoxy-1,3,4-thiadiazol-2-yl |
| 1.252 | H  | H  | H  | Cl | Cl | 4,5-Dihydro-thiazol-2-yl |
| 1.253 | H  | H  | H  | Cl | Cl | 5-Methyl-oxazol-2-yl |
| 1.254 | H  | H  | H  | Cl | Cl | 5-Phenyl-oxazol-2-yl |
| 1.255 | H  | H  | H  | Cl | Cl | 2-Methyl-oxazol-5-yl |
| 1.256 | H  | H  | H  | Cl | Cl | 2-Phenyl-oxazol-5-yl |
| 1.257 | H  | H  | H  | Cl | Cl | 2-Methyl-1,3,4-oxa-diazol-5-yl |
| 1.258 | H  | H  | H  | Cl | Cl | 2-Phenyl-1,3,4-oxa-diazol-5-yl |
| 1.259 | H  | H  | H  | Cl | Cl | 5-Trifluoromethyl-1,2,4-oxadiazol-3-yl |
| 1.260 | H  | H  | H  | Cl | Cl | 5-Methyl-1,2,4-oxadiazol-3-yl |
| 1.261 | H  | H  | H  | Cl | Cl | 5-Phenyl-1,2,4-oxadiazol-3-yl |
| 1.262 | H  | H  | H  | Cl | Cl | 5-Phenyl-isoxazol-3-yl |
| 1.263 | H  | H  | H  | Cl | Cl | 1-(4-Chlorophenyl)-1,2,4-triazol-2-yl |
| 1.264 | H  | H  | H  | Cl | Cl | 5-Cyano-4,5-dihydro-isoxazol-3-yl |
| 1.265 | H  | H  | H  | Cl | Cl | 5,6-Dihydro-4H-1,3-thiazin-2-yl |
| 1.266 | H  | H  | H  | Cl | Cl | 1,3-Dithiolan-2-yl |
| 1.267 | H  | H  | H  | Cl | Cl | 1,3-Dioxolan-2yl |
| 1.268 | H  | H  | H  | Cl | Cl | 1,3-Dithian-2-yl |
| 1.269 | H  | H  | H  | Cl | Cl | 1,3-Dioxan-2-yl |
| 1.270 | H  | H  | H  | Cl | Cl | 1,3-Oxathiolan-2-yl |
| 1.271 | H  | H  | H  | Cl | Cl | 1,2,4-Triazol-1-yl |

TABLE 1-continued

Compounds of the structure Id $$\text{[structure Id with substituents } R^3, R^4, R^5, \text{OH, O, M, Z, L]}$$

| No. | $R^3$ | $R^4$ | $R^5$ | L | M | Z |
|---|---|---|---|---|---|---|
| 1.272 | H | H | H | Cl | Cl | 3-Methyl-1,2,4-thiadiazol-5-yl |
| 1.273 | H | H | H | Cl | Cl | 1,2,4-Thiadiazol-5-yl |
| 1.274 | H | H | H | Cl | Cl | Thiazoline-4,5-dion-2-yl |
| 1.275 | H | H | H | Cl | Cl | 3-Oxo-3-H-1,2,4-dithiazol-5-yl |
| 1.276 | H | H | H | Cl | Cl | 2-Oxo-2-H-1,3,4-dithiazol-5-yl |
| 1.277 | H | H | H | $SO_2CH_3$ | $CH_3$ | 2-Thienyl |
| 1.278 | H | H | H | $SO_2CH_3$ | $CH_3$ | 3-Thienyl |
| 1.279 | H | H | H | $SO_2CH_3$ | $CH_3$ | 2-Furyl |
| 1.280 | H | H | H | $SO_2CH_3$ | $CH_3$ | 3-Furyl |
| 1.281 | H | H | H | $SO_2CH_3$ | $CH_3$ | 3-Methyl-isoxazol-5-yl |
| 1.282 | H | H | H | $SO_2CH_3$ | $CH_3$ | 5-Thiazolyl |
| 1.283 | H | H | H | $SO_2CH_3$ | $CH_3$ | 4-Thiazolyl |
| 1.284 | H | H | H | $SO_2CH_3$ | $CH_3$ | 2-Thiazolyl |
| 1.285 | H | H | H | $SO_2CH_3$ | $CH_3$ | 3-Methyl-isothiazol-5-yl |
| 1.286 | H | H | H | $SO_2CH_3$ | $CH_3$ | 3-Isoxazolyl |
| 1.287 | H | H | H | $SO_2CH_3$ | $CH_3$ | 5-Phenyl-thiazol-2-yl |
| 1.288 | H | H | H | $SO_2CH_3$ | $CH_3$ | 2-Pyridyl |
| 1.289 | H | H | H | $SO_2CH_3$ | $CH_3$ | 3-Pyridyl |
| 1.290 | H | H | H | $SO_2CH_3$ | $CH_3$ | 4-Pyridyl |
| 1.291 | H | H | H | $SO_2CH_3$ | $CH_3$ | 1-Methyl-2-pyrrolyl |
| 1.292 | H | H | H | $SO_2CH_3$ | $CH_3$ | 1-Methyl-1,2,4-triazol-5-yl |
| 1.293 | H | H | H | $SO_2CH_3$ | $CH_3$ | 2-Benzthiazolyl |
| 1.294 | H | H | H | $SO_2CH_3$ | $CH_3$ | 2-Quinolyl |
| 1.295 | H | H | H | $SO_2CH_3$ | $CH_3$ | 1-Methyl-benzimidazol-2-yl |
| 1.296 | H | H | H | $SO_2CH_3$ | $CH_3$ | 2-Oxazolyl |
| 1.297 | H | H | H | $SO_2CH_3$ | $CH_3$ | 1-Phenyl-pyrazol-5-yl |
| 1.298 | H | H | H | $SO_2CH_3$ | $CH_3$ | 1-Methyl-pyrazol-3-yl |
| 1.299 | H | H | H | $SO_2CH_3$ | $CH_3$ | 1-Methyl-pyrazol-5-yl |
| 1.300 | H | H | H | $SO_2CH_3$ | $CH_3$ | 1,3-Dimethyl-pyrazol-3-yl |
| 1.301 | H | H | H | $SO_2CH_3$ | $CH_3$ | 1-Phenyl-pyrazol-3-yl |
| 1.302 | H | H | H | $SO_2CH_3$ | $CH_3$ | 1,4-Dimethyl-pyrazol-5-yl |
| 1.303 | H | H | H | $SO_2CH_3$ | $CH_3$ | 1,3-Dimethyl-pyrazol-4-yl |
| 1.304 | H | H | H | $SO_2CH_3$ | $CH_3$ | 1,5-Dimethyl-pyrazol-4-yl |
| 1.305 | H | H | H | $SO_2CH_3$ | $CH_3$ | 1-Methyl-pyrazol-4-yl |
| 1.306 | H | H | H | $SO_2CH_3$ | $CH_3$ | 1,3-Dimethyl-pyrazol-5-yl |
| 1.307 | H | H | H | $SO_2CH_3$ | $CH_3$ | 4-Methyl-oxazol-2-yl |
| 1.308 | H | H | H | $SO_2CH_3$ | $CH_3$ | 5-Methylthio-thiazol-2-yl |
| 1.309 | H | H | H | $SO_2CH_3$ | $CH_3$ | 4-Methoxy-1-methyl-pyrazol-5-yl |
| 1.310 | H | H | H | $SO_2CH_3$ | $CH_3$ | 3-Cyclopropyl-isoxazol-5-yl |
| 1.311 | H | H | H | $SO_2CH_3$ | $CH_3$ | 3-Isopropyl-isoxazol-5-yl |
| 1.312 | H | H | H | $SO_2CH_3$ | $CH_3$ | (3-Methyl-phenyl-thiazol-2-yl |
| 1.313 | H | H | H | $SO_2CH_3$ | $CH_3$ | 5-Methyl-thiazol-2-yl |
| 1.314 | H | H | H | $SO_2CH_3$ | $CH_3$ | 4-Bromo-2-thienyl |
| 1.315 | H | H | H | $SO_2CH_3$ | $CH_3$ | 5-Methyl-2-thienyl |
| 1.316 | H | H | H | $SO_2CH_3$ | $CH_3$ | 4-Methyl-2-thienyl |
| 1.317 | H | H | H | $SO_2CH_3$ | $CH_3$ | 4-Methyl-thiazol-2-yl |
| 1.318 | H | H | H | $SO_2CH_3$ | $CH_3$ | 4-Chloro-thiazol-2-yl |
| 1.319 | H | H | H | $SO_2CH_3$ | $CH_3$ | 4,5-Dimethyl-thiazol-2-yl |
| 1.320 | H | H | H | $SO_2CH_3$ | $CH_3$ | 4-Phenyl-thiazol-2-yl |
| 1.321 | H | H | H | $SO_2CH_3$ | $CH_3$ | 2-Methoxy-thiazol-5-yl |
| 1.322 | H | H | H | $SO_2CH_3$ | $CH_3$ | 4-Methyl-2-pyridyl |
| 1.323 | H | H | H | $SO_2CH_3$ | $CH_3$ | 6-(2-Methoxyethyl)-2-pyridyl |
| 1.324 | H | H | H | $SO_2CH_3$ | $CH_3$ | 6-Methylthio-2-pyridyl |
| 1.325 | H | H | H | $SO_2CH_3$ | $CH_3$ | 6-Methoxy-3-pyridyl |
| 1.326 | H | H | H | $SO_2CH_3$ | $CH_3$ | 6-Methoxy-2-pyridyl |
| 1.327 | H | H | H | $SO_2CH_3$ | $CH_3$ | 6-Methyl-2-pyridyl |
| 1.328 | H | H | H | $SO_2CH_3$ | $CH_3$ | 6-(2,2,2-Trifluoroethoxy)-2-pyridyl |
| 1.329 | H | H | H | $SO_2CH_3$ | $CH_3$ | 6-(2,2,2-Trifluoroethoxy)-3-pyridyl |
| 1.330 | H | H | H | $SO_2CH_3$ | $CH_3$ | 5-Pyrimidinyl |
| 1.331 | H | H | H | $SO_2CH_3$ | $CH_3$ | 6-Dimethylamino-3-pyridyl |
| 1.332 | H | H | H | $SO_2CH_3$ | $CH_3$ | 1,2,4-Thiadiazol-5-yl |
| 1.333 | H | H | H | $SO_2CH_3$ | $CH_3$ | 3-Ethoxycarbonyl-1-methyl-pyrazol-5-yl |
| 1.334 | H | H | H | $SO_2CH_3$ | $CH_3$ | 2-Methylthio-pyrimidin-5-yl |
| 1.335 | H | H | H | $SO_2CH_3$ | $CH_3$ | 2-Pyrimidinyl |
| 1.336 | H | H | H | $SO_2CH_3$ | $CH_3$ | 2-Methylthio-pyrimidin-4-yl |

TABLE 1-continued

Compounds of the structure Id

| No. | R³ | R⁴ | R⁵ | L | M | Z |
|---|---|---|---|---|---|---|
| 1.337 | H | H | H | SO₂CH₃ | CH₃ | 5-Methylthio-1,3,4-thiadiazol-2-yl |
| 1.338 | H | H | H | SO₂CH₃ | CH₃ | 5-Methoxy-1,3,4-thiadiazol-2-yl |
| 1.339 | H | H | H | SO₂CH₃ | CH₃ | 4,5-Dihydro-thiazol-2-yl |
| 1.340 | H | H | H | SO₂CH₃ | CH₃ | 5-Methyl-oxazol-2-yl |
| 1.341 | H | H | H | SO₂CH₃ | CH₃ | 5-Phenyl-oxazol-2-yl |
| 1.342 | H | H | H | SO₂CH₃ | CH₃ | 2-Methyl-oxazol-5-yl |
| 1.343 | H | H | H | SO₂CH₃ | CH₃ | 2-Phenyl-oxazol-5-yl |
| 1.344 | H | H | H | SO₂CH₃ | CH₃ | 2-Methyl-1,3,4-oxa-diazol-5-yl |
| 1.345 | H | H | H | SO₂CH₃ | CH₃ | 2-Phenyl-1,3,4-oxa-diazol-5-yl |
| 1.346 | H | H | H | SO₂CH₃ | CH₃ | 5-Trifluoromethyl-1,2,4-oxadiazol-3-yl |
| 1.347 | H | H | H | SO₂CH₃ | CH₃ | 5-Methyl-1,2,4-oxadiazol-3-yl |
| 1.348 | H | H | H | SO₂CH₃ | CH₃ | 5-Phenyl-1,2,4-oxadiazol-3-yl |
| 1.349 | H | H | H | SO₂CH₃ | CH₃ | 5-Phenyl-isoxazol-3-yl |
| 1.350 | H | H | H | SO₂CH₃ | CH₃ | 1-(4-Chlorophenyl)-1,2,4-triazol-2-yl |
| 1.351 | H | H | H | SO₂CH₃ | CH₃ | 5-Cyano-4,5-dihydro-isoxazol-3-yl |
| 1.352 | H | H | H | SO₂CH₃ | CH₃ | 5,6-Dihydro-4H-1,3-thiazin-2-yl |
| 1.353 | H | H | H | SO₂CH₃ | CH₃ | 1,3-Dithiolan-2-yl |
| 1.354 | H | H | H | SO₂CH₃ | CH₃ | 1,3-Dioxolan-2yl |
| 1.355 | H | H | H | SO₂CH₃ | CH₃ | 1,3-Dithian-2-yl |
| 1.356 | H | H | H | SO₂CH₃ | CH₃ | 1,3-Dioxan-2-yl |
| 1.357 | H | H | H | SO₂CH₃ | CH₃ | 1,3-oxathiolan-2-yl |
| 1.358 | H | H | H | SO₂CH₃ | CH₃ | 1,2,4-Triazol-1-yl |
| 1.359 | H | H | H | SO₂CH₃ | CH₃ | 3-Methyl-1,2,4-thiadiazol-5-yl |
| 1.360 | H | H | H | SO₂CH₃ | CH₃ | 1,2,4-Thiadiazol-5-yl |
| 1.361 | H | H | H | SO₂CH₃ | CH₃ | Thiazoline-4,5-dion-2-yl |
| 1.362 | H | H | H | SO₂CH₃ | CH₃ | 3-Oxo-3-H-1,2,4-dithiazol-5-yl |
| 1.363 | H | H | H | SO₂CH₃ | CH₃ | 2-Oxo-2-H-1,3,4-dithiazol-5-yl |
| 1.364 | H | H | H | SO₂CH₃ | CN | 2-Thienyl |
| 1.365 | H | H | H | SO₂CH₃ | CN | 3-Thienyl |
| 1.366 | H | H | H | SO₂CH₃ | CN | 2-Furyl |
| 1.367 | H | H | H | SO₂CH₃ | CN | 3-Furyl |
| 1.368 | H | H | H | SO₂CH₃ | CN | 3-Methyl-isoxazol-5-yl |
| 1.369 | H | H | H | SO₂CH₃ | CN | 5-Thiazolyl |
| 1.370 | H | H | H | SO₂CH₃ | CN | 4-Thiazolyl |
| 1.371 | H | H | H | SO₂CH₃ | CN | 2-Thiazolyl |
| 1.372 | H | H | H | SO₂CH₃ | CN | 3-Methyl-isothiazol-5-yl |
| 1.373 | H | H | H | SO₂CH₃ | CN | 3-Isoxazolyl |
| 1.374 | H | H | H | SO₂CH₃ | CN | 5-Phenyl-thiazol-2-yl |
| 1.375 | H | H | H | SO₂CH₃ | CN | 2-Pyridyl |
| 1.376 | H | H | H | SO₂CH₃ | CN | 3-Pyridyl |
| 1.377 | H | H | H | SO₂CH₃ | CN | 4-Pyridyl |
| 1.378 | H | H | H | SO₂CH₃ | CN | 1-Methyl-2-pyrrolyl |
| 1.379 | H | H | H | SO₂CH₃ | CN | 1-Methyl-1,2,4-triazol-5-yl |
| 1.380 | H | H | H | SO₂CH₃ | CN | 2-Benzthiazolyl |
| 1.381 | H | H | H | SO₂CH₃ | CN | 2-Quinolyl |
| 1.382 | H | H | H | SO₂CH₃ | CN | 1-Methyl-benzimidazol-2-yl |
| 1.383 | H | H | H | SO₂CH₃ | CN | 2-Oxazolyl |
| 1.384 | H | H | H | SO₂CH₃ | CN | 1-Phenyl-pyrazol-5-yl |
| 1.385 | H | H | H | SO₂CH₃ | CN | 1-Methyl-pyrazol-3-yl |
| 1.386 | H | H | H | SO₂CH₃ | CN | 1-Methyl-pyrazol-5-yl |
| 1.387 | H | H | H | SO₂CH₃ | CN | 1,3-Dimethyl-pyrazol-3-yl |
| 1.388 | H | H | H | SO₂CH₃ | CN | 1-Phenyl-pyrazol-3-yl |
| 1.389 | H | H | H | SO₂CH₃ | CN | 1,4-Dimethyl-pyrazol-5-yl |
| 1.390 | H | H | H | SO₂CH₃ | CN | 1,3-Dimethyl-pyrazol-4-yl |
| 1.391 | H | H | H | SO₂CH₃ | CN | 1,5-Dimethyl-pyrazol-4-yl |
| 1.392 | H | H | H | SO₂CH₃ | CN | 1-Methyl-pyrazol-4-yl |
| 1.393 | H | H | H | SO₂CH₃ | CN | 1,3-Dimethyl-pyrazol-5-yl |
| 1.394 | H | H | H | SO₂CH₃ | CN | 4-Methyl-oxazol-2-yl |
| 1.395 | H | H | H | SO₂CH₃ | CN | 5-Methylthio-thiazol-2-yl |
| 1.396 | H | H | H | SO₂CH₃ | CN | 4-Methoxy-1-methyl-pyrazol-5-yl |
| 1.397 | H | H | H | SO₂CH₃ | CN | 3-Cyclopropyl-isoxazol-5-yl |
| 1.398 | H | H | H | SO₂CH₃ | CN | 3-Isopropyl-isoxazol-5-yl |
| 1.399 | H | H | H | SO₂CH₃ | CN | (3-Methyl-phenyl)-thiazol-2-yl |
| 1.400 | H | H | H | SO₂CH₃ | CN | 5-Methyl-thiazol-2-yl |
| 1.401 | H | H | H | SO₂CH₃ | CN | 4-Bromo-2-thienyl |

TABLE 1-continued

Compounds of the structure Id

| No. | R³ | R⁴ | R⁵ | L | M | Z |
|---|---|---|---|---|---|---|
| 1.402 | H | H | H | SO₂CH₃ | CN | 5-Methyl-2-thienyl |
| 1.403 | H | H | H | SO₂CH₃ | CN | 4-Methyl-2-thienyl |
| 1.404 | H | H | H | SO₂CH₃ | CN | 4-Methyl-thiazol-2-yl |
| 1.405 | H | H | H | SO₂CH₃ | CN | 4-Chloro-thiazol-2-yl |
| 1.406 | H | H | H | SO₂CH₃ | CN | 4,5-Dimethyl-thiazol-2-yl |
| 1.407 | H | H | H | SO₂CH₃ | CN | 4-Phenyl-thiazol-2-yl |
| 1.408 | H | H | H | SO₂CH₃ | CN | 2-Methoxy-thiazol-5-yl |
| 1.409 | H | H | H | SO₂CH₃ | CN | 4-Methyl-2-pyridyl |
| 1.410 | H | H | H | SO₂CH₃ | CN | 6-(2-Methoxyethyl)-2-pyridyl |
| 1.411 | H | H | H | SO₂CH₃ | CN | 6-Methylthio-2-pyridyl |
| 1.412 | H | H | H | SO₂CH₃ | CN | 6-Methoxy-3-pyridyl |
| 1.413 | H | H | H | SO₂CH₃ | CN | 6-Methoxy-2-pyridyl |
| 1.414 | H | H | H | SO₂CH₃ | CN | 6-Methyl-2-pyridyl |
| 1.415 | H | H | H | SO₂CH₃ | CN | 6-(2,2,2-Trifluoroethoxy)-2-pyridyl |
| 1.416 | H | H | H | SO₂CH₃ | CN | 6-(2,2,2-Trifluoroethoxy)-3-pyridyl |
| 1.417 | H | H | H | SO₂CH₃ | CN | 5-Pyrimidinyl |
| 1.418 | H | H | H | SO₂CH₃ | CN | 6-Dimethylamino-3-pyridyl |
| 1.419 | H | H | H | SO₂CH₃ | CN | 1,2,4-Thiadiazol-5-yl |
| 1.420 | H | H | H | SO₂CH₃ | CN | 3-Ethoxycarbonyl-1-methyl-pyrazol-5-yl |
| 1.421 | H | H | H | SO₂CH₃ | CN | 2-Methylthio-pyrimidin-5-yl |
| 1.422 | H | H | H | SO₂CH₃ | CN | 2-Pyrimidinyl |
| 1.423 | H | H | H | SO₂CH₃ | CN | 2-Methylthio-pyrimidin-4-yl |
| 1.424 | H | H | H | SO₂CH₃ | CN | 5-Methylthio-1,3,4-thiadiazol-2-yl |
| 1.425 | H | H | H | SO₂CH₃ | CN | 5-Methoxy-1,3,4-thiadiazol-2-yl |
| 1.426 | H | H | H | SO₂CH₃ | CN | 4,5-Dihydro-thiazol-2-yl |
| 1.427 | H | H | H | SO₂CH₃ | CN | 5-Methyl-oxazol-2-yl |
| 1.428 | H | H | H | SO₂CH₃ | CN | 5-Phenyl-oxazol-2-yl |
| 1.429 | H | H | H | SO₂CH₃ | CN | 2-Methyl-oxazol-5-yl |
| 1.430 | H | H | H | SO₂CH₃ | CN | 2-Phenyl-oxazol-5-yl |
| 1.431 | H | H | H | SO₂CH₃ | CN | 2-Methyl-1,3,4-oxa-diazol-5-yl |
| 1.432 | H | H | H | SO₂CH₃ | CN | 2-Phenyl-1,3,4-oxa-diazol-5-yl |
| 1.433 | H | H | H | SO₂CH₃ | CN | 5-Trifluoromethyl-1,2,4-oxadiazol-3-yl |
| 1.434 | H | H | H | SO₂CH₃ | CN | 5-Methyl-1,2,4-oxadiazol-3-yl |
| 1.435 | H | H | H | SO₂CH₃ | CN | 5-Phenyl-1,2,4-oxadiazol-3-yl |
| 1.436 | H | H | H | SO₂CH₃ | CN | 5-Phenyl-isoxazol-3-yl |
| 1.437 | H | H | H | SO₂CH₃ | CN | 1-(4-Chlorophenyl)-1,2,4-triazol-2-yl |
| 1.438 | H | H | H | SO₂CH₃ | CN | 5-Cyano-4,5-dihydro-isoxazol-3-yl |
| 1.439 | H | H | H | SO₂CH₃ | CN | 5,6-Dihydro-4H-1,3-thiazin-2-yl |
| 1.440 | H | H | H | SO₂CH₃ | CN | 1,3-Dithiolan-2-yl |
| 1.441 | H | H | H | SO₂CH₃ | CN | 1,3-Dioxolan-2-yl |
| 1.442 | H | H | H | SO₂CH₃ | CN | 1,3-Dithian-2-yl |
| 1.443 | H | H | H | SO₂CH₃ | CN | 1,3-Dioxan-2-yl |
| 1.444 | H | H | H | SO₂CH₃ | CN | 1,3-Oxathiolan-2-yl |
| 1.445 | H | H | H | SO₂CH₃ | CN | 1,2,4-Triazol-1-yl |
| 1.446 | H | H | H | SO₂CH₃ | CN | 3-Methyl-1,2,4-thiadiazol-5-yl |
| 1.447 | H | H | H | SO₂CH₃ | CN | 1,2,4-Thiadiazol-5-yl |
| 1.448 | H | H | H | SO₂CH₃ | CN | Thiazoline-4,5-dion-2-yl |
| 1.449 | H | H | H | SO₂CH₃ | CN | 3-oxo-3-H-1,2,4-dithiazol-5-yl |
| 1.450 | H | H | H | SO₂CH₃ | CN | 2-oxo-2-H-1,3,4-dithiazol-5-yl |
| 1.451 | H | H | H | SO₂CH₃ | H | 2-Thienyl |
| 1.452 | H | H | H | SO₂CH₃ | H | 3-Thienyl |
| 1.453 | H | H | H | SO₂CH₃ | H | 2-Furyl |
| 1.454 | H | H | H | SO₂CH₃ | H | 3-Furyl |
| 1.455 | H | H | H | SO₂CH₃ | H | 3-Methyl-isoxazol-5-yl |
| 1.456 | H | H | H | SO₂CH₃ | H | 5-Thiazolyl |
| 1.457 | H | H | H | SO₂CH₃ | H | 4-Thiazolyl |
| 1.458 | H | H | H | SO₂CH₃ | H | 2-Thiazolyl |
| 1.459 | H | H | H | SO₂CH₃ | H | 3-Methyl-isothiazol-5-yl |
| 1.460 | H | H | H | SO₂CH₃ | H | 3-Isoxazolyl |
| 1.461 | H | H | H | SO₂CH₃ | H | 5-Phenyl-thiazol-2-yl |
| 1.462 | H | H | H | SO₂CH₃ | H | 2-Pyridyl |
| 1.463 | H | H | H | SO₂CH₃ | H | 3-Pyridyl |
| 1.464 | H | H | H | SO₂CH₃ | H | 4-Pyridyl |
| 1.465 | H | H | H | SO₂CH₃ | H | 1-Methyl-2-pyrrolyl |
| 1.466 | H | H | H | SO₂CH₃ | H | 1-Methyl-1,2,4-triazol-5-yl |

TABLE 1-continued

Compounds of the structure Id

| No. | R³ | R⁴ | R⁵ | L | M | Z |
|---|---|---|---|---|---|---|
| 1.467 | H | H | H | SO$_2$CH$_3$ | H | 2-Benzthiazolyl |
| 1.468 | H | H | H | SO$_2$CH$_3$ | H | 2-Quinolyl |
| 1.469 | H | H | H | SO$_2$CH$_3$ | H | 1-Methyl-benzimidazol-2-yl |
| 1.470 | H | H | H | SO$_2$CH$_3$ | H | 2-oxazolyl |
| 1.471 | H | H | H | SO$_2$CH$_3$ | H | 1-Phenyl-pyrazol-5-yl |
| 1.472 | H | H | H | SO$_2$CH$_3$ | H | 1-Methyl-pyrazol-3-yl |
| 1.473 | H | H | H | SO$_2$CH$_3$ | H | 1-Methyl-pyrazol-5-yl |
| 1.474 | H | H | H | SO$_2$CH$_3$ | H | 1,3-Dimethyl-pyrazol-3-yl |
| 1.475 | H | H | H | SO$_2$CH$_3$ | H | 1-Phenyl-pyrazol-3-yl |
| 1.476 | H | H | H | SO$_2$CH$_3$ | H | 1,4-Dimethyl-pyrazol-5-yl |
| 1.477 | H | H | H | SO$_2$CH$_3$ | H | 1,3-Dimethyl-pyrazol-4-yl |
| 1.478 | H | H | H | SO$_2$CH$_3$ | H | 1,5-Dimethyl-pyrazol-4-yl |
| 1.479 | H | H | H | SO$_2$CH$_3$ | H | 1-Methyl-pyrazol-4-yl |
| 1.480 | H | H | H | SO$_2$CH$_3$ | H | 1,3-Dimethyl-pyrazol-5-yl |
| 1.481 | H | H | H | SO$_2$CH$_3$ | H | 4-Methyl-oxazol-2-yl |
| 1.482 | H | H | H | SO$_2$CH$_3$ | H | 5-Methylthio-thiazol-2-yl |
| 1.483 | H | H | H | SO$_2$CH$_3$ | H | 4-Methoxy-1-methyl-pyrazol-5-yl |
| 1.484 | H | H | H | SO$_2$CH$_3$ | H | 3-Cyclopropyl-isoxazol-5-yl |
| 1.485 | H | H | H | SO$_2$CH$_3$ | H | 3-Isopropyl-isoxazol-5-yl |
| 1.486 | H | H | H | SO$_2$CH$_3$ | H | (3-Methyl-phenyl)-thiazol-2-yl |
| 1.487 | H | H | H | SO$_2$CH$_3$ | H | 5-Methyl-thiazol-2-yl |
| 1.488 | H | H | H | SO$_2$CH$_3$ | H | 4-Bromo-2-thienyl |
| 1.489 | H | H | H | SO$_2$CH$_3$ | H | 5-Methyl-2-thienyl |
| 1.490 | H | H | H | SO$_2$CH$_3$ | H | 4-Methyl-2-thienyl |
| 1.491 | H | H | H | SO$_2$CH$_3$ | H | 4-Methyl-thiazol-2-yl |
| 1.492 | H | H | H | SO$_2$CH$_3$ | H | 4-Chloro-thiazol-2-yl |
| 1.493 | H | H | H | SO$_2$CH$_3$ | H | 4,5-Dimethyl-thiazol-2-yl |
| 1.494 | H | H | H | SO$_2$CH$_3$ | H | 4-Phenyl-thiazol-2-yl |
| 1.495 | H | H | H | SO$_2$CH$_3$ | H | 2-Methoxy-thiazol-5-yl |
| 1.496 | H | H | H | SO$_2$CH$_3$ | H | 4-Methyl-2-pyridyl |
| 1.497 | H | H | H | SO$_2$CH$_3$ | H | 6-(2-Methoxyethyl)-2-pyridyl |
| 1.498 | H | H | H | SO$_2$CH$_3$ | H | 6-Methylthio-2-pyridyl |
| 1.499 | H | H | H | SO$_2$CH$_3$ | H | 6-Methoxy-3-pyridyl |
| 1.500 | H | H | H | SO$_2$CH$_3$ | H | 6-Methoxy-2-pyridyl |
| 1.501 | H | H | H | SO$_2$CH$_3$ | H | 6-Methyl-2-pyridyl |
| 1.502 | H | H | H | SO$_2$CH$_3$ | H | 6-(2,2,2-Trifluoroethoxy)-2-pyridyl |
| 1.503 | H | H | H | SO$_2$CH$_3$ | H | 6-(2,2,2-Trifluoroethoxy)-3-pyridyl |
| 1.504 | H | H | H | SO$_2$CH$_3$ | H | 5-Pyrimidinyl |
| 1.505 | H | H | H | SO$_2$CH$_3$ | H | 6-Dimethylamino-3-pyridyl |
| 1.506 | H | H | H | SO$_2$CH$_3$ | H | 1,2,4-Thiadiazol-5-yl |
| 1.507 | H | H | H | SO$_2$CH$_3$ | H | 3-Ethoxycarbonyl-1-methyl-pyrazol-5-yl |
| 1.508 | H | H | H | SO$_2$CH$_3$ | H | 2-Methylthio-pyrimidin-5-yl |
| 1.509 | H | H | H | SO$_2$CH$_3$ | H | 2-Pyrimidinyl |
| 1.510 | H | H | H | SO$_2$CH$_3$ | H | 2-Methylthio-pyrimidin-4-yl |
| 1.511 | H | H | H | SO$_2$CH$_3$ | H | 5-Methylthio-1,3,4-thiadiazol-2-yl |
| 1.512 | H | H | H | SO$_2$CH$_3$ | H | 5-Methoxy-1,3,4-thiadiazol-2-yl |
| 1.513 | H | H | H | SO$_2$CH$_3$ | H | 4,5-Dihydro-thiazol-2-yl |
| 1.514 | H | H | H | SO$_2$CH$_3$ | H | 5-Methyl-oxazol-2-yl |
| 1.515 | H | H | H | SO$_2$CH$_3$ | H | 5-Phenyl-oxazol-2-yl |
| 1.516 | H | H | H | SO$_2$CH$_3$ | H | 2-Methyl-oxazol-5-yl |
| 1.517 | H | H | H | SO$_2$CH$_3$ | H | 2-Phenyl-oxazol-5-yl |
| 1.518 | H | H | H | SO$_2$CH$_3$ | H | 2-Methyl-1,3,4-oxa-diazol-5-yl |
| 1.519 | H | H | H | SO$_2$CH$_3$ | H | 2-Phenyl-1,3,4-oxa-diazol-5-yl |
| 1.520 | H | H | H | SO$_2$CH$_3$ | H | 5-Trifluoromethyl-1,2,4-oxadiazol-3-yl |
| 1.521 | H | H | H | SO$_2$CH$_3$ | H | 5-Methyl-1,2,4-oxadiazol-3-yl |
| 1.522 | H | H | H | SO$_2$CH$_3$ | H | 5-Phenyl-1,2,4-oxadiazol-3-yl |
| 1.523 | H | H | H | SO$_2$CH$_3$ | H | 5-Phenyl-isoxazol-3-yl |
| 1.524 | H | H | H | SO$_2$CH$_3$ | H | 1-(4-Chlorophenyl)-1,2,4-triazol-2-yl |
| 1.525 | H | H | H | SO$_2$CH$_3$ | H | 5-Cyano-4,5-dihydro-isoxazol-3-yl |
| 1.526 | H | H | H | SO$_2$CH$_3$ | H | 5,6-Dihydro-4H-1,3-thiazin-2-yl |
| 1.527 | H | H | H | SO$_2$CH$_3$ | H | 1,3-Dithiolan-2-yl |
| 1.528 | H | H | H | SO$_2$CH$_3$ | H | 1,3-Dioxolan-2-yl |
| 1.529 | H | H | H | SO$_2$CH$_3$ | H | 1,3-Dithian-2-yl |
| 1.530 | H | H | H | SO$_2$CH$_3$ | H | 1,3-Dioxan-2-yl |
| 1.531 | H | H | H | SO$_2$CH$_3$ | H | 1,3-Oxathiolan-2-yl |

TABLE 1-continued

Compounds of the structure Id

| No. | R³ | R⁴ | R⁵ | L | M | Z |
|---|---|---|---|---|---|---|
| 1.532 | H | H | H | SO₂CH₃ | H | 1,2,4-Triazol-1-yl |
| 1.533 | H | H | H | SO₂CH₃ | H | 3-Methyl-1,2,4-thiadiazol-5-yl |
| 1.534 | H | H | H | SO₂CH₃ | H | 1,2,4-Thiadiazol-5-yl |
| 1.535 | H | H | H | SO₂CH₃ | H | Thiazoline-4,5-dion-2-yl |
| 1.536 | H | H | H | SO₂CH₃ | H | 3-Oxo-3-H-1,2,4-dithiazol-5-yl |
| 1.537 | H | H | H | SO₂CH₃ | H | 2-oxo-2-H-1,3,4-dithiazol-5-yl |
| 1.538 | CH₃ | H | H | SO₂CH₃ | H | 2-Thienyl |
| 1.539 | CH₃ | H | H | SO₂CH₃ | H | 3-Thienyl |
| 1.540 | CH₃ | H | H | SO₂CH₃ | H | 2-Furyl |
| 1.541 | CH₃ | H | H | SO₂CH₃ | H | 3-Furyl |
| 1.542 | CH₃ | H | H | SO₂CH₃ | H | 3-Methyl-isoxazol-5-yl |
| 1.543 | CH₃ | H | H | SO₂CH₃ | H | 5-Thiazolyl |
| 1.544 | CH₃ | H | H | SO₂CH₃ | H | 4-Thiazolyl |
| 1.545 | CH₃ | H | H | SO₂CH₃ | H | 2-Thiazolyl |
| 1.546 | CH₃ | H | H | SO₂CH₃ | H | 3-Methyl-isothiazol-5-yl |
| 1.547 | CH₃ | H | H | SO₂CH₃ | H | 3-Isoxazolyl |
| 1.548 | CH₃ | H | H | SO₂CH₃ | H | 5-Phenyl-thiazol-2-yl |
| 1.549 | CH₃ | H | H | SO₂CH₃ | H | 2-Pyridyl |
| 1.550 | CH₃ | H | H | SO₂CH₃ | H | 3-Pyridyl |
| 1.551 | CH₃ | H | H | SO₂CH₃ | H | 4-Pyridyl |
| 1.552 | CH₃ | H | H | SO₂CH₃ | H | 1-Methyl-2-pyrrolyl |
| 1.553 | CH₃ | H | H | SO₂CH₃ | H | 1-Methyl-1,2,4-triazol-5-yl |
| 1.554 | CH₃ | H | H | SO₂CH₃ | H | 2-Benzthiazolyl |
| 1.555 | CH₃ | H | H | SO₂CH₃ | H | 2-Quinolyl |
| 1.556 | CH₃ | H | H | SO₂CH₃ | H | 1-Methyl-benzimidazol-2-yl |
| 1.557 | CH₃ | H | H | SO₂CH₃ | H | 2-Oxazolyl |
| 1.558 | CH₃ | H | H | SO₂CH₃ | H | 1-Phenyl-pyrazol-5-yl |
| 1.559 | CH₃ | H | H | SO₂CH₃ | H | 1-Methyl-pyrazol-3-yl |
| 1.560 | CH₃ | H | H | SO₂CH₃ | H | 1-Methyl-pyrazol-5-yl |
| 1.561 | CH₃ | H | H | SO₂CH₃ | H | 1,3-Dimethyl-pyrazol-3-yl |
| 1.562 | CH₃ | H | H | SO₂CH₃ | H | 1-Phenyl-pyrazol-3-yl |
| 1.563 | CH₃ | H | H | SO₂CH₃ | H | 1,4-Dimethyl-pyrazol-5-yl |
| 1.564 | CH₃ | H | H | SO₂CH₃ | H | 1,3-Dimethyl-pyrazol-4-yl |
| 1.565 | CH₃ | H | H | SO₂CH₃ | H | 1,5-Dimethyl-pyrazol-4-yl |
| 1.566 | CH₃ | H | H | SO₂CH₃ | H | 1-Methyl-pyrazol-4-yl |
| 1.567 | CH₃ | H | H | SO₂CH₃ | H | 1,3-Dimethyl-pyrazol-5-yl |
| 1.568 | CH₃ | H | H | SO₂CH₃ | H | 4-Methyl-oxazol-2-yl |
| 1.569 | CH₃ | H | H | SO₂CH₃ | H | 5-Methylthio-thiazol-2-yl |
| 1.570 | CH₃ | H | H | SO₂CH₃ | H | 4-Methoxy-1-methyl-pyrazol-5-yl |
| 1.571 | CH₃ | H | H | SO₂CH₃ | H | 3-Cyclopropyl-isoxazol-5-yl |
| 1.572 | CH₃ | H | H | SO₂CH₃ | H | 3-Isopropyl-isoxazol-5-yl |
| 1.573 | CH₃ | H | H | SO₂CH₃ | H | (3-Methyl-phenyl)-thiazol-2-yl |
| 1.574 | CH₃ | H | H | SO₂CH₃ | H | 5-Methyl-thiazol-2-yl |
| 1.575 | CH₃ | H | H | SO₂CH₃ | H | 4-Bromo-2-thienyl |
| 1.576 | CH₃ | H | H | SO₂CH₃ | H | 5-Methyl-2-thienyl |
| 1.577 | CH₃ | H | H | SO₂CH₃ | H | 4-Methyl-2-thienyl |
| 1.578 | CH₃ | H | H | SO₂CH₃ | H | 4-Methyl-thiazol-2-yl |
| 1.579 | CH₃ | H | H | SO₂CH₃ | H | 4-Chloro-thiazol-2-yl |
| 1.580 | CH₃ | H | H | SO₂CH₃ | H | 4,5-Dimethyl-thiazol-2-yl |
| 1.581 | CH₃ | H | H | SO₂CH₃ | H | 4-Phenyl-thiazol-2-yl |
| 1.582 | CH₃ | H | H | SO₂CH₃ | H | 2-Methoxy-thiazol-5-yl |
| 1.583 | CH₃ | H | H | SO₂CH₃ | H | 4-Methyl-2-pyridyl |
| 1.584 | CH₃ | H | H | SO₂CH₃ | H | 6-(2-Methoxyethyl)-2-pyridyl |
| 1.585 | CH₃ | H | H | SO₂CH₃ | H | 6-Methylthio-2-pyridyl |
| 1.586 | CH₃ | H | H | SO₂CH₃ | H | 6-Methoxy-3-pyridyl |
| 1.587 | CH₃ | H | H | SO₂CH₃ | H | 6-Methoxy-2-pyridyl |
| 1.588 | CH₃ | H | H | SO₂CH₃ | H | 6-Methyl-2-pyridyl |
| 1.589 | CH₃ | H | H | SO₂CH₃ | H | 6-(2,2,2-Trifluoroethoxy)-2-pyridyl |
| 1.590 | CH₃ | H | H | SO₂CH₃ | H | 6-(2,2,2-Trifluoroethoxy)-3-pyridyl |
| 1.591 | CH₃ | H | H | SO₂CH₃ | H | 5-Pyrimidinyl |
| 1.592 | CH₃ | H | H | SO₂CH₃ | H | 6-Dimethylamino-3-pyridyl |
| 1.593 | CH₃ | H | H | SO₂CH₃ | H | 1,2,4-Thiadiazol-5-yl |
| 1.594 | CH₃ | H | H | SO₂CH₃ | H | 3-Ethoxycarbonyl-1-methyl-pyrazol-5-yl |
| 1.595 | CH₃ | H | H | SO₂CH₃ | H | 2-Methylthio-pyrimidin-5-yl |
| 1.596 | CH₃ | H | H | SO₂CH₃ | H | 2-Pyrimidinyl |

TABLE 1-continued

Compounds of the structure Id

| No. | R³ | R⁴ | R⁵ | L | M | Z |
|---|---|---|---|---|---|---|
| 1.597 | CH₃ | H | H | SO₂CH₃ | H | 2-Methylthio-pyrimidin-4-yl |
| 1.598 | CH₃ | H | H | SO₂CH₃ | H | 5-Methylthio-1,3,4-thiadiazol-2-yl |
| 1.599 | CH₃ | H | H | SO₂CH₃ | H | 5-Methoxy-1,3,4-thiadiazol-2-yl |
| 1.600 | CH₃ | H | H | SO₂CH₃ | H | 4,5-Dihydro-thiazol-2-yl |
| 1.601 | CH₃ | H | H | SO₂CH₃ | H | 5-Methyl-oxazol-2-yl |
| 1.602 | CH₃ | H | H | SO₂CH₃ | H | 5-Phenyl-oxazol-2-yl |
| 1.603 | CH₃ | H | H | SO₂CH₃ | H | 2-Methyl-oxazol-5-yl |
| 1.604 | CH₃ | H | H | SO₂CH₃ | H | 2-Phenyl-oxazol-5-yl |
| 1.605 | CH₃ | H | H | SO₂CH₃ | H | 2-Methyl-1,3,4-oxa-diazol-5-yl |
| 1.606 | CH₃ | H | H | SO₂CH₃ | H | 2-Phenyl-1,3,4-oxa-diazol-5-yl |
| 1.607 | CH₃ | H | H | SO₂CH₃ | H | 5-Trifluoromethyl-1,2,4-oxadiazol-3-yl |
| 1.608 | CH₃ | H | H | SO₂CH₃ | H | 5-Methyl-1,2,4-oxadiazol-3-yl |
| 1.609 | CH₃ | H | H | SO₂CH₃ | H | 5-Phenyl-1,2,4-oxadiazol-3-yl |
| 1.610 | CH₃ | H | H | SO₂CH₃ | H | 5-Phenyl-isoxazol-3-yl |
| 1.611 | CH₃ | H | H | SO₂CH₃ | H | 1-(4-Chlorophenyl)-1,2,4-triazol-2-yl |
| 1.612 | CH₃ | H | H | SO₂CH₃ | H | 5-Cyano-4,5-dihydro-isoxazol-3-yl |
| 1.613 | CH₃ | H | H | SO₂CH₃ | H | 5,6-Dihydro-4H-1,3-thiazin-2-yl |
| 1.614 | CH₃ | H | H | SO₂CH₃ | H | 1,3-Dithiolan-2-yl |
| 1.615 | CH₃ | H | H | SO₂CH₃ | H | 1,3-Dioxolan-2yl |
| 1.616 | CH₃ | H | H | SO₂CH₃ | H | 1,3-Dithian-2-yl |
| 1.617 | CH₃ | H | H | SO₂CH₃ | H | 1,3-Dioxan-2-yl |
| 1.618 | CH₃ | H | H | SO₂CH₃ | H | 1,3-Oxathiolan-2-yl |
| 1.619 | CH₃ | H | H | SO₂CH₃ | H | 1,2,4-Triazol-1-yl |
| 1.620 | CH₃ | H | H | SO₂CH₃ | H | 3-Methyl-1,2,4-thiadiazol-5-yl |
| 1.621 | CH₃ | H | H | SO₂CH₃ | H | 1,2,4-Thiadiazol-5-yl |
| 1.622 | CH₃ | H | H | SO₂CH₃ | H | Thiazoline-4,5-dion-2-yl |
| 1.623 | CH₃ | H | H | SO₂CH₃ | H | 3-Oxo-3-H-1,2,4-dithiazol-5-yl |
| 1.624 | CH₃ | H | H | SO₂CH₃ | H | 2-Oxo-2-H-1,3,4-dithiazol-5-yl |
| 1.625 | CH₃ | H | H | SO₂CH₃ | Cl | 2-Thienyl |
| 1.626 | CH₃ | H | H | SO₂CH₃ | Cl | 3-Thienyl |
| 1.627 | CH₃ | H | H | SO₂CH₃ | Cl | 2-Furyl |
| 1.628 | CH₃ | H | H | SO₂CH₃ | Cl | 3-Furyl |
| 1.629 | CH₃ | H | H | SO₂CH₃ | Cl | 3-Methyl-isoxazol-5-yl |
| 1.630 | CH₃ | H | H | SO₂CH₃ | Cl | 5-Thiazolyl |
| 1.631 | CH₃ | H | H | SO₂CH₃ | Cl | 4-Thiazolyl |
| 1.632 | CH₃ | H | H | SO₂CH₃ | Cl | 2-Thiazolyl |
| 1.633 | CH₃ | H | H | SO₂CH₃ | Cl | 3-Methyl-isothiazol-5-yl |
| 1.634 | CH₃ | H | H | SO₂CH₃ | Cl | 3-Isoxazolyl |
| 1.635 | CH₃ | H | H | SO₂CH₃ | Cl | 5-Phenyl-thiazol-2-yl |
| 1.636 | CH₃ | H | H | SO₂CH₃ | Cl | 2-Pyridyl |
| 1.637 | CH₃ | H | H | SO₂CH₃ | Cl | 3-Pyridyl |
| 1.638 | CH₃ | H | H | SO₂CH₃ | Cl | 4-Pyridyl |
| 1.639 | CH₃ | H | H | SO₂CH₃ | Cl | 1-Methyl-2-pyrrolyl |
| 1.640 | CH₃ | H | H | SO₂CH₃ | Cl | 1-Methyl-1,2,4-triazol-5-yl |
| 1.641 | CH₃ | H | H | SO₂CH₃ | Cl | 2-Benzthiazolyl |
| 1.642 | CH₃ | H | H | SO₂CH₃ | Cl | 2-Quinolyl |
| 1.643 | CH₃ | H | H | SO₂CH₃ | Cl | 1-Methyl-benzimidazol-2-yl |
| 1.644 | CH₃ | H | H | SO₂CH₃ | Cl | 2-Oxazolyl |
| 1.645 | CH₃ | H | H | SO₂CH₃ | Cl | 1-Phenyl-pyrazol-5-yl |
| 1.646 | CH₃ | H | H | SO₂CH₃ | Cl | 1-Methyl-pyrazol-3-yl |
| 1.647 | CH₃ | H | H | SO₂CH₃ | Cl | 1-Methyl-pyrazol-5-yl |
| 1.648 | CH₃ | H | H | SO₂CH₃ | Cl | 1,3-Dimethyl-pyrazol-3-yl |
| 1.649 | CH₃ | H | H | SO₂CH₃ | Cl | 1-Phenyl-pyrazol-3-yl |
| 1.650 | CH₃ | H | H | SO₂CH₃ | Cl | 1,4-Dimethyl-pyrazol-5-yl |
| 1.651 | CH₃ | H | H | SO₂CH₃ | Cl | 1,3-Dimethyl-pyrazol-4-yl |
| 1.652 | CH₃ | H | H | SO₂CH₃ | Cl | 1,5-Dimethyl-pyrazol-4-yl |
| 1.653 | CH₃ | H | H | SO₂CH₃ | Cl | 1-Methyl-pyrazol-4-yl |
| 1.654 | CH₃ | H | H | SO₂CH₃ | Cl | 1,3-Dimethyl-pyrazol-5-yl |
| 1.655 | CH₃ | H | H | SO₂CH₃ | Cl | 4-Methyl-oxazol-2-yl |
| 1.656 | CH₃ | H | H | SO₂CH₃ | Cl | 5-Methylthio-thiazGl-2-yl |
| 1.657 | CH₃ | H | H | SO₂CH₃ | Cl | 4-Methoxy-1-methyl-pyrazol-5-yl |
| 1.658 | CH₃ | H | H | SO₂CH₃ | Cl | 3-Cyclopropyl-isoxazol-5-yl |
| 1.659 | CH₃ | H | H | SO₂CH₃ | Cl | 3-Isopropyl-isoxazol-5-yl |
| 1.660 | CH₃ | H | H | SO₂CH₃ | Cl | (3-Methyl-phenyl)-thiazol-2-yl |
| 1.661 | CH₃ | H | H | SO₂CH₃ | Cl | 5-Methyl-thiazol-2-yl |

TABLE 1-continued

Compounds of the structure Id

| No. | R³ | R⁴ | R⁵ | L | M | Z |
|---|---|---|---|---|---|---|
| 1.662 | CH₃ | H | H | SO₂CH₃ | Cl | 4-Bromo-2-thienyl |
| 1.663 | CH₃ | H | H | SO₂CH₃ | Cl | 5-Methyl-2-thienyl |
| 1.664 | CH₃ | H | H | SO₂CH₃ | Cl | 4-Methyl-2-thienyl |
| 1.665 | CH₃ | H | H | SO₂CH₃ | Cl | 4-Methyl-thiazol-2-yl |
| 1.666 | CH₃ | H | H | SO₂CH₃ | Cl | 4-Chloro-thiazol-2-yl |
| 1.667 | CH₃ | H | H | SO₂CH₃ | Cl | 4,5-Dimethyl-thiazol-2-yl |
| 1.668 | CH₃ | H | H | SO₂CH₃ | Cl | 4-Phenyl-thiazol-2-yl |
| 1.669 | CH₃ | H | H | SO₂CH₃ | Cl | 2-Methoxy-thiazol-5-yl |
| 1.670 | CH₃ | H | H | SO₂CH₃ | Cl | 4-Methyl-2-pyridyl |
| 1.671 | CH₃ | H | H | SO₂CH₃ | Cl | 6-(2-Methoxyethyl)-2-pyridyl |
| 1.672 | CH₃ | H | H | SO₂CH₃ | Cl | 6-Methylthio-2-pyridyl |
| 1.673 | CH₃ | H | H | SO₂CH₃ | Cl | 6-Methoxy-3-pyridyl |
| 1.674 | CH₃ | H | H | SO₂CH₃ | Cl | 6-Methoxy-2-pyridyl |
| 1.675 | CH₃ | H | H | SO₂CH₃ | Cl | 6-Methyl-2-pyridyl |
| 1.676 | CH₃ | H | H | SO₂CH₃ | Cl | 6-(2,2,2-Trifluoroethoxy)-2-pyridyl |
| 1.677 | CH₃ | H | H | SO₂CH₃ | Cl | 6-(2,2,2-Trifluoroethoxy)-3-pyridyl |
| 1.678 | CH₃ | H | H | SO₂CH₃ | Cl | 5-Pyrimidinyl |
| 1.679 | CH₃ | H | H | SO₂CH₃ | Cl | 6-Dimethylamino-3-pyridyl |
| 1.680 | CH₃ | H | H | SO₂CH₃ | Cl | 1,2,4-Thiadiazol-5-yl |
| 1.681 | CH₃ | H | H | SO₂CH₃ | Cl | 3-Ethoxycarbonyl-1-methyl-pyrazol-5-yl |
| 1.682 | CH₃ | H | H | SO₂CH₃ | Cl | 2-Methylthio-pyrimidin-5-yl |
| 1.683 | CH₃ | H | H | SO₂CH₃ | Cl | 2-Pyrimidinyl |
| 1.684 | CH₃ | H | H | SO₂CH₃ | Cl | 2-Methylthio-pyrimidin-4-yl |
| 1.685 | CH₃ | H | H | SO₂CH₃ | Cl | 5-Methylthio-1,3,4-thiadiazol-2-yl |
| 1.686 | CH₃ | H | H | SO₂CH₃ | Cl | 5-Methoxy-1,3,4-thiadiazol-2-yl |
| 1.687 | CH₃ | H | H | SO₂CH₃ | Cl | 4,5-Dihydro-thiazol-2-yl |
| 1.688 | CH₃ | H | H | SO₂CH₃ | Cl | 5-Methyl-oxazol-2-yl |
| 1.689 | CH₃ | H | H | SO₂CH₃ | Cl | 5-Phenyl-oxazol-2-yl |
| 1.690 | CH₃ | H | H | SO₂CH₃ | Cl | 2-Methyl-oxazol-5-yl |
| 1.691 | CH₃ | H | H | SO₂CH₃ | Cl | 2-Phenyl-oxazol-5-yl |
| 1.692 | CH₃ | H | H | SO₂CH₃ | Cl | 2-Methyl-1,3,4-oxa-diazol-5-yl |
| 1.693 | CH₃ | H | H | SO₂CH₃ | Cl | 2-Phenyl-1,3,4-oxa-diazol-5-yl |
| 1.694 | CH₃ | H | H | SO₂CH₃ | Cl | 5-Trifluoromethyl-1,2,4-oxadiazol-3-yl |
| 1.695 | CH₃ | H | H | SO₂CH₃ | Cl | 5-Methyl-1,2,4-oxadiazol-3-yl |
| 1.696 | CH₃ | H | H | SO₂CH₃ | Cl | 5-Phenyl-1,2,4-oxadiazol-3-yl |
| 1.697 | CH₃ | H | H | SO₂CH₃ | Cl | 5-Phenyl-isoxazol-3-yl |
| 1.698 | CH₃ | H | H | SO₂CH₃ | Cl | 1-(4-Chlorophenyl)-1,2,4-triazol-2-yl |
| 1.699 | CH₃ | H | H | SO₂CH₃ | Cl | 5-Cyano-4,5-dihydro-isoxazol-3-yl |
| 1.700 | CH₃ | H | H | SO₂CH₃ | Cl | 5,6-Dihydro-4H-1,3-thiazin-2-yl |
| 1.701 | CH₃ | H | H | SO₂CH₃ | Cl | 1,3-Dithiolan-2-yl |
| 1.702 | CH₃ | H | H | SO₂CH₃ | Cl | 1,3-Dioxolan-2yl |
| 1.703 | CH₃ | H | H | SO₂CH₃ | Cl | 1,3-Dithian-2-yl |
| 1.704 | CH₃ | H | H | SO₂CH₃ | Cl | 1,3-Dioxan-2-yl |
| 1.705 | CH₃ | H | H | SO₂CH₃ | Cl | 1,3-Oxathiolan-2-yl |
| 1.706 | CH₃ | H | H | SO₂CH₃ | Cl | 1,2,4-Triazol-1-yl |
| 1.707 | CH₃ | H | H | SO₂CH₃ | Cl | 3-Methyl-1,2,4-thiadiazol-5-yl |
| 1.708 | CH₃ | H | H | SO₂CH₃ | Cl | 1,2,4-Thiadiazol-5-yl |
| 1.709 | CH₃ | H | H | SO₂CH₃ | Cl | Thiazolin-4,5-dion-2-yl |
| 1.710 | CH₃ | H | H | SO₂CH₃ | Cl | 3-oxo-3-H-1,2,4-dithiazol-5-yl |
| 1.711 | CH₃ | H | H | SO₂CH₃ | Cl | 2-oxo-2-H-1,3,4-dithiazol-5-yl |
| 1.712 | CH₃ | H | H | SO₂CH₃ | CH₃ | 2-Thienyl |
| 1.713 | CH₃ | H | H | SO₂CH₃ | CH₃ | 3-Thienyl |
| 1.714 | CH₃ | H | H | SO₂CH₃ | CH₃ | 2-Furyl |
| 1.715 | CH₃ | H | H | SO₂CH₃ | CH₃ | 3-Furyl |
| 1.716 | CH₃ | H | H | SO₂CH₃ | CH₃ | 3-Methyl-isoxazol-5-yl |
| 1.717 | CH₃ | H | H | SO₂CH₃ | CH₃ | 5-Thiazolyl |
| 1.718 | CH₃ | H | H | SO₂CH₃ | CH₃ | 4-Thiazolyl |
| 1.719 | CH₃ | H | H | SO₂CH₃ | CH₃ | 2-Thiazolyl |
| 1.720 | CH₃ | H | H | SO₂CH₃ | CH₃ | 3-Methyl-isothiazol-5-yl |
| 1.721 | CH₃ | H | H | SO₂CH₃ | CH₃ | 3-Isoxazolyl |
| 1.722 | CH₃ | H | H | SO₂CH₃ | CH₃ | 5-Phenyl-thiazol-2-yl |
| 1.723 | CH₃ | H | H | SO₂CH₃ | CH₃ | 2-Pyridyl |
| 1.724 | CH₃ | H | H | SO₂CH₃ | CH₃ | 3-Pyridyl |
| 1.725 | CH₃ | H | H | SO₂CH₃ | CH₃ | 4-Pyridyl |
| 1.726 | CH₃ | H | H | SO₂CH₃ | CH₃ | 1-Methyl-2-pyrrolyl |

TABLE 1-continued

Compounds of the structure Id

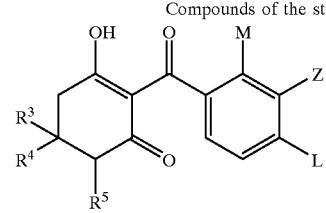

Id

| No. | R³ | R⁴ | R⁵ | L | M | Z |
|---|---|---|---|---|---|---|
| 1.727 | CH₃ | H | H | SO₂CH₃ | CH₃ | 1-Methyl-1,2,4-triazol-5-yl |
| 1.728 | CH₃ | H | H | SO₂CH₃ | CH₃ | 2-8enzthiazolyl |
| 1.729 | CH₃ | H | H | SO₂CH₃ | CH₃ | 2-Quinolyl |
| 1.730 | CH₃ | H | H | SO₂CH₃ | CH₃ | 1-Methyl-benzimidazol-2-yl |
| 1.731 | CH₃ | H | H | SO₂CH₃ | CH₃ | 2-Oxazolyl |
| 1.732 | CH₃ | H | H | SO₂CH₃ | CH₃ | 1-Phenyl-pyrazol-5-yl |
| 1.733 | CH₃ | H | H | SO₂CH₃ | CH₃ | 1-Methyl-pyrazol-3-yl |
| 1.734 | CH₃ | H | H | SO₂CH₃ | CH₃ | 1-Methyl-pyrazol-5-yl |
| 1.735 | CH₃ | H | H | SO₂CH₃ | CH₃ | 1,3-Dimethyl-pyrazol-3-yl |
| 1.736 | CH₃ | H | H | SO₂CH₃ | CH₃ | 1-Phenyl-pyrazol-3-yl |
| 1.737 | CH₃ | H | H | SO₂CH₃ | CH₃ | 1,4-Dimethyl-pyrazol-5-yl |
| 1.738 | CH₃ | H | H | SO₂CH₃ | CH₃ | 1,3-Dimethyl-pyrazol-4-yl |
| 1.739 | CH₃ | H | H | SO₂CH₃ | CH₃ | 1,5-Dimethyl-pyrazol-4-yl |
| 1.740 | CH₃ | H | H | SO₂CH₃ | CH₃ | 1-Methyl-pyrazol-4-yl |
| 1.741 | CH₃ | H | H | SO₂CH₃ | CH₃ | 1,3-Dimethyl-pyrazol-5-yl |
| 1.742 | CH₃ | H | H | SO₂CH₃ | CH₃ | 4-Methyl-oxazol-2-yl |
| 1.743 | CH₃ | H | H | SO₂CH₃ | CH₃ | 5-Methylthio-thiazol-2-yl |
| 1.744 | CH₃ | H | H | SO₂CH₃ | CH₃ | 4-Methoxy-1-methyl-pyrazol-5-yl |
| 1.745 | CH₃ | H | H | SO₂CH₃ | CH₃ | 3-Cyclopropyl-isoxazol-5-yl |
| 1.746 | CH₃ | H | H | SO₂CH₃ | CH₃ | 3-Isopropyl-isoxazol-5-yl |
| 1.747 | CH₃ | H | H | SO₂CH₃ | CH₃ | (3-Methyl-phenyl)-thiazol-2-yl |
| 1.748 | CH₃ | H | H | SO₂CH₃ | CH₃ | 5-Methyl-thiazol-2-yl |
| 1.749 | CH₃ | H | H | SO₂CH₃ | CH₃ | 4-Bromo-2-thienyl |
| 1.750 | CH₃ | H | H | SO₂CH₃ | CH₃ | 5-Methyl-2-thienyl |
| 1.751 | CH₃ | H | H | SO₂CH₃ | CH₃ | 4-Methyl-2-thienyl |
| 1.752 | CH₃ | H | H | SO₂CH₃ | CH₃ | 4-Methyl-thiazol-2-yl |
| 1.753 | CH₃ | H | H | SO₂CH₃ | CH₃ | 4-Chloro-thiazol-2-yl |
| 1.754 | CH₃ | H | H | SO₂CH₃ | CH₃ | 4,5-Dimethyl-thiazol-2-yl |
| 1.755 | CH₃ | H | H | SO₂CH₃ | CH₃ | 4-Phenyl-thiazol-2-yl |
| 1.756 | CH₃ | H | H | SO₂CH₃ | CH₃ | 2-Methoxy-thiazol-5-yl |
| 1.757 | CH₃ | H | H | SO₂CH₃ | CH₃ | 4-Methyl-2-pyridyl |
| 1.758 | CH₃ | H | H | SO₂CH₃ | CH₃ | 6-(2-Methoxyethyl)-2-pyridyl |
| 1.759 | CH₃ | H | H | SO₂CH₃ | CH₃ | 6-Methylthio-2-pyridyl |
| 1.760 | CH₃ | H | H | SO₂CH₃ | CH₃ | 6-Methoxy-3-pyridyl |
| 1.761 | CH₃ | H | H | SO₂CH₃ | CH₃ | 6-Methoxy-2-pyridyl |
| 1.762 | CH₃ | H | H | SO₂CH₃ | CH₃ | 6-Methyl-2-pyridyl |
| 1.763 | CH₃ | W | H | SO₂CH₃ | CH₃ | 6-(2,2,2-Trifluoroethoxy)-2-pyridyl |
| 1.764 | CH₃ | H | H | SO₂CH₃ | CH₃ | 6-(2,2,2-Trifluoroethoxy)-3-pyridyl |
| 1.765 | CH₃ | H | H | SO₂CH₃ | CH₃ | 5-Pyrimidinyl |
| 1.766 | CH₃ | H | H | SO₂CH₃ | CH₃ | 6-Dimethylamino-3-pyridyl |
| 1.767 | CH₃ | H | H | SO₂CH₃ | CH₃ | 1,2,4-Thiadiazol-5-yl |
| 1.768 | CH₃ | H | H | SO₂CH₃ | CH₃ | 3-Ethoxycarbonyl-1-methyl-pyrazol-5-yl |
| 1.769 | CH₃ | H | H | SO₂CH₃ | CH₃ | 2-Methylthio-pyrimidin-5-yl |
| 1.770 | CH₃ | H | H | SO₂CH₃ | CH₃ | 2-Pyrimidinyl |
| 1.771 | CH₃ | H | H | SO₂CH₃ | CH₃ | 2-Methylthio-pyrimidin-4-yl |
| 1.772 | CH₃ | H | H | SO₂CH₃ | CH₃ | 5-Methylthio-1,3,4-thiadiazol-2-yl |
| 1.773 | CH₃ | H | H | SO₂CH₃ | CH₃ | 5-Methoxy-1,3,4-thiadiazol-2-yl |
| 1.774 | CH₃ | H | H | SO₂CH₃ | CH₃ | 4,5-Dihydro-thiazol-2-yl |
| 1.775 | CH₃ | H | H | SO₂CH₃ | CH₃ | 5-Methyl-oxazol-2-yl |
| 1.776 | CH₃ | H | H | SO₂CH₃ | CH₃ | 5-Phenyl-oxazol-2-yl |
| 1.777 | CH₃ | H | H | SO₂CH₃ | CH₃ | 2-Methyl-oxazol-5-yl |
| 1.778 | CH₃ | H | H | SO₂CH₃ | CH₃ | 2-Phenyl-oxazol-5-yl |
| 1.779 | CH₃ | H | H | SO₂CH₃ | CH₃ | 2-Methyl-1,3,4-oxa-diazol-5-yl |
| 1.780 | CH₃ | H | H | SO₂CH₃ | CH₃ | 2-Phenyl-1,3,4-oxa-diazol-5-yl |
| 1.781 | CH₃ | H | H | SO₂CH₃ | CH₃ | 5-Trifluoromethyl-1,2,4-oxadiazol-3-yl |
| 1.782 | CH₃ | H | H | SO₂CH₃ | CH₃ | 5-Methyl-1,2,4-oxadiazol-3-yl |
| 1.783 | CH₃ | H | H | SO₂CH₃ | CH₃ | 5-Phenyl-1,2,4-oxadiazol-3-yl |
| 1.784 | CH₃ | H | H | SO₂CH₃ | CH₃ | 5-Phenyl-isoxazol-3-yl |
| 1.785 | CH₃ | H | H | SO₂CH₃ | CH₃ | 1-(4-Chlorophenyl)-1,2,4-triazol-2-yl |
| 1.786 | CH₃ | H | H | SO₂CH₃ | CH₃ | 5-Cyano-4,5-dihydro-isoxazol-3-yl |
| 1.787 | CH₃ | H | H | SO₂CH₃ | CH₃ | 5,6-Dihydro-4H-1,3-thiazin-2-yl |
| 1.788 | CH₃ | H | H | SO₂CH₃ | CH₃ | 1,3-Dithiolan-2-yl |
| 1.789 | CH₃ | H | H | SO₂CH₃ | CH₃ | 1,3-Dioxolan-2-yl |
| 1.790 | CH₃ | H | H | SO₂CH₃ | CH₃ | 1,3-Dithian-2-yl |
| 1.791 | CH₃ | H | H | SO₂CH₃ | CH₃ | 1,3-Dioxan-2-yl |

TABLE 1-continued

Compounds of the structure Id

| No. | R³ | R⁴ | R⁵ | L | M | Z |
|---|---|---|---|---|---|---|
| 1.792 | CH₃ | H | H | SO₂CH₃ | CH₃ | 1,3-Oxathiolan-2-yl |
| 1.793 | CH₃ | H | H | SO₂CH₃ | CH₃ | 1,2,4-Triazol-1-yl |
| 1.794 | CH₃ | H | H | SO₂CH₃ | CH₃ | 3-Methyl-1,2,4-thiadiazol-5-yl |
| 1.795 | CH₃ | H | H | SO₂CH₃ | CH₃ | 1,2,4-Thiadiazol-5-yl |
| 1.796 | CH₃ | H | H | SO₂CH₃ | CH₃ | Thiazoline-4,5-dion-2-yl |
| 1.797 | CH₃ | H | H | SO₂CH₃ | CH₃ | 3-oxo-3-H-1,2,4-dithiazol-5-yl |
| 1.798 | CH₃ | H | H | SO₂CH₃ | CH₃ | 2-Oxo-2-H-1,3,4-dithiazol-5-yl |
| 1.799 | CH₃ | CH₃ | H | SO₂CH₃ | CH₃ | 2-Thienyl |
| 1.800 | CH₃ | CH₃ | H | SO₂CH₃ | CH₃ | 3-Thienyl |
| 1.801 | CH₃ | CH₃ | H | SO₂CH₃ | CH₃ | 2-Furyl |
| 1.802 | CH₃ | CH₃ | H | SO₂CH₃ | CH₃ | 3-Furyl |
| 1.803 | CH₃ | CH₃ | H | SO₂CH₃ | CH₃ | 3-Methyl-isoxazol-5-yl |
| 1.804 | CH₃ | CH₃ | H | SO₂CH₃ | CH₃ | 5-Thiazolyl |
| 1.805 | CH₃ | CH₃ | H | SO₂CH₃ | CH₃ | 4-Thiazolyl |
| 1.806 | CH₃ | CH₃ | H | SO₂CH₃ | CH₃ | 2-Thiazolyl |
| 1.807 | CH₃ | CH₃ | H | SO₂CH₃ | CH₃ | 3-Methyl-isothiazol-5-yl |
| 1.808 | CH₃ | CH₃ | H | SO₂CH₃ | CH₃ | 3-Isoxazolyl |
| 1.809 | CH₃ | CH₃ | H | SO₂CH₃ | CH₃ | 5-Phenyl-thiazol-2-yl |
| 1.810 | CH₃ | CH₃ | H | SO₂CH₃ | CH₃ | 2-Pyridyl |
| 1.811 | CH₃ | CH₃ | H | SO₂CH₃ | CH₃ | 3-Pyridyl |
| 1.812 | CH₃ | CH₃ | H | SO₂CH₃ | CH₃ | 4-Pyridyl |
| 1.813 | CH₃ | CH₃ | H | SO₂CH₃ | CH₃ | 1-Methyl-2-pyrrolyl |
| 1.814 | CH₃ | CH₃ | H | SO₂CH₃ | CH₃ | 1-Methyl-1,2,4-triazol-5-yl |
| 1.815 | CH₃ | CH₃ | H | SO₂CH₃ | CH₃ | 2-Benzthiazolyl |
| 1.816 | CH₃ | CH₃ | H | SO₂CH₃ | CH₃ | 2-Quinolyl |
| 1.817 | CH₃ | CH₃ | H | SO₂CH₃ | CH₃ | 1-Methyl-benzimidazol-2-yl |
| 1.818 | CH₃ | CH₃ | H | SO₂CH₃ | CH₃ | 2-Oxazolyl |
| 1.819 | CH₃ | CH₃ | H | SO₂CH₃ | CH₃ | 1-Phenyl-pyrazol-5-yl |
| 1.820 | CH₃ | CH₃ | H | SO₂CH₃ | CH₃ | 1-Methyl-pyrazol-3-yl |
| 1.821 | CH₃ | CH₃ | H | SO₂CH₃ | CH₃ | 1-Methyl-pyrazol-5-yl |
| 1.822 | CH₃ | CH₃ | H | SO₂CH₃ | CH₃ | 1,3-Dimethyl-pyrazol-3-yl |
| 1.823 | CH₃ | CH₃ | H | SO₂CH₃ | CH₃ | 1-Phenyl-pyrazol-3-yl |
| 1.824 | CH₃ | CH₃ | H | SO₂CH₃ | CH₃ | 1,4-Dimethyl-pyrazol-5-yl |
| 1.825 | CH₃ | CH₃ | H | SO₂CH₃ | CH₃ | 1,3-Dimethyl-pyrazol-4-yl |
| 1.826 | CH₃ | CH₃ | H | SO₂CH₃ | CH₃ | 1,5-Dimethyl-pyrazol-4-yl |
| 1.827 | CH₃ | CH₃ | H | SO₂CH₃ | CH₃ | 1-Methyl-pyrazol-4-yl |
| 1.828 | CH₃ | CH₃ | H | SO₂CH₃ | CH₃ | 1,3-Dimethyl-pyrazol-5-yl |
| 1.829 | CH₃ | CH₃ | H | SO₂CH₃ | CH₃ | 4-Methyl-oxazol-2-yl |
| 1.830 | CH₃ | CH₃ | H | SO₂CH₃ | CH₃ | 5-Methylthio-thiazol-2-yl |
| 1.831 | CH₃ | CH₃ | H | SO₂CH₃ | CH₃ | 4-Methoxy-1-methyl-pyrazol-5-yl |
| 1.832 | CH₃ | CH₃ | H | SO₂CH₃ | CH₃ | 3-Cyclopropyl-isoxazol-5-yl |
| 1.833 | CH₃ | CH₃ | H | SO₂CH₃ | CH₃ | 3-Isopropyl-isoxazol-5-yl |
| 1.834 | CH₃ | CH₃ | H | SO₂CH₃ | CH₃ | (3-Methyl-phenyl)-thiazol-2-yl |
| 1.835 | CH₃ | CH₃ | H | SO₂CH₃ | CH₃ | 5-Methyl-thiazol-2-yl |
| 1.836 | CH₃ | CH₃ | H | SO₂CH₃ | CH₃ | 4-Bromo-2-thienyl |
| 1.837 | CH₃ | CH₃ | H | SO₂CH₃ | CH₃ | 5-Methyl-2-thienyl |
| 1.838 | CH₃ | CH₃ | H | SO₂CH₃ | CH₃ | 4-Methyl-2-thienyl |
| 1.839 | CH₃ | CH₃ | H | SO₂CH₃ | CH₃ | 4-Methyl-thiazol-2-yl |
| 1.840 | CH₃ | CH₃ | H | SO₂CH₃ | CH₃ | 4-Chloro-thiazol-2-yl |
| 1.841 | CH₃ | CH₃ | H | SO₂CH₃ | CH₃ | 4,5-Dimethyl-thiazol-2-yl |
| 1.842 | CH₃ | CH₃ | H | SO₂CH₃ | CH₃ | 4-Phenyl-thiazol-2-yl |
| 1.843 | CH₃ | CH₃ | H | SO₂CH₃ | CH₃ | 2-Methoxy-thiazol-5-yl |
| 1.844 | CH₃ | CH₃ | H | SO₂CH₃ | CH₃ | 4-Methyl-2-pyridyl |
| 1.845 | CH₃ | CH₃ | H | SO₂CH₃ | CH₃ | 6-(2-Methoxyethyl)-2-pyridyl |
| 1.846 | CH₃ | CH₃ | H | SO₂CH₃ | CH₃ | 6-Methylthio-2-pyridyl |
| 1.847 | CH₃ | CH₃ | H | SO₂CH₃ | CH₃ | 6-Methoxy-3-pyridyl |
| 1.848 | CH₃ | CH₃ | H | SO₂CH₃ | CH₃ | 6-Methoxy-2-pyridyl |
| 1.849 | CH₃ | CH₃ | H | SO₂CH₃ | CH₃ | 6-Methyl-2-pyridyl |
| 1.850 | CH₃ | CH₃ | H | SO₂CH₃ | CH₃ | 6-(2,2,2-Trifluoroethoxy)-2-pyridyl |
| 1.851 | CH₃ | CH₃ | H | SO₂CH₃ | CH₃ | 6-(2,2,2-Trifluoroethoxy)-3-pyridyl |
| 1.852 | CH₃ | CH₃ | H | SO₂CH₃ | CH₃ | 5-Pyrimidinyl |
| 1.853 | CH₃ | CH₃ | H | SO₂CH₃ | CH₃ | 6-Dimethylamino-3-pyridyl |
| 1.854 | CH₃ | CH₃ | H | SO₂CH₃ | CH₃ | 1,2,4-Thiadiazol-5-yl |
| 1.855 | CH₃ | CH₃ | H | SO₂CH₃ | CH₃ | 3-Ethoxycarbonyl-1-methyl-pyrazol-5-yl |
| 1.856 | CH₃ | CH₃ | H | SO₂CH₃ | CH₃ | 2-Methylthio-pyrimidin-5-yl |

TABLE 1-continued

Compounds of the structure Id

| No. | R³ | R⁴ | R⁵ | L | M | Z |
|---|---|---|---|---|---|---|
| 1.857 | CH₃ | CH₃ | H | SO₂CH₃ | CH₃ | 2-Pyrimidinyl |
| 1.858 | CH₃ | CH₃ | H | SO₂CH₃ | CH₃ | 2-Methylthio-pyrimidin-4-yl |
| 1.859 | CH₃ | CH₃ | H | SO₂CH₃ | CH₃ | 5-Methylthio-1,3,4-thiadiazol-2-yl |
| 1.860 | CH₃ | CH₃ | H | SO₂CH₃ | CH₃ | 5-Methoxy-1,3,4-thiadiazol-2-yl |
| 1.861 | CH₃ | CH₃ | H | SO₂CH₃ | CH₃ | 4,5-Dihydro-thiazol-2-yl |
| 1.862 | CH₃ | CH₃ | H | SO₂CH₃ | CH₃ | 5-Methyl-oxazol-2-yl |
| 1.863 | CH₃ | CH₃ | H | SO₂CH₃ | CH₃ | 5-Phenyl-oxazol-2-yl |
| 1.864 | CH₃ | CH₃ | H | SO₂CH₃ | CH₃ | 2-Methyl-oxazol-5-yl |
| 1.865 | CH₃ | CH₃ | H | SO₂CH₃ | CH₃ | 2-Phenyl-oxazol-5-yl |
| 1.666 | CH₃ | CH₃ | H | SO₂CH₃ | CH₃ | 2-Methyl-1,3,4-oxa-diazol-5-yl |
| 1.867 | CH₃ | CH₃ | H | SO₂CH₃ | CH₃ | 2-Phenyl-1,3,4-oxa-diazol-5-yl |
| 1.868 | CH₃ | CH₃ | H | SO₂CH₃ | CH₃ | 5-Trifluoromethyl-1,2,4-oxadiazol-3-yl |
| 1.869 | CH₃ | CH₃ | H | SO₂CH₃ | CH₃ | 5-Methyl-1,2,4-oxadiazol-3-yl |
| 1.870 | CH₃ | CH₃ | H | SO₂CH₃ | CH₃ | 5-Phenyl-1,2,4-oxadiazol-3-yl |
| 1.871 | CH₃ | CH₃ | H | SO₂CH₃ | CH₃ | 5-Phenyl-isoxazol-3-yl |
| 1.872 | CH₃ | CH₃ | H | SO₂CH₃ | CH₃ | 1-(4-Chlorophenyl)-1,2,4-triazol-2-yl |
| 1.873 | CH₃ | CH₃ | H | SO₂CH₃ | CH₃ | 5-Cyano-4,5-dihydro-isoxazol-3-yl |
| 1.874 | CH₃ | CH₃ | H | SO₂CH₃ | CH₃ | 5,6-Dihydro-4H-1,3-thiazin-2-yl |
| 1.875 | CH₃ | CH₃ | H | SO₂CH₃ | CH₃ | 1,3-Dithiolan-2-yl |
| 1.876 | CH₃ | CH₃ | H | SO₂CH₃ | CH₃ | 1,3-Dioxblan-2-yl |
| 1.877 | CH₃ | CH₃ | H | SO₂CH₃ | CH₃ | 1,3-Dithian-2-yl |
| 1.878 | CH₃ | CH₃ | H | SO₂CH₃ | CH₃ | 1,3-Dioxan-2-yl |
| 1.879 | CH₃ | CH₃ | H | SO₂CH₃ | CH₃ | 1,3-Oxathiolan-2-yl |
| 1.880 | CH₃ | CH₃ | H | SO₂CH₃ | CH₃ | 1,2,4-Triazol-1-yl |
| 1.881 | CH₃ | CH₃ | H | SO₂CH₃ | CH₃ | 3-Methyl-1,2,4-thiadiazol-5-yl |
| 1.882 | CH₃ | CH₃ | H | SO₂CH₃ | CH₃ | 1,2,4-Thiadiazol-5-yl |
| 1.883 | CH₃ | CH₃ | H | SO₂CH₃ | CH₃ | Thiazoline-4,5-dion-2-yl |
| 1.884 | CH₃ | CH₃ | H | SO₂CH₃ | CH₃ | 3-Oxo-3-H-1,2,4-dithiazol-5-yl |
| 1.885 | CH₃ | CH₃ | H | SO₂CH₃ | CH₃ | 2-Oxo-2-H-1,3,4-dithiazol-5-yl |
| 1.886 | CH₃ | CH₃ | H | SO₂CH₃ | Cl | 2-Thienyl |
| 1.887 | CH₃ | CH₃ | H | SO₂CH₃ | Cl | 3-Thienyl |
| 1.888 | CH₃ | CH₃ | H | SO₂CH₃ | Cl | 2-Furyl |
| 1.889 | CH₃ | CH₃ | H | SO₂CH₃ | Cl | 3-Furyl |
| 1.890 | CH₃ | CH₃ | H | SO₂CH₃ | Cl | 3-Methyl-isoxazol-5-yl |
| 1.891 | CH₃ | CH₃ | H | SO₂CH₃ | Cl | 5-Thiazolyl |
| 1.892 | CH₃ | CH₃ | H | SO₂CH₃ | Cl | 4-Thiazolyl |
| 1.893 | CH₃ | CH₃ | H | SO₂CH₃ | Cl | 2-Thiazolyl |
| 1.894 | CH₃ | CH₃ | H | SO₂CH₃ | Cl | 3-Methyl-isothiazol-5-yl |
| 1.895 | CH₃ | CH₃ | H | SO₂CH₃ | Cl | 3-Isoxazolyl |
| 1.896 | CH₃ | CH₃ | H | SO₂CH₃ | Cl | 5-Phenyl-thiazol-2-yl |
| 1.897 | CH₃ | CH₃ | H | SO₂CH₃ | Cl | 2-Pyridyl |
| 1.898 | CH₃ | CH₃ | H | SO₂CH₃ | Cl | 3-Pyridyl |
| 1.899 | CH₃ | CH₃ | H | SO₂CH₃ | Cl | 4-Pyridyl |
| 1.900 | CH₃ | CH₃ | H | SO₂CH₃ | Cl | 1-Methyl-2-pyrrolyl |
| 1.901 | CH₃ | CH₃ | H | SO₂CH₃ | Cl | 1-Methyl-1,2,4-triazol-5-yl |
| 1.902 | CH₃ | CH₃ | H | SO₂CH₃ | Cl | 2-Benzthiazolyl |
| 1.903 | CH₃ | CH₃ | H | SO₂CH₃ | Cl | 2-Quinolyl |
| 1.904 | CH₃ | CH₃ | H | SO₂CH₃ | Cl | 1-Methyl-benzimidazol-2-yl |
| 1.905 | CH₃ | CH₃ | H | SO₂CH₃ | Cl | 2-Oxazolyl |
| 1.906 | CH₃ | CH₃ | H | SO₂CH₃ | Cl | 1-Phenyl-pyrazol-5-yl |
| 1.907 | CH₃ | CH₃ | H | SO₂CH₃ | Cl | 1-Methyl-pyrazol-3-yl |
| 1.908 | CH₃ | CH₃ | H | SO₂CH₃ | Cl | 1-Methyl-pyrazol-5-yl |
| 1.909 | CH₃ | CH₃ | H | SO₂CH₃ | Cl | 1,3-Dimethyl-pyrazol-3-yl |
| 1.910 | CH₃ | CH₃ | H | SO₂CH₃ | Cl | 1-Phenyl-pyrazol-3-yl |
| 1.911 | CH₃ | CH₃ | H | SO₂CH₃ | Cl | 1,4-Dimethyl-pyrazol-5-yl |
| 1.912 | CH₃ | CH₃ | H | SO₂CH₃ | Cl | 1,3-Dimethyl-pyrazol-4-yl |
| 1.913 | CH₃ | CH₃ | H | SO₂CH₃ | Cl | 1,5-Dimethyl-pyrazol-4-yl |
| 1.914 | CH₃ | CH₃ | H | SO₂CH₃ | Cl | 1-Methyl-pyrazol-4-yl |
| 1.915 | CH₃ | CH₃ | H | SO₂CH₃ | Cl | 1,3-Dimethyl-pyrazol-5-yl |
| 1.916 | CH₃ | CH₃ | H | SO₂CH₃ | Cl | 4-Methyl-oxazol-2-yl |
| 1.917 | CH₃ | CH₃ | H | SO₂CH₃ | Cl | 5-Methylthio-thiazol-2-yl |
| 1.918 | CH₃ | CH₃ | H | SO₂CH₃ | Cl | 4-Methoxy-1-methyl-pyrazol-5-yl |
| 1.919 | CH₃ | CH₃ | H | SO₂CH₃ | Cl | 3-Cyclopropyl-isoxazol-5-yl |
| 1.920 | CH₃ | CH₃ | H | SO₂CH₃ | Cl | 3-Isopropyl-isoxazol-5-yl |
| 1.921 | CH₃ | CH₃ | H | SO₂CH₃ | Cl | (3-Methyl-phenyl)-thiazol-2-yl |

TABLE 1-continued

Compounds of the structure Id

| No. | R³ | R⁴ | R⁵ | L | M | Z |
|---|---|---|---|---|---|---|
| 1.922 | CH₃ | CH₃ | H | SO₂CH₃ | Cl | 5-Methyl-thiazol-2-yl |
| 1.923 | CH₃ | CH₃ | H | SO₂CH₃ | Cl | 4-Bromo-2-thienyl |
| 1.924 | CH₃ | CH₃ | H | SO₂CH₃ | Cl | 5-Methyl-2-thienyl |
| 1.925 | CH₃ | CH₃ | H | SO₂CH₃ | Cl | 4-Methyl-2-thienyl |
| 1.926 | CH₃ | CH₃ | H | SO₂CH₃ | Cl | 4-Methyl-thiazol-2-yl |
| 1.927 | CH₃ | CH₃ | H | SO₂CH₃ | Cl | 4-Chloro-thiazol-2-yl |
| 1.928 | CH₃ | CH₃ | H | SO₂CH₃ | Cl | 4,5-Dimethyl-thiazol-2-yl |
| 1.929 | CH₃ | CH₃ | H | SO₂CH₃ | Cl | 4-Phenyl-thiazol-2-yl |
| 1.930 | CH₃ | CH₃ | H | SO₂CH₃ | Cl | 2-Methoxy-thiazol-5-yl |
| 1.931 | CH₃ | CH₃ | H | SO₂CH₃ | Cl | 4-Methyl-2-pyridyl |
| 1.932 | CH₃ | CH₃ | H | SO₂CH₃ | Cl | 6-(2-Methoxyethyl)-2-pyridyl |
| 1.933 | CH₃ | CH₃ | H | SO₂CH₃ | Cl | 6-Methylthio-2-pyridyl |
| 1.934 | CH₃ | CH₃ | H | SO₂CH₃ | Cl | 6-Methoxy-3-pyridyl |
| 1.935 | CH₃ | CH₃ | H | SO₂CH₃ | Cl | 6-Methoxy-2-pyridyl |
| 1.936 | CH₃ | CH₃ | H | SO₂CH₃ | Cl | 6-Methyl-2-pyridyl |
| 1.937 | CH₃ | CH₃ | H | SO₂CH₃ | Cl | 6-(2,2,2-Trifluoroethoxy)-2-pyridyl |
| 1.938 | CH₃ | CH₃ | H | SO₂CH₃ | Cl | 6-(2,2,2-Trifluoroethoxy)-3-pyridyl |
| 1.939 | CH₃ | CH₃ | H | SO₂CH₃ | Cl | 5-Pyrimidinyl |
| 1.940 | CH₃ | CH₃ | H | SO₂CH₃ | Cl | 6-Dimethylamino-3-pyridyl |
| 1.941 | CH₃ | CH₃ | H | SO₂CH₃ | Cl | 1,2,4-Thiadiazol-5-yl |
| 1.942 | CH₃ | CH₃ | H | SO₂CH₃ | Cl | 3-Ethoxycarbonyl-1-methyl-pyrazol-5-yl |
| 1.943 | CH₃ | CH₃ | H | SO₂CH₃ | Cl | 2-Methylthio-pyrimidin-5-yl |
| 1.944 | CH₃ | CH₃ | H | SO₂CH₃ | Cl | 2-Pyrimidinyl |
| 1.945 | CH₃ | CH₃ | H | SO₂CH₃ | Cl | 2-Methylthio-pyrimidin-4-yl |
| 1.946 | CH₃ | CH₃ | H | SO₂CH₃ | Cl | 5-Methylthio-1,3,4-thiadiazol-2-yl |
| 1.947 | CH₃ | CH₃ | H | SO₂CH₃ | Cl | 5-Methoxy-1,3,4-thiadiazol-2-yl |
| 1.948 | CH₃ | CH₃ | H | SO₂CH₃ | Cl | 4,5-Dihydro-thiazol-2-yl |
| 1.949 | CH₃ | CH₃ | H | SO₂CH₃ | Cl | 5-Methyl-oxazol-2-yl |
| 1.950 | CH₃ | CH₃ | H | SO₂CH₃ | Cl | 5-Phenyl-oxazol-2-yl |
| 1.951 | CH₃ | CH₃ | H | SO₂CH₃ | Cl | 2-Methyl-oxazol-5-yl |
| 1.952 | CH₃ | CH₃ | H | SO₂CH₃ | Cl | 2-Phenyl-oxazol-5-yl |
| 1.953 | CH₃ | CH₃ | H | SO₂CH₃ | Cl | 2-Methyl-1,3,4-oxa-diazol-5-yl |
| 1.954 | CH₃ | CH₃ | H | SO₂CH₃ | Cl | 2-Phenyl-1,3,4-oxa-diazol-5-yl |
| 1.955 | CH₃ | CH₃ | H | SO₂CH₃ | Cl | 5-Trifluoromethyl-1,2,4-oxadiazol-3-yl |
| 1.956 | CH₃ | CH₃ | H | SO₂CH₃ | Cl | 5-Methyl-1,2,4-oxadiazol-3-yl |
| 1.957 | CH₃ | CH₃ | H | SO₂CH₃ | Cl | 5-Phenyl-1,2,4-oxadiazol-3-yl |
| 1.958 | CH₃ | CH₃ | H | SO₂CH₃ | Cl | 5-Phenyl-isoxazol-3-yl |
| 1.959 | CH₃ | CH₃ | H | SO₂CH₃ | Cl | 1-(4-Chlorophenyl)-1,2,4-triazol-2-yl |
| 1.960 | CH₃ | CH₃ | H | SO₂CH₃ | Cl | 5-Cyano-4,5-dihydro-isoxazol-3-yl |
| 1.961 | CH₃ | CH₃ | H | SO₂CH₃ | Cl | 5,6-Dihydro-4H-1,3-thiazin-2-yl |
| 1.962 | CH₃ | CH₃ | H | SO₂CH₃ | Cl | 1,3-Dithiolan-2-yl |
| 1.963 | CH₃ | CH₃ | H | SO₂CH₃ | Cl | 1,3-Dioxolan-2-yl |
| 1.964 | CH₃ | CH₃ | H | SO₂CH₃ | Cl | 1,3-Dithian-2-yl |
| 1.965 | CH₃ | CH₃ | H | SO₂CH₃ | Cl | 1,3-Dioxan-2-yl |
| 1.966 | CH₃ | CH₃ | H | SO₂CH₃ | Cl | 1,3-Oxathiolan-2-yl |
| 1.967 | CH₃ | CH₃ | H | SO₂CH₃ | Cl | 1,2,4-Triazol-1-yl |
| 1.968 | CH₃ | CH₃ | H | SO₂CH₃ | Cl | 3-Methyl-1,2,4-thiadiazol-5-yl |
| 1.969 | CH₃ | CH₃ | H | SO₂CH₃ | Cl | 1,2,4-Thiadiazol-5-yl |
| 1.970 | CH₃ | CH₃ | H | SO₂CH₃ | Cl | Thiazoline-4,5-dion-2-yl |
| 1.971 | CH₃ | CH₃ | H | SO₂CH₃ | Cl | 3-Oxo-3-H-1,2,4-dithiazol-5-yl |
| 1.972 | CH₃ | CH₃ | H | SO₂CH₃ | Cl | 2-Oxo-2-H-1,3,4-dithiazol-5-yl |
| 1.973 | CH₃ | CH₃ | H | SO₂CH₃ | H | 2-Thienyl |
| 1.974 | CH₃ | CH₃ | H | SO₂CH₃ | H | 3-Thienyl |
| 1.975 | CH₃ | CH₃ | H | SO₂CH₃ | H | 2-Furyl |
| 1.976 | CH₃ | CH₃ | H | SO₂CH₃ | H | 3-Furyl |
| 1.977 | CH₃ | CH₃ | H | SO₂CH₃ | H | 3-Methyl-isoxazol-5-yl |
| 1.978 | CH₃ | CH₃ | H | SO₂CH₃ | H | 5-Thiazolyl |
| 1.979 | CH₃ | CH₃ | H | SO₂CH₃ | H | 4-Thiazolyl |
| 1.980 | CH₃ | CH₃ | H | SO₂CH₃ | H | 2-Thiazolyl |
| 1.981 | CH₃ | CH₃ | H | SO₂CH₃ | H | 3-Methyl-isothiazol-5-yl |
| 1.982 | CH₃ | CH₃ | H | SO₂CH₃ | H | 3-Isoxazolyl |
| 1.983 | CH₃ | CH₃ | H | SO₂CH₃ | H | 5-Phenyl-thiazol-2-yl |
| 1.984 | CH₃ | CH₃ | H | SO₂CH₃ | H | 2-Pyridyl |
| 1.985 | CH₃ | CH₃ | H | SO₂CH₃ | H | 3-Pyridyl |
| 1.986 | CH₃ | CH₃ | H | SO₂CH₃ | H | 4-Pyridyl |

TABLE 1-continued

Compounds of the structure Id

| No. | R³ | R⁴ | R⁵ | L | M | Z |
|---|---|---|---|---|---|---|
| 1.987 | CH₃ | CH₃ | H | SO₂CH₃ | H | 1-Methyl-2-pyrrolyl |
| 1.988 | CH₃ | CH₃ | H | SO₂CH₃ | H | 1-Methyl-1,2,4-triazol-5-yl |
| 1.989 | CH₃ | CH₃ | H | SO₂CH₃ | H | 2-Benzthiazolyl |
| 1.990 | CH₃ | CH₃ | H | SO₂CH₃ | H | 2-Quinolyl |
| 1.991 | CH₃ | CH₃ | H | SO₂CH₃ | H | 1-Methyl-benzimidazol-2-yl |
| 1.992 | CH₃ | CH₃ | H | SO₂CH₃ | H | 2-Oxazolyl |
| 1.993 | CH₃ | CH₃ | H | SO₂CH₃ | H | 1-Phenyl-pyrazol-5-yl |
| 1.994 | CH₃ | CH₃ | H | SO₂CH₃ | H | 1-Methyl-pyrazol-3-yl |
| 1.995 | CH₃ | CH₃ | H | SO₂CH₃ | H | 1-Methyl-pyrazol-5-yl |
| 1.996 | CH₃ | CH₃ | H | SO₂CH₃ | H | 1,3-Dimethyl-pyrazol-3-yl |
| 1.997 | CH₃ | CH₃ | H | SO₂CH₃ | H | 1-Phenyl-pyrazol-3-yl |
| 1.998 | CH₃ | CH₃ | H | SO₂CH₃ | H | 1,4-Dimethyl-pyrazol-5-yl |
| 1.999 | CH₃ | CH₃ | H | SO₂CH₃ | H | 1,3-Dimethyl-pyrazol-4-yl |
| 1.1000 | CH₃ | CH₃ | H | SO₂CH₃ | H | 1,5-Dimethyl-pyrazol-4-yl |
| 1.1001 | CH₃ | CH₃ | H | SO₂CH₃ | H | 1-Methyl-pyrazol-4-yl |
| 1.1002 | CH₃ | CH₃ | H | SO₂CH₃ | H | 1,3-Dimethyl-pyrazol-5-yl |
| 1.1003 | CH₃ | CH₃ | H | SO₂CH₃ | H | 4-Methyl-oxazol-2-yl |
| 1.1004 | CH₃ | CH₃ | H | SO₂CH₃ | H | 5-Methylthio-thiazol-2-yl |
| 1.1005 | CH₃ | CH₃ | H | SO₂CH₃ | H | 4-Methoxy-1-methyl-pyrazol-5-yl |
| 1.1006 | CH₃ | CH₃ | H | SO₂CH₃ | H | 3-Cyclopropyl-isoxazol-5-yl |
| 1.1007 | CH₃ | CH₃ | H | SO₂CH₃ | H | 3-Isopropyl-isoxazol-5-yl |
| 1.1008 | CH₃ | CH₃ | H | SO₂CH₃ | H | (3-Methyl-phenyl)-thiazol-2-yl |
| 1.1009 | CH₃ | CH₃ | H | SO₂CH₃ | H | 5-Methyl-thiazol-2-yl |
| 1.1010 | CH₃ | CH₃ | H | SO₂CH₃ | H | 4-Bromo-2-thienyl |
| 1.1011 | CH₃ | CH₃ | H | SO₂CH₃ | H | 5-Methyl-2-thienyl |
| 1.1012 | CH₃ | CH₃ | H | SO₂CH₃ | H | 4-Methyl-2-thienyl |
| 1.1013 | CH₃ | CH₃ | H | SO₂CH₃ | H | 4-Methyl-thiazol-2-yl |
| 1.1014 | CH₃ | CH₃ | H | SO₂CH₃ | H | 4-Chloro-thiazol-2-yl |
| 1.1015 | CH₃ | CH₃ | H | SO₂CH₃ | H | 4,5-Dimethyl-thiazol-2-yl |
| 1.1016 | CH₃ | CH₃ | H | SO₂CH₃ | H | 4-Phenyl-thiazol-2-yl |
| 1.1017 | CH₃ | CH₃ | H | SO₂CH₃ | H | 2-Methoxy-thiazol-5-yl |
| 1.1018 | CH₃ | CH₃ | H | SO₂CH₃ | H | 4-Methyl-2-pyridyl |
| 1.1019 | CH₃ | CH₃ | H | SO₂CH₃ | H | 6-(2-Methoxyethyl)-2-pyridyl |
| 1.1020 | CH₃ | CH₃ | H | SO₂CH₃ | H | 6-Methylthio-2-pyridyl |
| 1.1021 | CH₃ | CH₃ | H | SO₂CH₃ | H | 6-Methoxy-3-pyridyl |
| 1.1022 | CH₃ | CH₃ | H | SO₂CH₃ | H | 6-Methoxy-2-pyridyl |
| 1.1023 | CH₃ | CH₃ | H | SO₂CH₃ | H | 6-Methyl-2-pyridyl |
| 1.1024 | CH₃ | CH₃ | H | SO₂CH₃ | H | 6-(2,2,2-Trifluoroethoxy)-2-pyridyl |
| 1.1025 | CH₃ | CH₃ | H | SO₂CH₃ | H | 6-(2,2,2-Trifluoroethoxy)-3-pyridyl |
| 1.1026 | CH₃ | CH₃ | H | SO₂CH₃ | H | 5-Pyriinidinyl |
| 1.1027 | CH₃ | CH₃ | H | SO₂CH₃ | H | 6-Dimethylamino-3-pyridyl |
| 1.1028 | CH₃ | CH₃ | H | SO₂CH₃ | H | 1,2,4-Thiadiazol-5-yl |
| 1.1029 | CH₃ | CH₃ | H | SO₂CH₃ | H | 3-Ethoxycarbonyl-1-methyl-pyrazol-5-yl |
| 1.1030 | CH₃ | CH₃ | H | SO₂CH₃ | H | 2-Methylthio-pyrimidin-5-yl |
| 1.1031 | CH₃ | CH₃ | H | SO₂CH₃ | H | 2-Pyrimidinyl |
| 1.1032 | CH₃ | CH₃ | H | SO₂CH₃ | H | 2-Methylthio-pyriinidin-4-yl |
| 1.1033 | CH₃ | CH₃ | H | SO₂CH₃ | H | 5-Methylthio-1,3,4-thiadiazol-2-yl |
| 1.1034 | CH₃ | CH₃ | H | SO₂CH₃ | H | 5-Methoxy-1,3,4-thiadiazol-2-yl |
| 1.1035 | CH₃ | CH₃ | H | SO₂CH₃ | H | 4,5-Dihydro-thiazol-2-yl |
| 1.1036 | CH₃ | CH₃ | H | SO₂CH₃ | H | 5-Methyl-oxazol-2-yl |
| 1.1037 | CH₃ | CH₃ | H | SO₂CH₃ | H | 5-Phenyl-oxazol-2-yl |
| 1.1038 | CH₃ | CH₃ | H | SO₂CH₃ | H | 2-Methyl-oxazol-5-yl |
| 1.1039 | CH₃ | CH₃ | H | SO₂CH₃ | H | 2-Phenyl-oxazol-5-yl |
| 1.1040 | CH₃ | CH₃ | H | SO₂CH₃ | H | 2-Methyl-1,3,4-oxa-diazol-5-yl |
| 1.1041 | CH₃ | CH₃ | H | SO₂CH₃ | H | 2-Phenyl-1,3,4-oxa-diazol-5-yl |
| 1.1042 | CH₃ | CH₃ | H | SO₂CH₃ | H | 5-Trifluoromethyl-1,2,4-oxadiazol-3-yl |
| 1.1043 | CH₃ | CH₃ | H | SO₂CH₃ | H | 5-Methyl-1,2,4-oxadiazol-3-yl |
| 1.1044 | CH₃ | CH₃ | H | SO₂CH₃ | H | 5-Phenyl-1,2,4-oxadiazol-3-yl |
| 1.1045 | CH₃ | CH₃ | H | SO₂CH₃ | H | 5-Phenyl-isoxazol-3-yl |
| 1.1046 | CH₃ | CH₃ | H | SO₂CH₃ | H | 1-(4-Chlorophenyl)-1,2,4-triazol-2-yl |
| 1.1047 | CH₃ | CH₃ | H | SO₂CH₃ | H | 5-Cyano-4,5-dihydro-isoxazol-3-yl |
| 1.1048 | CH₃ | CH₃ | H | SO₂CH₃ | H | 5,6-Dihydro-4H-1,3-thiazin-2-yl |
| 1.1049 | CH₃ | CH₃ | H | SO₂CH₃ | H | 1,3-Dithiolan-2-yl |
| 1.1050 | CH₃ | CH₃ | H | SO₂CH₃ | H | 1,3-Dioxolan-2-yl |
| 1.1051 | CH₃ | CH₃ | H | SO₂CH₃ | H | 1,3-Dithian-2-yl |

TABLE 1-continued

Compounds of the structure Id

| No. | R³ | R⁴ | R⁵ | L | M | Z |
|---|---|---|---|---|---|---|
| 1.1052 | CH₃ | CH₃ | H | SO₂CH₃ | H | 1,3-Dioxan-2-yl |
| 1.1053 | CH₃ | CH₃ | H | SO₂CH₃ | H | 1,3-Oxathiolan-2-yl |
| 1.1054 | CH₃ | CH₃ | H | SO₂CH₃ | H | 1,2,4-Triazol-1-yl |
| 1.1055 | CH₃ | CH₃ | H | SO₂CH₃ | H | 3-Methyl-1,2,4-thiadiazol-5-yl |
| 1.1056 | CH₃ | CH₃ | H | SO₂CH₃ | H | 1,2,4-Thiadiazol-5-yl |
| 1.1057 | CH₃ | CH₃ | H | SO₂CH₃ | H | Thiazoline-4,5-dion-2-yl |
| 1.1058 | CH₃ | CH₃ | H | SO₂CH₃ | H | 3-Oxo-3-H-1,2,4-dithiazol-5-yl |
| 1.1059 | CH₃ | CH₃ | H | SO₂CH₃ | H | 2-Oxo-2-H-1,3,4-dithiazol-5-yl |
| 1.1060 | H | H | H | CF₃ | Cl | 2-Thienyl |
| 1.1061 | H | H | H | CF₃ | Cl | 3-Thienyl |
| 1.1062 | H | H | H | CF₃ | Cl | 2-Furyl |
| 1.1063 | H | H | H | CF₃ | Cl | 3-Furyl |
| 1.1064 | H | H | H | CF₃ | Cl | 3-Methyl-isoxazol-5-yl |
| 1.1065 | H | H | H | CF₃ | Cl | 5-Thiazolyl |
| 1.1066 | H | H | H | CF₃ | Cl | 4-Thiazolyl |
| 1.1067 | H | H | H | CF₃ | Cl | 2-Thiazolyl |
| 1.1068 | H | H | H | CF₃ | Cl | 3-Isoxazolyl |
| 1.1069 | H | H | H | CF₃ | Cl | 2-Pyridyl |
| 1.1070 | H | H | H | CF₃ | Cl | 3-Pyridyl |
| 1.1071 | H | H | H | CF₃ | Cl | 4-Pyridyl |
| 1.1072 | H | H | H | CF₃ | Cl | 2-Benzthiazolyl |
| 1.1073 | H | H | H | CF₃ | Cl | 2-Quinolyl |
| 1.1074 | H | H | H | CF₃ | Cl | 4-Methyl-oxazol-2-yl |
| 1.1075 | H | H | H | CF₃ | Cl | 5-Pyrimidinyl |
| 1.1076 | H | H | H | OCH₃ | Cl | 2-Thienyl |
| 1.1077 | H | H | H | OCH₃ | Cl | 3-Thienyl |
| 1.1078 | H | H | H | OCH₃ | Cl | 2-Furyl |
| 1.1079 | H | H | H | OCH₃ | Cl | 3-Furyl |
| 1.1080 | H | H | H | OCH₃ | Cl | 3-Methyl-isoxazol-5-yl |
| 1.1081 | H | H | H | OCH₃ | Cl | 5-Thiazolyl |
| 1.1082 | H | H | H | OCH₃ | Cl | 4-Thiazolyl |
| 1.1083 | H | H | R | OCH₃ | Cl | 2-Thiazolyl |
| 1.1084 | H | H | H | OCH₃ | Cl | 3-Isoxazolyl |
| 1.1085 | H | H | H | OCH₃ | CX | 2-Pyridyl |
| 1.1086 | H | H | H | OCH₃ | Cl | 3-Pyridyl |
| 1.1087 | H | H | H | OCH₃ | Cl | 4-Pyridyl |
| 1.1088 | H | H | H | OCH₃ | Cl | 2-Benzthiazolyl |
| 1.1089 | H | H | H | OCH₃ | Cl | 2-Quinolyl |
| 1.1090 | H | H | H | OCH₃ | Cl | 4-Methyl-oxazol-2-yl |
| 1.1091 | H | H | H | OCH₃ | Cl | 5-Pyrimidinyl |
| 1.1092 | H | H | H | OCF₃ | Cl | 2-Thienyl |
| 1.1093 | H | H | H | OCF₃ | Cl | 3-Thienyl |
| 1.1094 | H | H | H | OCF₃ | Cl | 2-Furyl |
| 1.1095 | H | H | H | OCF₃ | Cl | 3-Furyl |
| 1.1096 | H | H | H | OCF₃ | Cl | 3-Methyl-isoxazol-5-yl |
| 1.1097 | H | H | H | OCF₃ | Cl | 5-Thiazolyl |
| 1.1098 | H | H | H | OCF₃ | Cl | 4-Thiazolyl |
| 1.1099 | H | H | H | OCF₃ | Cl | 2-Thiazolyl |
| 1.1100 | H | H | H | OCF₃ | Cl | 3-Isoxazolyl |
| 1.1101 | H | H | H | OCF₃ | Cl | 2-Pyridyl |
| 1.1102 | H | H | H | OCF₃ | Cl | 3-Pyridyl |
| 1.1103 | H | H | H | OCF₃ | Cl | 4-Pyridyl |
| 1.1104 | H | H | H | OCF₃ | Cl | 2-Benzthiazolyl |
| 1.1105 | H | H | H | OCF₃ | Cl | 2-Quinolyl |
| 1.1106 | H | H | H | OCF₃ | Cl | 4-Methyl-oxazol-2-yl |
| 1.1107 | H | H | H | OCF₃ | Cl | 5-Pyrimidinyl |
| 1.1108 | H | H | H | SO₂NHCH₃ | Cl | 2-Thienyl |
| 1.1109 | H | H | H | SO₂NHCH₃ | Cl | 3-Thienyl |
| 1.1110 | H | H | H | SO₂NHCH₃ | Cl | 2-Furyl |
| 1.1111 | H | H | H | SO₂NHCH₃ | Cl | 3-Furyl |
| 1.1112 | H | H | H | SO₂NHCH₃ | Cl | 3-Methyl-isoxazol-5-yl |
| 1.1113 | H | H | H | SO₂NHCH₃ | Cl | 5-Thiaz9lyl |
| 1.1114 | H | H | H | SO₂NHCH₃ | Cl | 4-Thiazolyl |
| 1.1115 | H | H | H | SO₂NHCH₃ | Cl | 2-Thiazolyl |
| 1.1116 | H | H | H | SO₂NHCH₃ | Cl | 3-Isoxazolyl |

TABLE 1-continued

Compounds of the structure Id

| No. | R³ | R⁴ | R⁵ | L | M | Z |
|---|---|---|---|---|---|---|
| 1.1117 | H | H | H | SO₂NHCH₃ | Cl | 2-Pyridyl |
| 1.1118 | H | H | H | SO₂NHCH₃ | Cl | 3-Pyridyl |
| 1.1119 | H | H | H | SO₂NHCH₃ | Cl | 4-Pyridyl |
| 1.1120 | H | H | H | SO₂NHCH₃ | Cl | 2-Benzthiazolyl |
| 1.1121 | H | H | H | SO₂NHCH₃ | Cl | 2-Quinolyl |
| 1.1122 | H | H | H | SO₂NHCH₃ | Cl | 4-Methyl-oxazol-2-yl |
| 1.1123 | H | H | H | SO₂NHCH₃ | Cl | 5-Pyrimidinyl |
| 1.1124 | H | H | H | NHSO₂CH₃ | Cl | 2-Thienyl |
| 1.1125 | H | H | H | NHSO₂CH₃ | Cl | 3-Thienyl |
| 1.1126 | H | H | H | NHSO₂CH₃ | Cl | 2-Furyl |
| 1.1127 | H | H | H | NHSO₂CH₃ | Cl | 3-Furyl |
| 1.1128 | H | H | H | NHSO₂CH₃ | Cl | 3-Methyl-isoxazol-5-yl |
| 1.1129 | H | H | H | NHSO₂CH₃ | Cl | 5-Thiazolyl |
| 1.1130 | H | H | H | NHSO₂CH₃ | Cl | 4-Thiazolyl |
| 1.1131 | H | H | H | NHSO₂CH₃ | Cl | 2-Thiazolyl |
| 1.1132 | H | H | H | NHSO₂CH₃ | Cl | 3-Isoxazolyl |
| 1.1133 | H | H | H | NHSO₂CH₃ | Cl | 2-Pyridyl |
| 1.1134 | H | H | H | NHSO₂CH₃ | Cl | 3-Pyridyl |
| 1.1135 | H | H | H | NHSO₂CH₃ | Cl | 4-Pyridyl |
| 1.1136 | H | H | H | NHSO₂CH₃ | Cl | 2-Benzthiazolyl |
| 1.1137 | H | H | H | NHSO₂CH₃ | Cl | 2-Quinolyl |
| 1.1138 | H | H | H | NHSO₂CH₃ | Cl | 4-Methyl-oxazol-2-yl |
| 1.1139 | H | H | H | NHSO₂CH₃ | Cl | 5-Pyrimidinyl |
| 1.1140 | H | H | H | OSO₂CH₃ | Cl | 2-Thienyl |
| 1.1141 | H | H | H | OSO₂CH₃ | Cl | 3-Thienyl |
| 1.1142 | H | H | H | OSO₂CH₃ | Cl | 2-Furyl |
| 1.1143 | H | H | H | OSO₂CH₃ | Cl | 3-Furyl |
| 1.1144 | H | H | H | OSO₂CH₃ | Cl | 3-Methyl-isoxazol-5-yl |
| 1.1145 | H | H | H | OSO₂CH₃ | Cl | 5-Thiazolyl |
| 1.1146 | H | H | H | OSO₂CH₃ | Cl | 4-Thiazolyl |
| 1.1147 | H | H | H | OSO₂CH₃ | Cl | 2-Thiazolyl |
| 1.1148 | H | H | H | OSO₂CH₃ | Cl | 3-Isoxazolyl |
| 1.1149 | H | H | H | OSO₂CH₃ | Cl | 2-Pyridyl |
| 1.1150 | H | H | H | OSO₂CH₃ | Cl | 3-Pyridyl |
| 1.1151 | H | H | H | OSO₂CH₃ | Cl | 4-Pyridyl |
| 1.1152 | H | H | H | OSO₂CH₃ | Cl | 2-Benzthiazolyl |
| 1.1153 | H | H | H | OSO₂CH₃ | Cl | 2-Quinolyl |
| 1.1154 | H | H | H | OSO₂CH₃ | Cl | 4-Methyl-oxazol-2-yl |
| 1.1155 | H | H | H | OSO₂CH₃ | Cl | 5-Pyrimidinyl |
| 1.1156 | H | H | H | OCOCH₃ | Cl | 2-Thienyl |
| 1.1157 | H | H | H | OCOCH₃ | Cl | 3-Thienyl |
| 1.1158 | H | H | H | OCOCH₃ | Cl | 2-Furyl |
| 1.1159 | H | H | H | OCOCH₃ | Cl | 3-Furyl |
| 1.1160 | H | H | H | OCOCH₃ | qi | 3-Methyl-isoxazol-5-yl |
| 1.1161 | H | H | H | OCOCH₃ | Cl | 5-Thiazolyl |
| 1.1162 | H | H | H | OCOCH₃ | Cl | 4-Thiazolyl |
| 1.1163 | H | H | H | OCOCH₃ | Cl | 2-Thiazolyl |
| 1.1164 | H | H | H | OCOCH₃ | Cl | 3-Isoxazolyl |
| 1.1165 | H | H | H | OCOCH₃ | Cl | 2-Pyridyl |
| 1.1166 | H | H | H | OCOCH₃ | Cl | 3-Pyridyl |
| 1.1167 | H | H | H | OCOCH₃ | Cl | 4-Pyridyl |
| 1.1168 | H | H | H | OCOCH₃ | Cl | 2-Benzthiazolyl |
| 1.1169 | H | H | H | OCOCH₃ | Cl | 2-Quinolyl |
| 1.1170 | H | H | H | OCOCH₃ | Cl | 4-Methyl-oxazol-2-yl |
| 1.1171 | H | H | H | OCOCH₃ | Cl | 5-Pyrimidinyl |
| 1.1172 | H | H | H | SO₂CH₃ | OCH₃ | 2-Thienyl |
| 1.1173 | H | H | H | SO₂CH₃ | OCH₃ | 3-Thienyl |
| 1.1174 | H | H | H | SO₂CH₃ | OCH₃ | 2-Furyl |
| 1.1175 | H | H | H | SO₂CH₃ | OCH₃ | 3-Furyl |
| 1.1176 | H | H | H | SO₂CH₃ | OCH₃ | 3-Nethyl-isoxazol-5-yl |
| 1.1177 | H | H | H | SO₂CH₃ | OCH₃ | 5-Thiazolyl |
| 1.1178 | H | H | H | SO₂CH₃ | OCH₃ | 4-Thiazolyl |
| 1.1179 | H | H | H | SO₂CH₃ | OCH₃ | 2-Thiazolyl |
| 1.1180 | H | H | H | SO₂CH₃ | OCH₃ | 3-Isoxazolyl |
| 1.1181 | H | H | H | SO₂CH₃ | OCH₃ | 2-Pyridyl |

TABLE 1-continued

Compounds of the structure Id

| No. | R³ | R⁴ | R⁵ | L | M | Z |
|---|---|---|---|---|---|---|
| 1.1182 | H | H | H | SO₂CH₃ | OCH₃ | 3-Pyridyl |
| 1.1183 | H | H | H | SO₂CH₃ | OCH₃ | 4-Pyridyl |
| 1.1184 | H | H | H | SO₂CH₃ | OCH₃ | 2-Benzthiazolyl |
| 1.1185 | H | H | H | SO₂CH₃ | OCH₃ | 2-Quinolyl |
| 1.1186 | H | H | H | SO₂CH₃ | OCH₃ | 4-Methyl-oxazol-2-yl |
| 1.1187 | H | H | H | SO₂CH₃ | OCH₃ | 5-Pyrimidinyl |
| 1.1188 | H | H | H | SO₂CH₃ | CF₃ | 2-Thienyl |
| 1.1189 | H | H | H | SO₂CH₃ | CF₃ | 3-Thienyl |
| 1.1190 | H | H | H | SO₂CH₃ | CF₃ | 2-Furyl |
| 1.1191 | H | H | H | SO₂CH₃ | CF₃ | 3-Furyl |
| 1.1192 | H | H | H | SO₂CH₃ | CF₃ | 3-Methyl-isoxazol-5-yl |
| 1.1193 | H | H | H | SO₂CH₃ | CF₃ | 5-Thiazolyl |
| 1.1194 | H | H | H | SO₂CH₃ | CF₃ | 4-Thiazolyl |
| 1.1195 | H | H | H | SO₂CH₃ | CF₃ | 2-Thiazolyl |
| 1.1196 | H | H | H | SO₂CH₃ | CF₃ | 3-Isoxazolyl |
| 1.1197 | H | H | H | SO₂CH₃ | CF₃ | 2-Pyridyl |
| 1.1198 | H | H | H | SO₂CH₃ | CF₃ | 3-Pyridyl |
| 1.1199 | H | H | H | SO₂CH₃ | CF₃ | 4-Pyridyl |
| 1.1200 | H | H | H | SO₂CH₃ | CF₃ | 2-Benzthiazolyl |
| 1.1201 | H | H | H | SO₂CH₃ | CF₃ | 2-Quinolyl |
| 1.1202 | H | H | H | SO₂CH₃ | CF₃ | 4-Methyl-oxazol-2-yl |
| 1.1203 | H | H | H | SO₂CH₃ | CF₃ | 5-Pyrimidinyl |
| 1.1204 | H | H | H | SOCH₃ | Cl | 2-Thienyl |
| 1.1205 | H | H | H | SOCH₃ | Cl | 3-Thienyl |
| 1.1206 | H | H | H | SOCH₃ | Cl | 2-Furyl |
| 1.1207 | H | H | H | SOCH₃ | Cl | 3-Furyl |
| 1.1208 | H | H | H | SOCH₃ | Cl | 3-Methyl-isoxazol-5-yl |
| 1.1209 | H | H | H | SOCH₃ | Cl | 5-Thiazolyl |
| 1.1210 | H | H | H | SOCH₃ | Cl | 4-Thiazolyl |
| 1.1211 | H | H | H | SOCH₃ | Cl | 2-Thiazolyl |
| 1.1212 | H | H | H | SOCH₃ | Cl | 3-Isoxazolyl |
| 1.1213 | H | H | H | SOCH₃ | Cl | 2-Pyridyl |
| 1.1214 | H | H | H | SOCH₃ | Cl | 3-Pyridyl |
| 1.1215 | H | H | H | SOCH₃ | Cl | 4-Pyridyl |
| 1.1216 | H | H | H | SOCH₃ | Cl | 2-Benzthiazolyl |
| 1.1217 | H | H | H | SOCH₃ | Cl | 2-Quinolyl |
| 1.1218 | H | H | H | SOCH₃ | Cl | 4-Methyl-oxazol-2-yl |
| 1.1219 | H | H | H | SOCH₃ | Cl | 5-Pyrimidinyl |
| 1.1220 | H | H | H | SCH₃ | Cl | 2-Thienyl |
| 1.1221 | H | H | H | SCH₃ | Cl | 3-Thienyl |
| 1.1222 | H | H | H | SCH₃ | Cl | 2-Furyl |
| 1.1223 | H | H | H | SCH₃ | Cl | 3-Furyl |
| 1.1224 | H | H | H | SCH₃ | Cl | 3-Methyl-isoxazol-5-yl |
| 1.1225 | H | H | H | SCH₃ | Cl | 5-Thiazolyl |
| 1.1226 | H | H | H | SCH₃ | Cl | 4-Thiazolyl |
| 1.1227 | H | H | H | SCH₃ | Cl | 2-Thiazolyl |
| 1.1228 | H | H | H | SCH₃ | Cl | 3-Isoxazolyl |
| 1.1229 | H | H | H | SCH₃ | Cl | 2-Pyridyl |
| 1.1230 | H | H | H | SCH₃ | Cl | 3-Pyridyl |
| 1.1231 | H | H | H | SCH₃ | Cl | 4-Pyridyl |
| 1.1232 | H | H | H | SCH₃ | Cl | 2-Benzthiazolyl |
| 1.1233 | H | H | H | SCH₃ | Cl | 2-Quinolyl |
| 1.1234 | H | H | H | SCH₃ | Cl | 4-Methyl-oxazol-2-yl |
| 1.1235 | H | H | H | SCH₃ | Cl | 5-Pyrimidinyl |
| 1.1236 | H | H | H | SO₂C₂H₅ | Cl | 2-Thienyl |
| 1.1237 | H | H | H | SO₂C₂H₅ | Cl | 3-Thienyl |
| 1.1238 | H | H | H | SO₂C₂H₅ | Cl | 2-Furyl |
| 1.1239 | H | H | H | SO₂C₂H₅ | Cl | 3-Furyl |
| 1.1240 | H | H | H | SO₂C₂H₅ | Cl | 3-Methyl-isoxazol-5-yl |
| 1.1241 | H | H | H | SO₂C₂H₅ | Cl | 5-Thiazolyl |
| 1.1242 | H | H | H | SO₂C₂H₅ | Cl | 4-Thiazolyl |
| 1.1243 | H | H | H | SO₂C₂H₅ | Cl | 2-Thiazolyl |
| 1.1244 | H | H | H | SO₂C₂H₅ | Cl | 3-Isoxazolyl |
| 1.1245 | H | H | H | SO₂C₂H₅ | Cl | 2-Pyridyl |
| 1.1246 | H | H | H | SO₂C₂H₅ | Cl | 3-Pyridyl |

TABLE 1-continued

Compounds of the structure Id

| No. | R³ | R⁴ | R⁵ | L | M | Z |
|---|---|---|---|---|---|---|
| 1.1247 | H | H | H | SO₂C₂H₅ | Cl | 4-Pyridyl |
| 1.1248 | H | H | H | SO₂C₂H₅ | Cl | 2-Benzthiazolyl |
| 1.1249 | H | H | H | SO₂C₂H₅ | Cl | 2-Quinolyl |
| 1.1250 | H | H | H | SO₂C₂H₅ | Cl | 4-Methyl-oxazol-2-yl |
| 1.1251 | H | H | H | SO₂C₂H₅ | Cl | 5-Pyrimidinyl |
| 1.1252 | H | H | H | Cl | SO₂CH₃ | 2-Thienyl |
| 1.1253 | H | H | H | Cl | SO₂CH₃ | 3-Thienyl |
| 1.1254 | H | H | H | Cl | SO₂CH₃ | 2-Furyl |
| 1.1255 | H | H | H | Cl | SO₂CH₃ | 3-Furyl |
| 1.1256 | H | H | H | Cl | SO₂CH₃ | 3-Methyl-isoxazol-5-yl |
| 1.1257 | H | H | H | Cl | SO₂CH₃ | 5-Thiazolyl |
| 1.1258 | H | H | H | Cl | SO₂CH₃ | 4-Thiazolyl |
| 1.1259 | H | H | H | Cl | SO₂CH₃ | 2-Thiazolyl |
| 1.1260 | H | H | H | Cl | SO₂CH₃ | 3-Isoxazolyl |
| 1.1261 | H | H | H | Cl | SO₂CH₃ | 2-Pyridyl |
| 1.1262 | H | H | H | Cl | SO₂CH₃ | 3-Pyridyl |
| 1.1263 | H | H | H | Cl | SO₂CH₃ | 4-Pyridyl |
| 1.1264 | H | H | H | Cl | SO₂CH₃ | 2-Benzthiazolyl |
| 1.1265 | H | H | H | Cl | SO₂CH₃ | 2-Quinolyl |
| 1.1266 | H | H | H | Cl | SO₂CH₃ | 4-Methyl-oxazol-2-yl |
| 1.1267 | H | H | H | Cl | SO₂CH₃ | 5-Pyriinidinyl |
| 1.1268 | CH₃ | CH₃ | H | SO₂C₂H₅ | Cl | 2-Thienyl |
| 1.1269 | CH₃ | CH₃ | H | SO₂C₂H₅ | Cl | 3-Thienyl |
| 1.1270 | CH₃ | CH₃ | H | SO₂C₂H₅ | Cl | 2-Furyl |
| 1.1271 | CH₃ | CH₃ | H | SO₂C₂H₅ | Cl | 3-Furyl |
| 1.1272 | CH₃ | CH₃ | H | SO₂C₂H₅ | Cl | 3-Methyl-isoxazol-5-yl |
| 1.1273 | CH₃ | CH₃ | H | SO₂C₂H₅ | Cl | 5-Thiazolyl |
| 1.1274 | CH₃ | CH₃ | H | SO₂C₂H₅ | Cl | 4-Thiazolyl |
| 1.1275 | CH₃ | CH₃ | H | SO₂C₂H₅ | Cl | 2-Thiazolyl |
| 1.1276 | CH₃ | CH₃ | H | SO₂C₂H₅ | Cl | 3-Isoxazolyl |
| 1.1277 | CH₃ | CH₃ | H | SO₂C₂H₅ | Cl | 2-Pyridyl |
| 1.1278 | CH₃ | CH₃ | H | SO₂C₂H₅ | Cl | 3-Pyridyl |
| 1.1279 | CH₃ | CH₃ | H | SO₂C₂H₅ | Cl | 4-Pyridyl |
| 1.1280 | CH₃ | CH₃ | H | SO₂C₂H₅ | Cl | 2-Benzthiazolyl |
| 1.1281 | CH₃ | CH₃ | H | SO₂C₂H₅ | Cl | 2-Quinolyl |
| 1.1282 | CH₃ | CH₃ | H | SO₂C₂H₅ | Cl | 4-Methyl-oxazol-2-yl |
| 1.1283 | CH₃ | CH₃ | H | SO₂C₂H₅ | Cl | 5-Pyrimidinyl |
| 1.1284 | H | H | H | SO₂CH₃ | Cl | 5-Oxazolyl |
| 1.1285 | CH₃ | H | H | SO₂CH₃ | Cl | 5-Oxazolyl |
| 1.1286 | CH₃ | CH₃ | H | SO₂CH₃ | Cl | 5-Oxazolyl |

TABLE 2

Compounds of the structure Ie

| No. | R¹ | R² | R⁵ | L | M | Z |
|---|---|---|---|---|---|---|
| 2.1 | CH₃ | CH₃ | H | SO₂CH₃ | Cl | 2-Thienyl |
| 2.2 | CH₃ | CH₃ | H | SO₂CH₃ | Cl | 3-Thienyl |
| 2.3 | CH₃ | CH₃ | H | SO₂CH₃ | Cl | 2-Furyl |
| 2.4 | CH₃ | CH₃ | H | SO₂CH₃ | Cl | 3-Furyl |
| 2.5 | CH₃ | CH₃ | H | SO₂CH₃ | Cl | 3-Methyl-isoxazol-5-yl |
| 2.6 | CH₃ | CH₃ | H | SO₂CH₃ | Cl | 5-Thiazolyl |
| 2.7 | CH₃ | CH₃ | H | SO₂CH₃ | Cl | 4-Thiazolyl |
| 2.8 | CH₃ | CH₃ | H | SO₂CH₃ | Cl | 2-Thiazolyl |
| 2.9 | CH₃ | CH₃ | H | SO₂CH₃ | Cl | 3-Isoxazolyl |
| 2.10 | CH₃ | CH₃ | H | SO₂CH₃ | Cl | 2-Pyridyl |

TABLE 2-continued

Compounds of the structure Ie

| No. | R¹ | R² | R⁵ | L | M | Z |
|---|---|---|---|---|---|---|
| 2.11 | CH₃ | CH₃ | H | SO₂CH₃ | Cl | 3-Pyridyl |
| 2.12 | CH₃ | CH₃ | H | SO₂CH₃ | Cl | 4-Pyridyl |
| 2.13 | CH₃ | CH₃ | H | SO₂CH₃ | Cl | 2-Benzthiazolyl |
| 2.14 | CH₃ | CH₃ | H | SO₂CH₃ | Cl | 2-Quinolyl |
| 2.15 | CH₃ | CH₃ | H | SO₂CH₃ | Cl | 4-Methyl-oxazol-2-yl |
| 2.16 | CH₃ | CH₃ | H | SO₂CH₃ | Cl | 5-Pyrimidinyl |
| 2.17 | CH₃ | CH₃ | Br | SO₂CH₃ | Cl | 2-Thienyl |
| 2.18 | CH₃ | CH₃ | Br | SO₂CH₃ | Cl | 3-Thienyl |
| 2.19 | CH₃ | CH₃ | Br | SO₂CH₃ | Cl | 2-Furyl |
| 2.20 | CH₃ | CH₃ | Br | SO₂CH₃ | Cl | 3-Furyl |
| 2.21 | CH₃ | CH₃ | Br | SO₂CH₃ | Cl | 3-Methyl-isoxazol-5-yl |
| 2.22 | CH₃ | CH₃ | Br | SO₂CH₃ | Cl | 5-Thiazolyl |
| 2.23 | CH₃ | CH₃ | Br | SO₂CH₃ | Cl | 4-Thiazolyl |
| 2.24 | CH₃ | CH₃ | Br | SO₂CH₃ | Cl | 2-Thiazolyl |
| 2.25 | CH₃ | CH₃ | Br | SO₂CH₃ | Cl | 3-Isoxazolyl |
| 2.26 | CH₃ | CH₃ | Br | SO₂CH₃ | Cl | 2-Pyridyl |
| 2.27 | CH₃ | CH₃ | Br | SO₂CH₃ | Cl | 3-Pyridyl |
| 2.28 | CH₃ | CH₃ | Br | SO₂CH₃ | Cl | 4-Pyridyl |
| 2.29 | CH₃ | CH₃ | Br | SO₂CH₃ | Cl | 2-Benzthiazolyl |
| 2.30 | CH₃ | CH₃ | Br | SO₂CH₃ | Cl | 2-Quinolyl |
| 2.31 | CH₃ | CH₃ | Br | SO₂CH₃ | Cl | 4-Methyl-oxazol-2-yl |
| 2.32 | CH₃ | CH₃ | Br | SO₂CH₃ | Cl | 5-Pyrimidinyl |
| 2.33 | CH₃ | CH₃ | Cl | SO₂CH₃ | Cl | 2-Thienyl |
| 2.34 | CH₃ | CH₃ | Cl | SO₂CH₃ | Cl | 3-Thienyl |
| 2.35 | CH₃ | CH₃ | Cl | SO₂CH₃ | Cl | 2-Furyl |
| 2.36 | CH₃ | CH₃ | Cl | SO₂CH₃ | Cl | 3-Furyl |
| 2.37 | CH₃ | CH₃ | Cl | SO₂CH₃ | Cl | 3-Methyl-isoxazol-5-yl |
| 2.38 | CH₃ | CH₃ | Cl | SO₂CH₃ | Cl | 5-Thiazolyl |
| 2.39 | CH₃ | CH₃ | Cl | SO₂CH₃ | Cl | 4-Thiazolyl |
| 2.40 | CH₃ | CH₃ | Cl | SO₂CH₃ | Cl | 2-Thiazolyl |
| 2.41 | CH₃ | CH₃ | Cl | SO₂CH₃ | Cl | 3-Isoxazolyl |
| 2.42 | CH₃ | CH₃ | Cl | SO₂CH₃ | Cl | 2-Pyridyl |
| 2.43 | CH₃ | CH₃ | Cl | SO₂CH₃ | Cl | 3-Pyridyl |
| 2.44 | CH₃ | CH₃ | Cl | SO₂CH₃ | Cl | 4-Pyridyl |
| 2.45 | CH₃ | CH₃ | Cl | SO₂CH₃ | Cl | 2-Benzthiazolyl |
| 2.46 | CH₃ | CH₃ | Cl | SO₂CH₃ | Cl | 2-Quinolyl |
| 2.47 | CH₃ | CH₃ | Cl | SO₂CH₃ | Cl | 4-Methyl-oxazol-2-yl |
| 2.48 | CH₃ | CH₃ | Cl | SO₂CH₃ | Cl | 5-Pyrimidinyl |

TABLE 3

Compounds of the structure If

| No. | L | M | Z |
|---|---|---|---|
| 3.1 | SO₂CH₃ | Cl | 2-Thienyl |
| 3.2 | SO₂CH₃ | Cl | 3-Thienyl |
| 3.3 | SO₂CH₃ | Cl | 2-Furyl |
| 3.4 | SO₂CH₃ | Cl | 3-Furyl |
| 3.5 | SO₂CH₃ | Cl | 3-Methyl-isoxazol-5-yl |
| 3.6 | SO₂CH₃ | Cl | 5-Thiazolyl |
| 3.7 | SO₂CH₃ | Cl | 4-Thiazolyl |
| 3.8 | SO₂CH₃ | Cl | 2-Thiazolyl |
| 3.9 | SO₂CH₃ | Cl | 3-Isoxazolyl |
| 3.10 | SO₂CH₃ | Cl | 2-Pyridyl |
| 3.11 | SO₂CH₃ | Cl | 3-Pyridyl |
| 3.12 | SO₂CH₃ | Cl | 4-Pyridyl |
| 3.13 | SO₂CH₃ | Cl | 2-Benzthiazolyl |
| 3.14 | SO₂CH₃ | Cl | 2-Quinolyl |
| 3.15 | SO₂CH₃ | Cl | 4-Methyl-oxazol-2-yl |
| 3.16 | SO₂CH₃ | Cl | 5-Pyrimidinyl |
| 3.17 | SO₂CH₃ | CH₃ | 2-Thienyl |
| 3.18 | SO₂CH₃ | CH₃ | 3-Thienyl |
| 3.19 | SO₂CH₃ | CH₃ | 2-Furyl |
| 3.20 | SO₂CH₃ | CH₃ | 3-Furyl |
| 3.21 | SO₂CH₃ | CH₃ | 3-Methyl-isoxazol-5-yl |
| 3.22 | SO₂CH₃ | CH₃ | 5-Thiazolyl |
| 3.23 | SO₂CH₃ | CH₃ | 4-Thiazolyl |
| 3.24 | SO₂CH₃ | CH₃ | 2-Thiazolyl |
| 3.25 | SO₂CH₃ | CH₃ | 3-Isoxazolyl |
| 3.26 | SO₂CH₃ | CH₃ | 2-Pyridyl |
| 3.27 | SO₂CH₃ | CH₃ | 3-Pyridyl |
| 3.28 | SO₂CH₃ | CH₃ | 4-Pyridyl |
| 3.29 | SO₂CH₃ | CH₃ | 2-Benzthiazolyl |
| 3.30 | SO₂CH₃ | CH₃ | 2-Quinolyl |
| 3.31 | SO₂CH₃ | CH₃ | 4-Methyl-oxazol-2-yl |
| 3.32 | SO₂CH₃ | CH₃ | 5-Pyrimidinyl |

TABLE 4

Compounds of the structure Ig

| No. | R³ | L | M | Z |
|---|---|---|---|---|
| 4.1 | 2-Ethylthiopropyl | SO₂CH₃ | Cl | 2-Thienyl |
| 4.2 | 2-Ethylthiopropyl | SO₂CH₃ | Cl | 3-Thienyl |
| 4.3 | 2-Ethylthiopropyl | SO₂CH₃ | Cl | 2-Furyl |
| 4.4 | 2-Ethylthiopropyl | SO₂CH₃ | Cl | 3-Furyl |
| 4.5 | 2-Ethylthiopropyl | SO₂CH₃ | Cl | 3-Methyl-isoxazol-5-yl |
| 4.6 | 2-Ethylthiopropyl | SO₂CH3. | Cl | 5-Thiazolyl |
| 4.7 | 2-Ethylthiopropyl | SO₂CH₃ | Cl | 4-Thiazolyl |
| 4.8 | 2-Ethylthiopropyl | SO₂CH₃ | Cl | 2-Thiazolyl |
| 4.9 | 2-Ethylthiopropyl | SO₂CH₃ | Cl | 3-Isoxazolyl |
| 4.10 | 2-Ethylthiopropyl | SO₂CH₃ | Cl | 2-Pyridyl |
| 4.11 | 2-Ethylthiopropyl | SO₂CH₃ | Cl | 3-Pyridyl |
| 4.12 | 2-Ethylthiopropyl | SO₂CH₃ | Cl | 4-Pyridyl |
| 4.13 | 2-Ethylthiopropyl | SO₂CH₃ | Cl | 2-Benzthiazolyl |
| 4.14 | 2-Ethylthiopropyl | SO₂CH₃ | Cl | 2-Quinolyl |
| 4.15 | 2-Ethylthiopropyl | SO₂CH₃ | Cl | 4-Methyl-oxazol-2-yl |
| 4.16 | 2-Ethylthiopropyl | SO₂CH₃ | Cl | 5-Pyrimidinyl |
| 4.17 | Tetrahydropyran-3-yl | SO₂CH₃ | Cl | 2-Thienyl |
| 4.18 | Tetrahydropyran-3-yl | SO₂CH₃ | Cl | 3-Thienyl |
| 4.19 | Tetrahydropyran-3-yl | SO₂CH₃ | Cl | 2-Furyl |
| 4.20 | Tetrahydropyran-3-yl | SO₂CH₃ | Cl | 3-Furyl |
| 4.21 | Tetrahydropyran-3-yl | SO₂CH₃ | Cl | 3-Methyl-isoxazol-5-yl |
| 4.22 | Tetrahydropyran-3-yl | SO₂CH₃ | Cl | 5-Thiazolyl |
| 4.23 | Tetrahydropyran-3-yl | SO₂CH₃ | Cl | 4-Thiazolyl |
| 4.24 | Tetrahydropyran-3-yl | SO₂CH₃ | Cl | 2-Thiazolyl |
| 4.25 | Tetrahydropyran-3-yl | SO₂CH₃ | Cl | 3-Isoxazolyl |
| 4.26 | Tetrahydropyran-3-yl | SO₂CH₃ | Cl | 2-Pyridyl |
| 4.27 | Tetrahydropyran-3-yl | SO₂CH₃ | Cl | 3-Pyridyl |
| 4.28 | Tetrahydropyran-3-yl | SO₂CH₃ | Cl | 4-Pyridyl |

TABLE 4-continued

Compounds of the structure Ig

| No. | R³ | L | M | Z |
|---|---|---|---|---|
| 4.29 | Tetrahydropyran-3-yl | SO₂CH₃ | Cl | 2-Benzthiazolyl |
| 4.30 | Tetrahydropyran-3-yl | SO₂CH₃ | Cl | 2-Quinolyl |
| 4.31 | Tetrahydropyran-3-yl | SO₂CH₃ | Cl | 4-Methyl-oxazol-2-yl |
| 4.32 | Tetrahydropyran-3-yl | SO₂CH₃ | Cl | 5-Pyrimidinyl |
| 4.33 | Tetrahydropyran-4-yl | SO₂CH₃ | Cl | 2-Thienyl |
| 4.34 | Tetrahydropyran-4-yl | SO₂CH₃ | Cl | 3-Thienyl |
| 4.35 | Tetrahydropyran-4-yl | SO₂CH₃ | Cl | 2-Furyl |
| 4.36 | Tetrahydropyran-4-yl | SO₂CH₃ | Cl | 3-Furyl |
| 4.37 | Tetrahydropyran-4-yl | SO₂CH₃ | Cl | 3-Methyl-isoxazol-5-yl |
| 4.38 | Tetrahydropyran-4-yl | SO₂CH₃ | Cl | 5-Thiazolyl |
| 4.39 | Tetrahydropyran-4-yl | SO₂CH₃ | Cl | 4-Thiazolyl |
| 4.40 | Tetrahydropyran-4-yl | SO₂CH₃ | Cl | 2-Thiazolyl |
| 4.41 | Tetrahydropyran-4-yl | SO₂CH₃ | Cl | 3-I[00a3]oxazolyl |
| 4.42 | Tetrahydropyran-4-yl | SO₂CH₃ | Cl | 2-Pyridyl |
| 4.43 | Tetrahydropyran-4-yl | SO₂CH₃ | Cl | 3-Pyridyl |
| 4.44 | Tetrahydropyran-4-yl | SO₂CH₃ | Cl | 4-Pyridyl |
| 4.45 | Tetrahydropyran-4-yl | SO₂CH₃ | Cl | 2-Benzthiazolyl |
| 4.46 | Tetrahydropyran-4-yl | SO₂CH₃ | Cl | 2-Quinolyl |
| 4.47 | Tetrahydropyran-4-yl | SO₂CH₃ | Cl | 4-Methyl-oxazol-2-yl |
| 4.48 | Tetrahydropyran-4-yl | SO₂CH₃ | Cl | 5-Pyrimidinyl |
| 4.49 | Tetrahydro-thiopyran-3-yl | SO₂CH₃ | Cl | 2-Thienyl |
| 4.50 | Tetrahydro-thiopyran-3-yl | SO₂CH₃ | Cl | 3-Thienyl |
| 4.51 | Tetrahydro-thiopyran-3-yl | SO₂CH₃ | Cl | 2-Furyl |
| 4.52 | Tetrahydro-thiopyranyl-3-yl | SO₂CH₃ | Cl | 3-Furyl |
| 4.53 | Tetrahydro-thiopyranyl 3-yl | SO₂CH₃ | Cl | 3-Methyl-isoxazol-5-yl |
| 4.54 | Tetrahydro-thiopyran-3-yl | SO₂CH₃ | Cl | 5-Thiazolyl |
| 4.55 | Tetrahydro-thiopyran-3-yl | SO₂CH₃ | Cl | 4-Thiazolyl |
| 4.56 | Tetrahydro-thiopyran-3-yl | SO₂CH₃ | Cl | 2-Thiazolyl |
| 4.57 | Tetrahydro-thiopyran-3-yl | SO₂CH₃ | Cl | 3-Isoxazolyl |
| 4.58 | Tetrahydro-thiopyran-3-yl | SO₂CH₃ | Cl | 2-Pyridyl |
| 4.59 | Tetrahydro-thiopyran-3-yl | SO₂CH₃ | Cl | 3-Pyridyl |
| 4.60 | Tetrahydro-thiopyran-3-yl | SO₂CH₃ | Cl | 4-Pyridyl |
| 4.61 | Tetrahydro-thiopyran-3-yl | SO₂CH₃ | Cl | 2-Benzthiazolyl |
| 4.62 | Tetrahydro-thiopyran-3-yl | SO₂CH₃ | Cl | 2-Quinolyl |
| 4.63 | Tetrahydro-thiopyran-3-yl | SO₂CH₃ | Cl | 4-Methyl-oxazol-2-yl |
| 4.64 | Tetrahydro-thiopyran-3-yl | SO₂CH₃ | Cl | 5-Pyrimidinyl |
| 4.65 | 1-Methylthio-cyclopropyl | SO₂CH₃ | Cl | 2-Thienyl |
| 4.66 | 1-Methylthio-cyclopropyl | SO₂CH₃ | Cl | 3-Thienyl |
| 4.67 | 1-Methylthio-cyclopropyl | SO₂CH₃ | Cl | 2-Furyl |
| 4.68 | 1-Methylthio-cyclopropyl | SO₂CH₃ | Cl | 3-Furyl |
| 4.69 | 1-Methylthio-cyclopropyl | SO₂CH₃ | Cl | 3-Methyl-isoxazol-5-yl |
| 4.70 | 1-Methylthio-cyclopropyl | SO₂CH₃ | Cl | 5-Thiazolyl |
| 4.71 | 1-Methylthio-cyclopropyl | SO₂CH₃ | Cl | 4-Thiazolyl |
| 4.72 | 1-Methylthio-cyclopropyl | SO₂CH₃ | Cl | 2-Thiazolyl |
| 4.73 | 1-Methylthio-cyclopropyl | SO₂CH₃ | Cl | 3-Isoxazolyl |
| 4.74 | 1-Methylthio-cyclopropyl | SO₂CH₃ | Cl | 2-Pyridyl |
| 4.75 | 1-Methylthio-cyclopropyl | SO₂CH₃ | CJ | 3-Pyridyl |
| 4.76 | 1-Methylthio-cyclopropyl | SO₂CH₃ | Cl | 4-Pyridyl |
| 4.77 | 1-Methylthio-cyclopropyl | SO₂CH₃ | Cl | 2-Benzthiazolyl |
| 4.78 | 1-Methylthio-cyclopropyl | SO₂CH₃ | Cl | 2-Quinolyl |
| 4.79 | 1-Methylthio-cyclopropyl | SO₂CH₃ | Cl | 4-Methyl-oxazol-2-yl |
| 4.80 | 1-Methylthio-cyclopropyl | SO₂CH₃ | Cl | 5-Pyrimidinyl |
| 4.81 | (Dimethoxy)methyl | SO₂CH₃ | Cl | 2-Thienyl |
| 4.82 | (Dimethoxy)methyl | SO₂CH₃ | Cl | 3-Thienyl |
| 4.83 | (Dimethoxy)methyl | SO₂CH₃ | Cl | 2-Furyl |
| 4.84 | (Dimethoxy)methyl | SO₂CH₃ | Cl | 3-Furyl |
| 4.85 | (Dimethoxy)methyl | SO₂CH₃ | Cl | 3-Methyl-isoxazol-5-yl |
| 4.86 | (Dimethoxy)methyl | SO₂CH₃ | Cl | 5-Thiazolyl |
| 4.87 | (Dimethoxy)methyl | SO₂CH₃ | Cl | 4-Thiazolyl |
| 4.88 | (Dimethoxy)methyl | SO₂CH₃ | Cl | 2-Thiazolyl |
| 4.89 | (Dimethoxy)methyl | SO₂CH₃ | Cl | 3-Isoxazolyl |
| 4.90 | (Dimethoxy)methyl | SO₂CH₃ | Cl | 2-Pyridyl |
| 4.91 | (Dimethoxy)methyl | SO₂CH₃ | Cl | 3-Pyridyl |
| 4.92 | (Dimethoxy)methyl | SO₂CH₃ | Cl | 4-Pyridyl |
| 4.93 | (Dimethoxy)methyl | SO₂CH₃ | Cl | 2-Benzthiazolyl |
| 4.94 | (Dimethoxy)methyl | SO₂CH₃ | Cl | 2-Quinolyl |
| 4.95 | (Dimethoxy)methyl | SO₂CH₃ | Cl | 4-Methyl-oxazol-2-yl |
| 4.96 | (Dimethoxy)methyl | SO₂CH₃ | Cl | 5-Pyrimidinyl |

TABLE 5

Compounds of the structure Ih

| No. | R³ | R⁴ | L | M | Z |
|---|---|---|---|---|---|
| 5.1 | H | H | SO₂CH₃ | Cl | 3-Thienyl |
| 5.2 | H | H | SO₂CH₃ | Cl | 3-Furyl |
| 5.3 | H | H | SO₂CH₃ | Cl | 3-Methyl-isoxazol-5-yl |
| 5.4 | H | H | SO₂CH₃ | Cl | 2-Thiazolyl |
| 5.5 | H | H | SO₂CH₃ | Cl | 2-Pyridyl |
| 5.6 | H | H | SO₂CH₃ | Cl | 3-Pyridyl |
| 5.7 | H | H | SO₂CH₃ | Cl | 4-Pyridyl |
| 5.8 | H | H | SO₂CH₃ | Cl | 2-Benzthiazolyl |
| 5.9 | H | H | SO₂CH₃ | Cl | 5-Pyrimidinyl |
| 5.10 | CH₃ | H | SO₂CH₃ | Cl | 3-Thienyl |
| 5.11 | CH₃ | H | SO₂CH₃ | Cl | 3-Furyl |
| 5.12 | CH₃ | H | SO₂CH₃ | Cl | 3-Methyl-isoxazol-5-yl |
| 5.13 | CH₃ | H | SO₂CH₃ | Cl | 2-Thiazolyl |
| 5.14 | CH₃ | H | SO₂CH₃ | Cl | 2-Pyridyl |
| 5.15 | CH₃ | H | SO₂CH₃ | Cl | 3-Pyridyl |
| 5.16 | CH₃ | H | SO₂CH₃ | Cl | 4-Pyridyl |
| 5.17 | CH₃ | H | SO₂CH₃ | Cl | 2-Benzthiazolyl |
| 5.18 | CH₃ | H | SO₂CH₃ | Cl | 5-Pyrimidinyl |
| 5.19 | CH₃ | CH₃ | SO₂CH₃ | Cl | 3-Thienyl |
| 5.20 | CH₃ | CH₃ | SO₂CH₃ | Cl | 3-Furyl |
| 5.21 | CH₃ | CH₃ | SO₂CH₃ | Cl | 3-Methyl-isoxazol-5-yl |
| 5.22 | CH₃ | CH₃ | SO₂CH₃ | Cl | 2-Thiazolyl |
| 5.23 | CH₃ | CH₃ | SO₂CH₃ | Cl | 2-Pyridyl |
| 5.24 | CH₃ | CH₃ | SO₂CH₃ | Cl | 3-Pyridyl |
| 5.25 | CH₃ | CH₃ | SO₂CH₃ | Cl | 4-Pyridyl |
| 5.26 | CH₃ | CH₃ | SO₂CH₃ | Cl | 2-Benzthiazolyl |
| 5.27 | CH₃ | CH₃ | SO₂CH₃ | Cl | 5-Pyrimidinyl |

The compounds I and their agriculturally useful salts are suitable as herbicides, both in the form of isomer mixtures and as pure isomers. The herbicides containing I control plant growth on uncultivated surfaces vary effectively, particularly at high application rates. They act against weeds and grass weeds in crops such as wheat, rice, corn, soybean and cotton without significantly damaging the crop. This effect occurs in particular at low application rates.

Taking into account the versatility of the application metods, the compounds I and the agents containing them can also be used in a further number of crops for eliminating undesirable plants. For example, the following crops are suitable:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus ssp., *Manihot esculenta, Medicago sativa,* Musa ssp., *Nicotiana tabacum* (*N. rustica*), *Olea europaea, Oryza sativa, Phaseolus lunatus, Phaseolus vulgaris, Picea abies,* Pinus ssp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vivia faba, Vitis vinifera, Zea mays.*

The compounds I can also be used in crops which are tolerant to the action of herbicides as a result of breeding, including genetic engineering methods.

The herbicides or the active ingredients can be applied by the preemergence or postemergence methods. If the active ingredients are less well tolerated by certain crops, it is possible to use application methods in which the herbicides are sprayed with the aid of the sprayers so that the leaves of the sensitive crops are as far as possible not affected while the active ingredients reach the leaves of undesirable plants growing underneath or the uncovered soil surface (post-directed lay-by).

The compounds I and the herbicides containing them can be applied, for example, in the form of directly sprayable aqueous solutions, powders, suspensions, including concentrated aqueus, oily or other suspensions or dispersions, emulsions, oil dispersions, pastes, dusting agents, broadcasting agents or granules, by spraying, nebulizing, dusting, broadcasting or pouring. The application forms depend on the intended uses; they should in any case ensure very fine distribution of the novel active ingredients.

Suitable inert additives are mineral oil fractions having a medium to high boiling point, such as kerosene or diesel oil, and coal tar oils and oils of vegetable or animal origin, aliphatic, cyclic and aromatic hydrocarbons, for example paraffin, tetrahydronaphthalene, alkylated naphthalenes or derivatives thereof, alkylated benzenes or derivatives thereof, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by adding water. For the preparation of emulsions, pastes or oil dispersions, the substances, as such or dissolved in an oil or solvent, can be homogenized in water by means of wetting agents, adherents, dispersants or emulsifiers. However, it is also possible to prepare concentrates which consist of active ingredient, wetting agents, adherents, dispersants or emulsifiers and possibly solvents or oil and which are suitable for dilution with water.

Suitable surfactants (adjuvants) are the alkali metal, alkaline earth metal and ammonium salts or aromatic sulfonic acids, for example ligninsulfonic, phenolsulfonic, naphthalenesulfonic and dibutylnaphthalenesulfonic acid, and of fatty acids, alkylsulfonates and alkylarylsulfonats, alkylsulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alchols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, ligninsulfite waste liquors or methylcellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders or other solid carriers.

The concentrations of the active ingredients I in the ready-to-use compositions can be varied within wide ranges. The formulations contain in general from 0.001 to 98, preferably from 0.01 to 95, % by weight of active ingredient. The active ingredients are used in a purity of from 90 to 100%, preferably from 95 to 100% (according to the NMR spectrum).

The novel compounds I can be formulated, for example, as follows:

I 20 parts by weight of compound No. 1.1232 are dissolved in a mixture which consists of 80 parts by weight of alkylated benzene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

II 20 parts by weight of compound No. 1.12332 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III 20 parts by weight of active ingredient No. 1.1232 are dissolved in the mixture which consists of 25 parts by weight of cyclohexanone, 65 parts by weight of a mineral oil fraction boiling within the range from 210 to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV 20 parts by weight of active ingredient No. 1.1232 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

V 3 parts by weight of active ingredient No. 1.1232 are mixed with 97 parts by weight of finely divided kaolin. A dusting agent which contains 3% by weight of the active ingredient is obtained in this manner.

VI 20 parts by weight of active ingredient No. 1.1232 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

VII 1 part by weight of compound No. 1.1232 is dissolved in a mixture which consists of 70 parts by weight of cyclohexanone, 20 parts by weight of ethoxylated isooctylphenol and 10 parts by weight of ethoxylated castor oil. A stable emulsion concentrate is obtained.

VIII 1 part by weight of compound No. 1.1232 is dissolved in a mixture which consists of 80 parts by weight of cyclohexanone and 20 parts by weight of Emulphor EL. A stable emulsion concentrate is obtained.

In order to broaden the action spectrum and to achieve synergistic effects, the benzoyl derivatives I can be mixed with a large number of members of other groups of herbicidal or growth-regulating active ingredients and applied together with them. For example, suitable components of the mixture are diazines, 4H- 3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives which carry, for example, a carboxyl or carbimino group in the 2 position, quinolinecarboxylic acid derivatives, imidazolinones, sulfonamides, sulfonylureas, aryloxy- and hetaryloxyphenoxypropionic acids and their salts, esters and amides and others.

It may also be useful to apply the compound I, alone or in combination with other herbicides, also as a mixture with further crop protection agents, for example with pesticides or agents for controlling phytophathogenic fungi or bacteria. The miscibility with mineral salt solutions which are used for eliminating nutrient and trace element deficiencies is also of interest. Nonphytotoxic oils and oil concentrates may also be added.

The application rates of active ingredient are from 0.001 to 3.0, preferably from 0.01 to 1.0, kg/ha of active ingredient (a.i.), depending on the aim of the control, the season, the target plants and stage of growth.

USE EXAMPLES

The herbicidal action of the benzoyl derivatives of the formula I were demonstrated by greenhouse experiments:

The culture vessels used were plastic flower pots containing loamy sand with about 3.0% of humus as substrate. The seeds of the test plants were sown separately according to species.

In the preemergence treatment, the active ingredients suspended or emulsified in water were applied directly after sowing, by means of finely distributing nozzles. The vessels were lightly sprinkle-irrigated in order to promote germination and growth and were then covered with transparent plastic covers until the plants had begun to grow. This covering ensures uniform germination of the test plants, unless this has been impaired by the active ingredients.

For the postemergence treatment, the test plants are grown to a height of growth of from 3 to 15 cm, depending on the form of growth, before being treated with the active ingredients suspended or emulsified in water. For this purpose, the test plants are either directly sown and grown in the same vessels or are first grown separately as seedlings and transplanted into the test vessels a few days before the treatment. The application rate for the postemergence treatment is 0.125 or 0.0625 kg/ha a.i.

The plants were kept at 10–25° C. or 20–35° C., according to species. The test period extended over from 2 to 4 weeks. During this time, the plants were tended and their reaction to the individual treatments was evaluated.

The evaluation was based on a scale from 0 to 100. 100 means no emergence of the plants or complete destruction of at least the above-ground parts and 0 means no damage or normal course of growth.

The plants used in the greenhouse experiments consisted of the following species:

| Botanical name | Common name |
|---|---|
| *Abutiolon theophrasti* | velvet leaf |
| *Amaranthus retroflexus* | redroot pigweed |
| *Echinochloa crus-galli* | barnyardgrass |
| *Solanum nigrum* | black nightshade |
| *Zea mays* | Indian corn |

Selective herbicidal activity during postemergence use in the greenhouse

TABLE 6

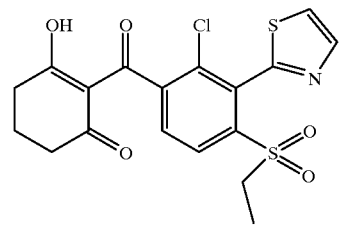

Example No. 1.1232

| Application rate (kg/ha a.i.) | 0.125 | 0.0625 |
|---|---|---|
| Test plants | Damage in % | |
| ZEAMX | 10 | 0 |
| ABUTH | 100 | 95 |
| AMARE | 100 | 100 |
| ECHCG | 98 | 95 |
| SOLNI | 100 | 100 |

TABLE 7

Herbicidal activity during postemergence use in the greenhouse

| Application rate (kg/ha a.i.) | 0.125 | 0.0625 |
|---|---|---|
| Test plants | Damage in % | |
| ZEAMX | 10 | 0 |
| ECHCG | 95 | 95 |
| CHEAL | 95 | 95 |
| SINAL | 90 | 90 |
| SOLNI | 100 | 100 |

TABLE 8

Herbicidal activity during postemergence use in the greenhouse

| Application rate (kg/ha a.i.) | 0.125 | 0.0625 |
|---|---|---|
| Test plants | Damage in % | |
| ZEAMX | 10 | 0 |
| ECHCG | 95 | 95 |
| CHEAL | 95 | 95 |

PREPARATION EXAMPLES

A) Preparation of the Starting Materials

1. Methyl 2-chloro-3-formyl-4-methylsulfonylbenzoate a. A solution of 157 g (2 mol) of acetyl chloride in 420 mol of 1,2-dichloroethane was added dropwise at 15–20° C. to a suspension of 286 g (2.14 mol) of aluminum trichloride in 420 ml of 1,2-dichloroethane. A solution of 346 g (2 mol) of 2-chloro-6-methylthiotoluene in 1 l of 1,2-dichloroethane was then added dropwise. Stirring was carried out for 12 hours, after which the reaction mixture was poured into a mixture of 3 l of ice and 1 l of concentrated HCl. The mixture was extracted with methylene chloride and the organic phase was washed with water, dried with sodium sulfate and evaporated down. The residue was distilled under reduced pressure.

256 g (60% of theory) of 2-chloro-3-methyl-4-methylthioacetophenone of melting point 46° C. were obtained.

b. 163 g (0.76 mol) of 2-chloro-3-methyl-4-methylthioacetophenone were dissolved in 1.5 l of glacial acetic acid, 18.6 g of sodium tungstate were added and 173.3 g of 30% strength hydrogen peroxide solution were added dropwise while cooling. Stirring was continued for 2 days and was followed by dilution with water. The precipitated solid was filtered off with suction, washed with water and dried.

164 g (88% of theory) of 2-chloro-3-methyl-4-methylsulfonylacetophenone of melting point 110–111° C. were obtained.

c. 82 g (0.33 mol) of 2-chloro-3-methyl-4-methylsulfonylacetophenone were dissolved in 700 ml of dioxane, and 1 l of a 12.5% strength sodium hypochlorite solution was added at room temperature. Stirring was then carried out for 1 hour at 80° C. Cooling the mixture resulted in two phases, the lower of which was diluted with water and slightly acidified. The precipitated solid was washed with water and dried.

60 g (73% of theory) of 2-chloro-3-methyl-4-methylsulfonylbenzoic acid of melting point 230–231° C. were obtained.

d. 100 g (0.4 mol) of 2-chloro-3-methyl-4-methylsulfonylbenzoic acid were dissolved in 1 l of methanol and gassed with HCl for 5 hours at the reflux temperature. The mixture was then evaporated down.

88.5 g (84% of theory) of methyl 2-chloro-3-methyl-4-methylsulfonylbenzoate of melting point 107–108° C. were obtained.

e. 82 g (0.31 mol) of methyl 2-chloro-3-methyl-4-methylsulfonylbenzoate were dissolved in 2 l of tetrachloromethane, and 56 g (0.31 mol) of N-bromosuccinimide were added a little at a time with exposure to light. The reaction mixture was filtered, the filtrate was evaporated down and the residue was taken up in 200 ml of methyl tert-butyl ether. Petroleum ether was added to the solution, and the precipitated solid was filtered off with suction and dried.

74.5 g (70% of theory) of methyl 3-bromomethyl-2-chloro-4-methylsulfonylbenzoate of melting point 74–75° C. were obtained.

f. 42.1 g (0.36 mol) of N-methylmorpholine N-oxide were added to a solution of 41 g (0.12 mol) of methyl 3-bromomethyl-2-chloro-4-methylsulfonylbenzoate in 250 ml of acetonitrile. The match was stirred for 12 hours at room temperature and then evaporated down, and the residue was taken up in ethyl acetate. The solution was extracted with water, dried with sodium sulfate and evaporated down.

31.2 g (94% of theory) of methyl 2-chloro-3-formyl-4-methylsulfonylbenzoate of melting point 98–105° C. were obtained.

2. Methyl 2-chloro-4-methylsulfonyl-3-(trifluoromethylsulfonyl)oxybenzoate a. 101 g (0.41 mol) of 2-chloro-3-hydroxy-4-methylsulfonylbenzoic acid were dissolved in 1.3 l of methanol and gassed with HCl for 4 hours under reflux. The solution was evaporated down, the residue was taken up in dichloromethane and the resulting solution was extracted with $K_2CO_3$ solution. The aqueous phase was brought to a pH 7 with dilute hyrdrochloric acid and washed with dichloromethane. It was then acidified to pH 1 and the product was extracted with dichloromethane.

76.2 g (71% of theory) of methyl 2-chloro-3-hydroxy-4-methylsulfonylbenzoate were obtained.

b. 89 g (0.32 mol) of trifluoromethanesulfonic anhydride were added at –20° C. to a solution of 76 g (0.29 mol) of methyl 2-chloro-3-hydroxy-4-methylsulfonylbenzoate and 68 g of pyridine in 700 ml of dichloromethane. The solution was stirred for 12 hours at room temperature, diluted with dichloromethane and extracted with water. The organic phase was dried over magnesium sulfate and evaporated down.

94 g (82% of theory) of methyl 2-chloro-4-methylsulfonyl-3-(trifluoromethylsulfonyl)oxybenzoate of melting point 69° C. were obtained.

B) Preparation of the Intermediates

1. Methyl 3-(3-isopropylisoxazol-5-yl)-4-methylsulfonylbenzoate a. 10 g (102 mmol) of trimethylsilylacetylene and 180 mg of copper(I) iodide were added to 30 g (102 mmol) of methyl 3-bromo-4-methylsulfonylbenzoate, 90 mg of palladium dichloride and 240 mg of triphenylphosphine in 200 ml of diethylamine and 60 ml of dimethylformamide, and the mixture was stirred for 4.5 hours at 40° C. Stirring was then continued for a further 12 hours at room temperature. The reaction mixture was filtered, the filtrate was evaporated down and the residue was chromatographed over silica gel using toluene as the mobile phase.

17.3 g (55% of theory) of methyl 4-methylsulfonyl-3-(trimethylsilyl)ethynylbenzoate were obtained as an oil.

b. 25 g of methyl 4-methylsulfonyl-3-(trimethylsilyl)ethynylbenzoate were stirred with 100 ml of methanol and 0.9 g of potassium carbonate for 18 hours at room temperature. The solid was then filtered off with suction and the filtrate was evaporated down and extracted with ethyl acetate/water. The organic phase was dried over sodium sulfate and evaporated down.

15 g (79% of theory) of methyl 4-methylsulfonyl-3-ethynylbenzoate of melting point 95–98° C. were obtained.

c. 13.5 g (57 mmol) of methyl 4-methylsulfonyl-3-ethynylbenzoate were dissolved in 50 ml of dichloromethane, 5.2 g (60 mmol) of isobutyraldehyde oxime were added and 41 g of a 12.5% strength sodium hypochlorite solution were added dropwise. Stirring was then carried out for 24 hours at room temperature. The reaction batch was then extracted with dichloromethane/water, the organic phase was evaporated down and the residue was chromatographed over silica gel using toluene/ethyl acetate as the mobile phase.

8.8 g (48% of theory) of methyl 3-(3-isopropylisoxazol-5-yl)-4-methylsulfonylbenzoate of melting point 102–104° C. were obtained.

2. Methyl 2-chloro-3-(isoxazol-3-yl)-4-methylsulfonylbenzoate a. 15 g (54 mmol) of methyl 2-chloro-3-formyl-4-methylsulfonylbenzoate (Example A.1.) and 4.2 g (60 mmol) of hydroxylamine hydrochloride were stirred with 300 ml of methanol, and a solution of 3.18 g (30 mmol) of sodium carbonate in 80 ml of water was added dropwise. The reaction mixture was stirred overnight at room temperature, after which the methanol was distilled off and the batch was extracted with ether/water. The ether phase was dried with sodium sulfate and evaporated down.

14.4 g (91% of theory) of methyl 2-chloro-3-hydroxyiminomethyl-4-methylsulfonylbenzoate of melting point 126–128° C. were obtained.

b. 5.3 g (18 mmol) of methyl 2-chloro-3-hydroxyiminomethyl-4-methylsulfonylbenzoate were dissolved in 50 ml of dichloromethane, and acetylene was passed in at 0–5° C. for 30 minutes. Thereafter, a pinch of sodium acetate was added and 15 ml of a 10% strength sodium hypochlorite solution was added dropwise at 10° C. with further introduction of acetylene. After the end of the addition, acetylene was passed in at 10° C. for a further 15 minutes and stirring was then carried out for 12 hours. Thereafter, the phases were separated and the organic phase was washed with water, dried with sodium sulfate and evaporated down.

4.8 g (84% of theory) of methyl 2-chloro-3-(isoxazol-3-yl)-4-methylsulfonylbenzoate of melting point 145–147° C. were obtained.

3. Methyl 2-chloro-3-(thiazol-2-yl)-4-methylsulfonylbenzoate 33 g (88 mmol) of 2-(tributylstannyl)-thiazole, 17.5 g (44 mmol) of methyl 2-chloro-4-methylsulfonyl-3-(trifluoromethylsulfonyl)oxy-benzoate (Example A.2.), 5.8 g of lithium chloride, 1 g of tetrakis(triphenylphosphine) palladium (0), a pinch of 2,6-di-tert-butyl-4-methylphenol and 200 ml of 1,4-dioxane were stirred in an autoclave for 3 hours at 140° C. under autogenous pressure. After cooling, the reaction mixture was filtered over a silica gel layer, washed with methyl tert-butyl ether and evaporated down. The residue was chromatographed over silica gel using toluene/ethyl acetate as the mobile phase.

9.1 g (62.6% of theory) of methyl 2-chloro-3-(thiazol-2-yl)-4-methylsulfonylbenzoate of melting point 135–138° C. were obtained.

4. Methyl 2-chloro-3-(oxazol-5-yl)-4-methylsulfonylbenzoate 25 g (0.09 mol) of methyl 2-chloro-3-formyl-4-methylsulfonylbenzoate (Example A.1.), 17.6 g (0.09 mol) of tosylmethylene isocyanide and 6.2 g (0.045 mol) of finely powdered potassium carbonate were stirred under reflux for 5 hours with 450 ml of methanol. The solvent was then stripped off, the residue was taken up in ethyl acetate and the solution was extracted with water. The ethyl acetate phase was dried with sodium sulfate and evaporated down.

24.7 g (87% of theory) of methyl 2-chloro-3-(oxazol-5-yl)-4-methylsulfonylbenzoate were obtained.

$^1$H-NMR (CDCl$_3$)

δ: 8.24 (d, 1H), 8.15 (s, 1H), 8.01 (d, 1H), 7.40 (s, 1H), 4.0 (s, 3H), 2.96 (s, 3H)

The intermediates shown in the Table below were obtained in a similar manner:

TABLE 9

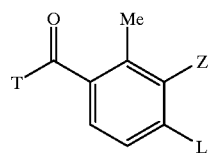

| No. | T | L | M | Z | Physical data m.p. [° C.] |
|---|---|---|---|---|---|
| 9.1 | Methoxy | —SO₂Me | Cl | 3-Furyl | ¹H-NMR (CDCl₃) δ: 8.24 (d, 1H), 7.82 (d, 1H), 7.64 (m, 2H), 6.55 (s, 1H) 3.99 (s, 3H), 2.80 (s, 3H) |
| 9.2 | Methoxy | —SO₂Me | H | 2-Thiazolyl | 95–98 |
| 9.3 | Ethoxy | —SO₂Et | Cl | 2-Thiazolyl | ¹H-NMR (CDCl₃) δ: 8.18 (d, 1H), 7.97 (m, 2H), 7.71 (d, 1H), 4.47 (q, 2H) 3.36 (q, 2H), 1.42 (t, 3H), 1.24 (t, 3H) |
| 9.4 | OH | —SO₂CH₃ | Cl | 2-Thiazolyl | 288–290 |
| 9.5 | OH | —SO₂CH₃ | Cl | 2-Thienyl | 177–180 |
| 9.6 | OH | —SO₂CH₃ | CH₃ | 2-Thienyl | 175–178 |
| 9.7 | OH | —SO₂CH₃ | CH₃ | 2-Furyl | 167–171 |
| 9.8 | Methoxy | —SO₂CH₃ | CH₃ | 2-Thienyl | 91–95 |
| 9.9 | OH | —SO₂CH₃ | H | 2-Furyl | 219–223 |
| 9.10 | Methoxy | —SO₂CH₃ | CH₃ | 2-Furyl | 103–106 |
| 9.11 | OH | —SO₂CH₃ | H | 2-Thienyl | 222–224 |
| 9.12 | Methoxy | —SO₂CH₃ | Cl | 3-Isoxazoyl | ¹H-NMR (CDCl₃) δ: 8.62 (1H); 8.18 (1H); 6.58 (1H); 3.98 (3H; 3.22 (3H) |
| 9.13 | Methoxy | —SO₂CH₃ | Cl | 5-Phenyl-oxazol-2-yl | 115–118 |
| 9.14 | Methoxy | —SO₂CH₃ | Cl | 5-Oxazolyl | ¹H-NMR (CDCl₃) δ: 8.76 (1H); 8.22 (1H); 8.10 (1H); 7.63 (1H); 4.04 (3H); 3.08 (3H) |
| 9.15 | Methoxy | —SO₂CH₃ | Cl | 5-Cycloprop-yl-isoxa-zolyl | ¹H-NMR (CDCl₃) δ: 8.20 (1H); 7.95 (1H); 6.12 (1H); 3.98 (3H); 3.22 (3H); 2.15 (1H); 1.03–1.09 (4H) |
| 9.16 | Methoxy | —SO₂CH₃ | Cl | 4,5-Dihy-droisoxa-zol-3-yl | ¹H-NMR (CDCl₃) δ: 8.12 (1H); 7.98 (1H); 4.60 (1H); 3.98 (3H); 3.42 (2H); 3.25 (3H) |
| 9.17 | Methoxy | —SO₂CH₃ | Cl | 5-Methyl-1,2,4-oxadia-zol-3-yl | 102–105 |
| 9.18 | Methoxy | —SO₂CH₃ | Cl | 4,5-Dihydro-oxazol-2-yl | ¹H-NMR (CDCl₃) δ: 8.08 (1H); 7.98 (1H); 4.57 (2H); 4.12 (2H); 3.98 (3H); |
| 9.19 | OH | —SO₂CH₃ | Cl | 3-Furyl | ¹H-NMR (CDCl₃) δ: 8.29 (1H); 8.02 (1H); 7.67 (2H); 6.59 (1H); 2.83 (3H); |
| 9.20 | Methoxy | —SO₂CH₃ | Cl | 3-Thienyl | ¹H-NMR (CDCl₃) δ: 8.23 (1H); 7.84 (1H); 7.49 (2H); 7.13 (1H); 3.98 (3H); 2.62 (3H) |
| 9.21 | OH | —SO₂CH₃ | H | 3-Furyl | 200–202 |
| 9.22 | OH | —SO₂CH₃ | Cl | 5-Methyl-4-phenyl-thiazol-2-yl | 200–204 |

C) Preparation of the end products 1. 2-[3-(3-Isopropylisoxazol-5-yl)-4-methylsulfonylbenzoyl]cylohexane-1,3-dione (Example No. 1.1232)

a. 8 g (25 mmol) of methyl 3-(3-isopropylisoxazol-5-yl)-4-methylsulfonylbenzoate (Example B.1.) were dissolved in 50 ml of methanol, and 1.5 g (37 mmol) of NaOH were added. The solution was stirred for 12 hours at room temperature. Thereafter, the reaction mixture was evaporated down and the residue was taken up in water and the solution was acidified with hydrochloric acid. After prolonged stirring, pale yellow crystals formed. The solid was filtered off with suction and dried.

6.6 g (86% of theory) of 3-(3-isopropylisoxazol-5-yl)-4-methylsulfonylbenzoic acid of melting point 176–178° C. were obtained.

b. 6 g (19 mmol) of 3-(3-isopropylisoxazol-5-yl)-4-methylsulfonylbenzoic acid were dissolved in 60 ml or toluene, one drop of dimethylformamide was added and 3.2 g (27 mmol) of thionyl chloride were introduced. After refluxing for 4 hours, the reaction mixture was evaporated down.

6.3 g (99% of theory) of 3-(3-isopropylisoxazol-5-yl)-4-methylsulfonylbenzoyl chloride of melting point 102–105° C. were obtained.

c. 0.56 g (5.5 mmol) of triethylamine was added to a suspension of 0.5 g (4.6 mmol) of cyclohexane-1,3-dione in 30 ml of dichloromethane, and a solution of 1.5 g (4.6 mmol) of 3-(3-isopropylisoxazol-5-yl)-4-methylsulfonylbenzoyl chloride in 20 ml of dichloromethane was then added dropwise at 25° C. Stirring was then carried out for 12 hours at 40° C. After cooling, the mixture was diluted with water and the dichloromethane phase was separated off, dried over magnesium sulfate and evaporated down. The remaining residue was dissolved in 30 ml of acetonitrile, 2.8 g of triethylamine and then 0.15 g of acetonecyanohydrin were added and stirring was carried out for 12 hours at room temperature. Thereafter, the reaction batch was evaporated down, and the residue was taken up in ethyl acetate and the solution was extracted with dilute hydrochloric acid. After being washed twice with water, the organic phase was extracted with 5% strength potassium carbonate solution. The aqueous phase was brought to pH 6 and reextracted with ethyl acetate. Drying and evaporating down gave 0.51 g (28% of theory) of 2-[3-(3-isopropylisoxazol-5-yl)-4-methylsulfonylbenzoyl]cylohexane-1,3-dione of melting point 95–98° C.

The compounds shown in the Tables below were obtained in a similar manner:

TABLE 10

Id

| No. | $R^3$ | $R^4$ | $R^5$ | L | M | Z | Mp. [° C.] |
|---|---|---|---|---|---|---|---|
| 10.1 | H | H | H | —SO$_2$Me | H | 3-Isopropylisoxazol-5yl | 95–98 |
| 10.2 | Methyl | Methyl | H | —SO$_2$Et | Cl | 2-Thiazolyl | 103–105 |
| 10.3 | H | H | H | —SO$_2$Et | Cl | 2-Thiazolyl | 112–115 |
| 10.4 | H | H | H | —SO$_2$Me | Cl | 2-Thiazolyl | 177 |
| 10.5 | H | H | H | —SO$_2$Me | Cl | 3-Isoxazolyl | 86–98 |
| 10.11 | Methyl | H | H | —SO$_2$Me | Cl | 3-Isoxazolyl | 186 |
| 10.12 | H | H | H | —SO$_2$Me | Cl | 5-Oxazolyl | 89–91 |
| 10.13 | Methyl | H | H | —SO$_2$Me | Cl | 5-Oxazolyl | 95–96 |
| 10.14 | Methyl | Methyl | H | —SO$_2$Me | Cl | 5-Oxazolyl | 101–106 |
| 10.15 | CH$_3$ | CH$_3$ | H | —SO$_2$CH$_3$ | Cl | 2-Thiazolyl | 172 |
| 10.16 | CH$_3$ | H | H | —SO$_2$CH$_3$ | Cl | 2-Thiazolyl | 180 |
| 10.17 | (Dimethoxy)-methyl | H | H | —SO$_2$CH$_3$ | Cl | 2-Thiazolyl | 84–86 |
| 10.18 | H | H | H | —SO$_2$CH$_3$ | Cl | 2-Thienyl | 110 |
| 10.19 | CH$_3$ | CH$_3$ | H | —SO$_2$CH$_3$ | Cl | 2-Thienyl | 104 |
| 10.20 | CH$_3$ | CH$_3$ | H | —SO$_2$CH$_3$ | H | 2-Furyl | 79–82 |
| 10.21 | CH$_3$ | CH$_3$ | H | —SO$_2$CH$_3$ | CH$_3$ | 2-Thienyl | 77–80 |
| 10.22 | CH$_3$ | CH$_3$ | H | —SO$_2$CH$_3$ | CH$_3$ | 2-Furyl | 75–79 |
| 10.23 | CH$_3$ | CH$_3$ | H | —SO$_2$CH$_3$ | Cl | 4-Methylthiazol-2-yl | 110 |
| 10.24 | CH$_3$ | CH$_3$ | H | —SO$_2$CH$_3$ | Cl | 5-Chloro-4-methylthiazol-2-yl | 102–104 |
| 10.25 | CH$_3$ | CH$_3$ | H | —SO$_2$CH$_3$ | Cl | 3-Isoxazolyl | 102–105 |
| 10.26 | H | H | H | —SO$_2$CH$_3$ | Cl | 4,5-Dihydroisoxazol-3-yl | 230 |
| 10.27 | H | H | H | —SO$_2$CH$_3$ | Cl | 5-Cyclopropylisoxazol-3-yl | 175–180 |
| 10.28 | CH$_3$ | H | H | —SO$_2$CH$_3$ | Cl | 5-Cyclopropylisoxazol-3-yl | 162–172 |
| 10.29 | CH$_3$ | H | H | —SO$_2$CH$_3$ | Cl | 4,5-Dihydroisoxazol-3-yl | 204–205 |
| 10.30 | CH$_3$ | CH$_3$ | H | —SO$_2$CH$_3$ | Cl | 4,5-Dihydroisoxazol-3-yl | 115–120 |
| 10.31 | CH$_3$ | CH$_3$ | H | —SO$_2$CH$_3$ | Cl | 5-Cyclopropylisoxazol-3-yl | 100–110 |
| 10.32 | Isopropyl | H | H | —SO$_2$CH$_3$ | Cl | 3-Isoxazolyl | 127–130 |
| 10.33 | Isopropyl | H | H | —SO$_2$CH$_3$ | Cl | 4,5-Dihydroisoxazol-3-yl | 178–180 |
| 10.34 | H | H | H | —SO$_2$CH$_3$ | H | 2-Furyl | 65–68 |
| 10.35 | CH$_3$ | CH$_3$ | H | —SO$_2$CH$_3$ | H | 2-Thienyl | 81–84 |
| 10.36 | H | H | H | —SO$_2$CH$_3$ | H | 2-Thienyl | 157–161 |
| 10.37 | CH$_3$ | CH$_3$ | H | —SO$_2$CH$_3$ | Cl | 3-Furyl | 149–153 |
| 10.38 | CH$_3$ | CH$_3$ | H | —SO$_2$CH$_3$ | Cl | 3-Thienyl | 73–77 |
| 10.39 | CH$_3$ | CH$_3$ | H | —SO$_2$CH$_3$ | H | 3-Furyl | 100–104 |
| 10.40 | H | H | H | —SO$_2$CH$_3$ | H | 3-Furyl | 64–68 |

TABLE 10-continued

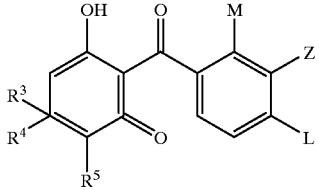

| No. | R³ | R⁴ | R⁵ | L | M | Z | Mp. [° C.] |
|---|---|---|---|---|---|---|---|
| 10.41 | CH₃ | CH₃ | H | —SO₂CH₃ | Cl | 5-Methyl-4-phenylthiazol-2-yl | 173 |

TABLE 11

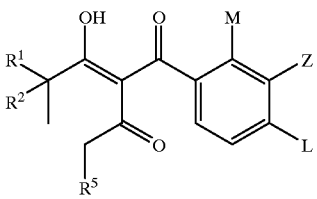

| No. | R¹ | R² | A | L | M | Z | Mp. [° C.] |
|---|---|---|---|---|---|---|---|
| 11.1 | CH₃ | CH₃ | CH=CH | —SO₂CH₃ | Cl | 2-Thiazolyl | 82 |
| 11.2 | CH₃ | CH₃ | CH₂—CH₂ | —SO₂CH₃ | Cl | 2-Thiazolyl | 254–256 |
| 11.3 | CH₃ | CH₃ | CH₂—CH₂ | —SO₂CH₃ | Cl | 4,5-Dihydroxazol-3-yl | 161–163 |
| 11.4 | CH₃ | CH₃ | CH₂—CH₂ | —SO₂CH₃ | Cl | 3-Isoxazolyl | 125–130 |

We claim:

1. A benzoyl derivative of the formula IIIa

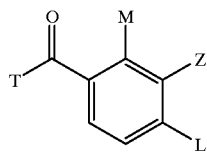

IIIa where

T is halogen, OH or $C_1$–$C_4$-alkoxy;

M is $C_1$–$C_6$-alkyl, $C_2$–$C_6$-alkenyl, $C_2$–$C_6$-alkynyl or $C_1$–$C_4$-alkoxy where these groups may be unsubstituted or substituted by one to five halogen atoms or $C_1$–$C_4$-alkoxy, or is halogen, cyano, nitro, a group —(Y)$_n$—S(O)$_m$R$^7$ or a group —(Y)—CO—R$^8$, L is $C_1$–$C_6$-alkyl, $C_2$–$C_6$-alkenyl, $C_2$–$C_6$-alkynyl or $C_1$–$C_4$-alkoxy, were these groups may be unsubstituted or substituted by one to five halogen atoms or $C_1$–$C_4$-alkoxy, or is halogen, cyano, nitro, a group (Y)$_n$—S(O)$_m$R$^7$, —(Y)—CO—R$^8$, —CO—$C_1$–$C_4$-alkyl, —CO—$C_1$–$C_4$-haloalkyl or —CONR$^9$R$^{10}$, Z is 2-furyl, 3-furyl, 2-thienyl, 3-thienyl, 3-ioxazolyl, 5-isoxazolyl, 2-oxazolyl, 5-oxazolyl, 2-thiazolyl, 1,2,4-oxadiazol-3-yl, 4,5-dihydroisoxazol-3-yl or 4,5-dihydrooxazol-2-yl, which are unsubstituted or substituted by halogen, cyano, nitro, a group —CO—R$^8$, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkythio, di-$C_1$–$C_4$-alkylamino or phenyl which may be unsubstituted or substituted by halogen, cyano, nitro, $C_1$–$C_4$-alkyl or $C_1$–$C_4$-haloalkyl;

Y is O or NR$^9$ n is zero or one, m is zero, one or two,

R$^7$ is $C_1$–$C_4$-alkyl, $C_1$–$C_4$-haloalkyl or NR$^9$R$^{10}$,

R$^8$ is $C_1$–$C_4$-alkyl, $C_1$–$C_4$-haloalkyl, $C_1$–$C_4$-alkoxy, or NR$^9$R$^{10}$, R$^9$ is hydrogen, or $C_1$–$C_4$-alkyl, R$^{10}$ is $C_1$–$C_4$-alkyl.

2. A benzoyl derivative of the formula IIIa

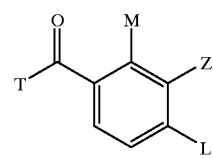

IIIa where

T is halogen, OH or $C_1$–$C_4$-alkoxy;

M is $C_1$–$C_6$-alkyl, $C_2$–$C_6$-alkenyl, $C_2$–$C_6$-alkynyl or $C_1$–$C_4$-alkoxy where these groups may be unsubstituted or substituted by one to five halogen atoms or $C_1$–$C_4$-alkoxy, or is halogen, cyano, nitro, a group —(Y)$_n$—S(O)$_m$R$^7$ or a group —(Y)—CO—R$^8$, L is $C_1$–$C_6$-alkyl, $C_2$–$C_6$-alkenyl, $C_2$–$C_6$-alkynyl or $C_1$–$C_4$-alkoxy, were these groups may be unsubstituted or substituted by one to five halogen atoms or $C_1$–$C_4$-alkoxy, or is halogen, cyano, nitro, a group (Y)$_n$—S(O)$_m$R$^7$, —(Y)—CO—R$^8$, —CO—$C_1$–$C_4$-alkyl, —CO—$C_1$–$C_4$-haloalkyl or —CONR$^9$R$^{10}$, Z is 3-isoxazolyl, 5-isoxazolyl, 2-thiazolyl or 4,5-dihydroisoxazol-3-yl which are unsubstituted or substituted by halogen, cyano, nitro, a group —CO—R$^8$, C$_1$–C$_4$-alkyl, C$_1$–C$_4$-haloalkyl, C$_3$–C$_8$-cycloalkyl, C$_1$–C$_4$-alkoxy, C$_1$–C$_4$-haloalkoxy, C$_1$–C$_4$-alkylthio, C$_1$–C$_4$-haloalkythio, di-C$_1$–C$_4$-alkylamino or phenyl, which may be unsubstituted or substituted by halogen, cyano, nitro, C$_1$–C$_4$-alkyl or C$_1$–C$_4$-haloalkyl;

Y is O or NR$^9$ n is zero or one, m is zero, one or two

R$^7$ is C$_1$–C$_4$-alkyl, C$_1$–C$_4$-haloalkyl or NR$^9$R$^{10}$,

R$^8$ is C$_1$–C$_4$-alkyl, C$_1$–C$_4$-haloalkyl, C$_1$–C$_4$-alkoxy, or NR$^9$R$^{10}$, R$^9$ is hydrogen or C$_1$–C$_4$-alkyl, R$^{10}$ is C$_1$–C$_4$-alkyl.

3. A benzoyl derivative of the formula IIIa

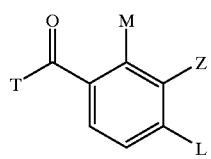

IIIa where

T is halogen, OH or C$_1$–C$_4$-alkoxy;

M is C$_1$–C$_6$-alkyl, C$_2$–C$_6$-alkenyl, C$_2$–C$_6$-alkynyl or C$_1$–C$_4$-alkoxy where these groups may be unsubstituted or substituted by one to five halogen atoms or C$_1$–C$_4$-alkoxy, or is halogen, cyano, nitro, a group —(Y)$_n$—S(O)$_m$R$^7$ or a group —(Y)—CO—R$^8$, L is C$_1$–C$_6$-alkyl, C$_2$–C$_6$-alkenyl, C$_2$–C$_6$-alkynyl or C$_1$–C$_4$-alkoxy, were these groups may be unsubstituted or substituted by one to five halogen atoms or C$_1$–C$_4$-alkoxy, or is halogen, cyano, nitro, a group (Y)$_n$—S(O)$_m$R$^7$, —(Y)—CO—R$^8$, —CO—C$_1$-C$_4$-alkyl, —CO—C$_1$–C$_4$-haloalkyl or —CONR$^9$R$^{10}$, Z is 4,5-dihydroisoxazol-3-yl which are unsubstituted or substituted by halogen, cyano, nitro, a group —CO—R$^8$, C$_1$–C$_4$-alkyl, C$_1$–C$_4$-haloalkyl, C$_3$–C$_8$-cycloalkyl, C$_1$–C$_4$-alkoxy, C$_1$–C$_4$-haloalkoxy, C$_1$–C$_4$-alkylthio, C$_1$–C$_4$-haloalkylthio, di-C$_1$–C$_4$-alkylamino or phenyl, which may be unsubstituted or substituted by halogen, cyano, nitro, C$_1$–C$_4$-alkyl or C$_1$–C$_4$-haloalkyl;

Y is O or NR$^9$ n is zero or one, m is zero, one or two

R$^7$ is C$_1$–C$_4$-alkyl, C$_1$–C$_4$-haloalkyl or NR$^9$R$^{10}$,

R$^8$ is C$_1$–C$_4$-alkyl, C$_1$–C$_4$-haloalkyl, C$_1$–C$_4$-alkoxy, or NR$^9$R$^{10}$, R$^9$ is hydrogen or C$_1$–C$_4$-alkyl, R$^{10}$ is C$_1$–C$_4$-alkyl.

4. A benzoyl derivative of the formula IIIa as claimed in claim 3, where

Z is 4,5-dihydroisoxazol-3-yl.

5. A benzoyl derivative of the formula IIIa

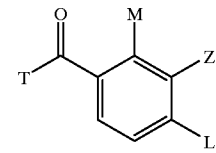

IIIa where

T is halogen, OH or C$_1$–C$_4$-alkoxy;

M is C$_1$–C$_6$-alkyl, C$_2$–C$_6$-alkenyl, C$_2$–C$_6$-alkynyl or C$_1$–C$_4$-alkoxy where these groups may be unsubstituted or substituted by one to five halogen atoms or C$_1$–C$_4$-alkoxy, or is halogen, cyano, nitro, a group —(Y)$_n$—S(O)$_m$R$^7$ or a group —(Y)—CO—R$^8$, L is C$_1$–C$_6$-alkyl, C$_2$–C$_6$-alkenyl, C$_2$–C$_6$-alkynyl or C$_1$–C$_4$-alkoxy, were these groups may be unsubstituted or substituted by one to five halogen atoms or C$_1$–C$_4$-alkoxy, or is halogen, cyano, nitro, a group (Y)$_n$—S(O)$_m$R$^7$, —(Y)—CO—R$^8$, —CO—C$_1$-C$_4$-alkyl, —CO—C$_1$–C$_4$-haloalkyl or —CONR$^9$R$^{10}$, Z is a heterocycle bonded via nitrogen selected from the group consisting of 1-pyrrolidinyl, 2,3-dihydropyrazol-1-yl, 2,3-dihydropyrazol-2-yl or 4,5-dihydropyrazol-1-yl, which is unsubstituted or substituted a) by halogen, cyano, nitro, a group —CO—R$^8$, C$_1$–C$_4$ alkyl, C$_1$–C$_4$-haloalkyl, C$_3$–C$_8$-cycloalkyl, C$_1$–C$_4$-alkoxy, C$_1$–C$_4$-haloalkoxy, C$_1$–C$_4$-alkylthio, C$_1$–C$_4$ haloalkylthio, di-C$_1$–C$_4$-alkylamino or phenyl, which may be unsubstituted or substituted by halogen, cyano, nitro, C$_1$–C$_4$-alkyl or C$_1$–C$_4$-haloalkyl or b) by an oxo group which may also be present in tautomeric form as a hydroxyl group, or c) the heterocyclic radical may form a bicyclic system with I) a fused-on phenyl ring which is unsubstituted or substituted by halogen, cyano, nitro, C$_1$–C$_4$-alkyl or C$_1$–C$_4$-haloalkyl, II) a fused-on carbocyclic structure or III) a fused-on second heterocyclic structure which is unsubstituted or substituted by halogen, cyano, nitro, C$_1$–C$_4$-alkyl, di-C$_1$–C$_4$-alkylamino, C$_1$–C$_4$-alkoxy, C$_1$–C$_4$-haloalkoxy or C$_1$–C$_4$-haloalkyl;

Y is O or NR$^9$ n is zero or one, m is zero, one or two,

R$^7$ is C$_1$–C$_4$-alkyl, C$_1$–C$_4$-haloalkyl or NR$^9$R$^{10}$,

R$^8$ is C$_1$–C$_4$-alkyl, C$_1$–C$_4$-haloalkyl, C$_1$–C$_4$-alkoxy, or NR$^9$R$^{10}$, R$^9$ is hydrogen or C$_1$–C$_4$-alkyl, R$^{10}$ is C$_1$–C$_4$-alkyl.

6. A benzoyl derivative of the formula IIIb

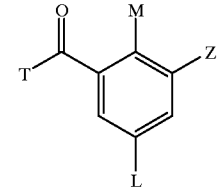

IIIb where

T is halogen, OH or C$_1$–C$_4$-alkoxy;

M is $C_1$–$C_6$-alkyl, $C_2$–$C_6$-alkenyl, $C_2$–$C_6$-alkynyl or $C_1$–$C_4$-alkoxy where these groups may be unsubstituted or substituted by one to five halogen atoms or $C_1$–$C_4$-alkoxy, or is halogen, cyano, nitro, a group —(Y)$_n$—S(O)$_m$R$^7$;

L is hydrogen, $C_1$–$C_6$-alkyl, $C_2$–$C_6$-alkenyl, $C_2$–$C_6$-alkynyl or $C_1$–$C_4$-alkoxy, where these groups may be unsubstituted or substituted by one to five halogen atoms or $C_1$–$C_4$-alkoxy, or is cyano, nitro, a group (Y)—S(O)$_m$R$^7$, SR$^7$, SOR$^7$, SO$_2$—$C_1$–$C_4$-haloalkyl or —SO$_2$NR$^9$R$^{10}$, or —(Y)$_n$—CO—R$^8$;

Z is a heterocycle bonded via nitrogen selected from the group consisting of 1-pyrrolidinyl, 2,3-dihydropyrazol-1-yl, 2,3-dihydropyrazol-2-yl or 4,5-dihydropyrazol-1-yl, which is unsubstituted or substituted a) by halogen, cyano, nitro, a group —CO—R$^8$, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino or phenyl, which may be unsubstituted or substituted by halogen, cyano, nitro, $C_1$–$C_4$-alkyl or $C_1$–$C_4$-haloalkyl or b) by an oxo group which may also be present in tautomeric from as a hydroxyl group, or c) the heterocyclic radical may form a bicyclic system with I) a fused-on phenyl ring which is unsubstituted or substituted by halogen, cyano, nitro, $C_1$–$C_4$-alkyl or $C_1$–$C_4$-haloalkyl, II) a fused-on carbocyclic structure or III) a fused-on second heterocyclic structure which is unsubstituted or substituted by halogen, cyano, nitro, $C_1$–$C_4$-alkyl, di-$C_1$–$C_4$-alkylamino, $C_1$–$C_4$-alkoxy, $C_1$–$C_4$-haloalkoxy or $C_1$–$C_4$-haloalkyl;

Y is O or NR$^9$ n is zero or one, m is zero, one or two

R$^7$ is $C_1$–$C_4$-alkyl, $C_1$–$C_4$-haloalkyl or NR$^9$R$^{10}$,

R$^8$ is $C_1$–$C_4$-alkyl, $C_1$–$C_4$-haloalkyl, $C_1$–$C_4$-alkoxy, or NR$^9$R$^{10}$, R$^9$ is hydrogen or $C_1$–$C_4$-alkyl, R$^{10}$ is $C_1$–$C_4$-alkyl.

7. A benzoyl derivative of the formula IIIa

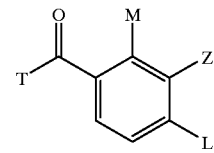

IIIa where T is halogen, OH or $C_1$–$C_4$-alkoxy; L is selected from the group consisting of SO$_2$CH$_3$, NO$_2$ and Cl; M is selected from the group consisting of H, Cl, CH$_3$ and CN; and Z is selected from the group consisting of 1-Pyrrolyl, 1,2,4-Triazol-1-yl and 3,5-Dimethyl-pyrazol-1-yl.

* * * * *

UNITED STATES PATENT AND TRADEMARK OFFICE
CERTIFICATE OF CORRECTION

PATENT NO. : 6,153,759
DATED : November 28, 2000
INVENTOR(S) : Von Deyn et al.

It is certified that error appears in the above-identified patent and that said Letters Patent is hereby corrected as shown below:

Column 73, claim 1,
Line 58, "3-ioxazolyl" should be -- 3-isoxazolyl --.

Signed and Sealed this

Second Day of October, 2001

Attest:

NICHOLAS P. GODICI
Attesting Officer
Acting Director of the United States Patent and Trademark Office